(12) United States Patent
Keegan et al.

(10) Patent No.: US 6,579,701 B1
(45) Date of Patent: Jun. 17, 2003

(54) DROSOPHILA HOMOLOGUES OF GENES AND PROTEINS IMPLICATED IN CANCER AND METHODS OF USE

(75) Inventors: Kevin Patrick Keegan, San Leandro, CA (US); Thomas J. Stout, San Francisco, CA (US)

(73) Assignee: Exelixis, Inc., South San Francisco, CA (US)

(*) Notice: Subject to any disclaimer, the term of this patent is extended or adjusted under 35 U.S.C. 154(b) by 0 days.

(21) Appl. No.: 09/738,946

(22) Filed: Dec. 14, 2000

Related U.S. Application Data
(60) Provisional application No. 60/170,832, filed on Dec. 14, 1999, provisional application No. 60/170,838, filed on Dec. 14, 1999, provisional application No. 60/178,580, filed on Jan. 28, 2000, provisional application No. 60/185,879, filed on Feb. 29, 2000, provisional application No. 60/185,880, filed on Feb. 29, 2000, provisional application No. 60/186,150, filed on Mar. 1, 2000, and provisional application No. 60/189,701, filed on Mar. 15, 2000.

(51) Int. Cl.$^7$ ................................................. C12P 21/06
(52) U.S. Cl. .................... 435/69.1; 435/320.1; 435/325; 435/455; 435/243; 435/410; 435/348; 435/352; 435/358; 435/468; 435/471; 435/252.3; 435/254.11; 536/23.1; 536/23.5
(58) Field of Search .................... 536/23.1; 435/325, 435/69.1, 455, 320.1, 243, 410, 348, 352, 358, 468, 471, 252.3, 254.11; 530/350; 578/23.5

(56) References Cited

PUBLICATIONS

Adams et al. (Genbank [online]) Bethesda, MD, USA, NCBI, retrieved on Aug. 19, 2002. Retrieved from NCBI, GenBank Accession No. AC018035.*
Sambrook et al., Molecular Cloning, A Laboratory Manual, $2^{nd}$ edition, 1988, pp. 11–47.*
Wallace, Methods Enzymol, 152:432–443, 1987.*
Igaki et al., PNAS, 97:662–667, 2000.*
Linder, LAB Animal, 30: 34–39, 2001.*
McClean, DNA– Basics of Structure and Analysis [online], 1998 [retrieved on May 19, 2002]. Retrieved from http://www.ndsu.nodak.edu/instruct/mclean/plsc731/dna/dna6.htm pp. 1–6.*
Molecular Biology of the Cell [online]. $3^{rd}$ edition. Garland Publishing, 1994 [retrieved on Sep. 3, 2002]. Retrieved from http://www.ncbi.nlm.nih.gov/books/bv.fcgi?call=bv.Vie..ShowSection&rid=cell Chapter 7, pp. 1–9.*
Chiu et al., Optimizing energy potentials for success in protein tertiary structure prediction, 1998, Folding & Design, vol. 3, pp. 223–228.*
Wells et al., The chemokine information source: identification and characterization of novel chemnokines using the worldwideweb expressed sequence tag databases, 1997, Journal of Leukocyte Biology, vol. 61, pp. 545–550.*

Gerhold et al., It's the genes! EST access to human genome content, 1996, Bioessays, vol. 18, pp. 973–981.*
Russell et al., Structural features can be unconserved in proteins with similar folds, 1994, J. Mol. Biol., vol. 244, pp. 332–350.*
Celniker,S.E., et al. "*Drosophila melanogaster* chromosome 2 clone BACR10F15 (D621) RPCI–98 10.F.15 map 42E–43A strain y; cn bw sp" Genbank GI No. 5670596, Aug. 2, 1999.
Celniker,S.E., et al. "*Drosophila melanogaster* chromosome 2 clone BACR10F15 (D621) RPCI–9810F.15 map 42E–43A strain y2; cn bw sp" Genbank GI No. 4887256, May 25, 1999.
Celniker,S.E., et ak, "*Drosophila melanogaster* chromosome 2 clone BACR01C10 (D620) RPCI–9801.C.10 map 42E–43A strain y2; cn bw sp" Genbank GI No. 4885670, May 24, 1999.
Harvey,D., et al, "GH01265.3prime GH *Drosophila melanogaster* head pOT2 Drosophila melanogaster cDNA clone GH01265 3prime, mRNA sequence" Genbank GI No. 4417483,Apr. 19, 2001.
Harvey,D., et al., "LD12719.5prime LD *Drosophila melanogaster* embryo BlueScript Drosophila melanogaster cDNA clone LD12719 5prime, mRNA sequence" Genbank GI No.2152793, Apr. 19, 2001.
Zhang,H., et al. "BCL–2–related ovarian killer protein [*Homo sapiens*]" Genbank GI No.5802578, Sep. 15, 2000.
Hsu,S.Y. et al, "Bcl–2 related ovarian killer [*Homo sapiens*]" Genbank GI No. 6456033, Nov. 20, 1999.
Hsu,S.Y., "Bcl–2–related ovarian killer protein [*Rattus norvegicus*]" Genbank GI No. 2645560, Nov. 27, 1997.
Inohara,N., et al., "apoptosis activator Mtd [*Mus musculus*]" Genbank GI No. 2689660, May 5, 1998.
Hsu,S.Y., et al., "Bcl–2–related ovarian killer protein [*Rattus norvegicus*]" Genbank GI No. 3676403, Sep. 30, 1998.
Adams,M. et al., "*Drosophila melanogaster*" Genbank GI No. 6223261, Nov. 3, 1999.

(List continued on next page.)

*Primary Examiner*—Scott D. Priebe
*Assistant Examiner*—Brian Whiteman
(74) *Attorney, Agent, or Firm*—Laleh Shayesteh; Jan P. Brunelle

(57) ABSTRACT

Novel nucleic acids that are homologs of genes implicated in cancer are described that have been isolated from *Drosophila melanogaster*. These novel nucleic acids can be used to genetically modify metazoan invertebrate organisms, such as insects and worms, or cultured cells, resulting in novel gene expression or mis-expression. The genetically modified organisms or cells can be used in screening assays to identify candidate compounds which are potential pesticidal agents or therapeutics that interact with gene products implicated in cancer. They can also be used in methods for studying gene activity and identifying other genes that modulate the function of, or interact with, genes implicated in cancer.

5 Claims, No Drawings

OTHER PUBLICATIONS

Celniker,S.E., et al., "*Drosophila melanogaster* chromosome 3 clone BACR02L16 (D715) RPCI–98 02.L.16 map 89E–90A strain y; cn bw sp" Genbank GI No. 5670523, Aug. 2, 1999.

Celniker,S.E., et al., "*Drosophila melanogaster* chromosome 3 clone BACR01E04 (D714) RPCI–98 01.E.4 map 89E–89E strain y; cn bw sp" Genbank GI No. 5053157, Jun. 14, 1999.

Celniker,S.E., et al., "*Drosophila melanogaster* chromosome 3 clone BACR01E04 (D714) RPCI–98 01.E.4 map 89E–89E strain y; cn bw sp" Genbank GI No. 5670524, Aug. 2, 1999.

Kobayashi,K., et al., "*Mus musculus* mRNA for TIAP, complete cds" Genbank GI No. 3135206, Feb. 25, 1999.

Uren,A.G., "inhibitor of apoptosis homolog [Homo sapiens]" Genbank GI No. 4959079, Dec. 14, 2000.

Altieri,D.C., "apoptosis inhibitor survivin [*Homo sapiens*]" Genbank GI No. 2315863, Aug. 9, 1997.

Conway,E.M., et al., "survivin140 [*Mus musculus*]" Genbank GI No. 4588768, Apr. 20, 1999.

Uren,A.G., et al., "inhibitor of apoptosis homolog [*Mus musculus*]" Genbank GI No. 4959077, Dec. 14, 2000.

Conway,E.M., "survivin121 [*Mus musculus*]" Genbank GI No. 4588770, Apr. 20, 1999.

Celniker,S.E., et al., "*Drosophila melanogaster* chromosome 3 clone BACR42H10 (D671) RPCI–98 42.H.10 map 82F–83A strain y; cn bw sp" Genbank GI No. 5670561, Aug. 2, 1999.

Celniker,S.E., et al., "*Drosophila melanogaster* chromosome 3 clone BACR42H10 (D671) RPCI–98 42.H.10 map 82F–83A strain y2; cn bw sp" Genbank GI No. 4878045, May 20, 1999.

Celniker,S.E., et al., "*Drosophila melanogaster* chromosome 3 clone BACR01D10 (D670) RPCI–98 01.D.10 map 82F–82F strain y2; cn bw sp" Genbank GI No. 4878046, May 20, 1999.

Celniker,S.E., et al., "*Drosophila melanogaster* chromosome 3 clone BACR01D10 (D670) RPCI–98 01.D.10 map 82F–82F strain y; cn bw sp" Genbank GI No. 5670562, Aug. 2, 1999.

Adams,M. et al., "*Drosophila melanogaster*" Genbank GI No. 6437379, Nov. 16, 1999.

Wax,S.D., et al., "growth factor–responsive protein, vascular smooth muscle—rat." Genbank GI No. 631839, Nov. 5, 1999.

Wax,S.D., et al., "SM–20" Genbank GI No. 469478, Jun. 29, 1994.

Darby,C., et al., "EGL–9 [*Caenorhabditis elegans*]" Genbank GI No. 5923812, Dec. 23, 1999.

no author, "contains similarity to Pfam domain: PF00104 (Ligand–binding domain of nuclear hormone receptor)", Genbank GI No. 3880793; Jan 24, 2002.

no author, "Weak similarity with apoptosis protein RP–8, contains similarity to Pfam domain: PF01753 (MYND finger)", Genbank GI No. 3876300, Oct. 25, 2000.

Adams,M., et al., "*Drosophila melanogaster*" Genbank GI No. 6554259, Dec. 10, 1999.

Harvey,D., et al., "SD04095.5prime SD *Drosophila melanogaster* Schneider L2 cell culture pOT2 *Drosophila melanogaster* cDNA clone SD04095 5prime, mRNA sequence" Genbank GI No. 4446690, Apr. 19, 2001.

Harvey,D., et al., "SD03917.5prime SD *Drosophila melanogaster* Schneider L2 cell culture pOT2 *Drosophila melanogaster* cDNA clone SD03917 5prime, mRNA sequence" Genbank GI No. 4446544, Apr. 19, 2001.

Harvey,D., et al., "LP07167.5prime LP *Drosophila melanogaster* larval–early pupal pOT2 *Drosophila melanogaster* cDNA clone LP07167 5prime, mRNA sequence", Genbank GI No. 3943315, Apr. 19, 2001.

no author, "*Drosophila melanogaster* genome survey sequence TET3 end of BAC # BACR18C01 of RPCI–98 library from *Drosophila melanogaster* (fruit fly), genomic survey sequence", Genbank GI No. 4934221, Jun. 3, 1999.

no author, "Similarity to Mouse meltrin alpha protein (TR:Q61824), contains similarity to Pfam domain: PF00200 (Disintegrin)", Genbank GI No. 3873969, Jan. 24, 2002.

no author, "Similarity to Mouse meltrin alpha protein (TR:Q61824), contains similarity to Pfam domain: PF00200 (Disintegrin)", Genbank GI No. 387812, Jan. 23, 2002.

Yagami–Hiromasa,T., et al., "meltrin alpha—mouse", Genbank GI No. 2137512, Jun. 20, 2000.

Yagami–Hiromasa,T., et al., "meltrin alpha—mouse", Genbank GI No. 2137512, Jun. 20, 2000.

Yagami–Hiromasa,T., et al., "meltrin alpha [*Mus musculus*]", Genbank GI No. 1054587, Nov. 2, 2000.

Adams,M., et al., "*Drosophila melanogaster*", Genbank GI No. 6436998, Nov. 16, 1999.

Celniker,S.E., et al., "*Drosophila melanogaster*, chromosome 2L, region 34B5–34B9, P1 clone DS05554, complete sequence", Genbank GI No. 4056409, Dec. 23, 1998.

Harvey,D., et al., "GH09630.5prime GH *Drosophila melanogaster* head pOT2 *Drosophila melanogaster* cDNA clone GH09630 5prime, mRNA sequence", Genbank GI No. 3478471, Apr. 19, 2001.

Harvey,D., et al., "GH17072.5prime GH *Drosophila melanogaster* head pOT2 *Drosophila melanogaster* cDNA clone GH17072 5prime, mRNA sequence", Genbank GI No. 4200817, Apr. 19, 2001.

Harvey,D. et al., "GH09630.3prime GH *Drosophila melanogaster* head pOT2 *Drosophila melanogaster* cDNA clone GH09630 3prime, mRNA sequence" Genbank GI No. 4245268, Apr. 19, 2001.

Lyne,M. et al., "putative transcription factor tfiiib component.[*Schizosaccharomyces pombe*]" Genbank GI No. 4107317, Jan. 14, 2000.

Kassavetis,G.A., et al., "transcription initiation factor IIIB chain B"–yeast (*Saccharomyces cerevisiae*)" Genbank GI No. 2133106, Jul. 21, 2000.

Duesterhoeft,A., et al., "ORF YNL039w [*Saccharomyces cerevisiae*]" Genbank GI No. 1301890, Aug. 11, 1997.

Kassavetis,G.A., et al., "transcription factor TFIIIB B" component" Genbank GI No. 101915, Oct. 12, 1995.

Roberts,S., et al., "transcription factor TFIIIB90" Genbank GI No. 052983, Jun. 21, 1996.

Adams,M. et al., "*Drosophila melanogaster*" Genbank GI No. 6436787, Nov. 16, 1999.

Celniker,S.E., et al., "*Drosophila melanogaster* chromosome 2 clone DS06766 (D434) map 41D1–41D2 strain y; cn bw sp" Genbank GI No. 5656713, Jul. 30, 1999.

Celniker,S.E., et al., "*Drosophila melanogaster* chromosome 2 clone DS07289 (D337) map 41E3–41E6 strain y; cn bw sp" Genbank GI No. 5649331, Jul. 29, 1999.

Genoscope, "*Drosophila melanogaster* genome survey sequence TET3 end of BAC: BACR31H22 of RPCI–98 library from *Drosophila melanogaster* (fruit fly), genomic survey sequence" Genbank GI No. 4951078, Jun. 3, 1999.

Alm,R.A., "putative Flagellar Biosynthesis Protein [*Helicobacter pylori* J99]" Genbank GI No. 4154928, Jan. 20, 1999.

McMahon,S.B., et al., "TRRAP protein [*Homo sapiens*]" Genbank GI No. 4165077, Jan. 26, 1999.

Vassilev,A., et al., "PCAF–associated factor 400 [*Homo sapiens*]" Genbank GI No. 4151929, Jan. 13, 1999.

Stoneking,T., et al., "similar to hypothetical proteins P38811 (PID:g731689) and Q10064" Genbank GI No. 3694663, Dec. 21, 1999.

Vaudin,M., et al., "hypothetical protein YHR099w—yeast (*Saccharomyces cerevisiae*)" Genbank GI No. 626646, Oct. 29, 1999.

Johnston,M., et al., "Tra1p [*Saccharomyces cerervisiae*]" Genbank GI No. 487929, Sep. 4, 1997.

Adams,M.,et al., "*Drosophila melanogaster*" Genbank GI No. 6664986, Jan. 3, 2000.

Adams,M., et al., "*Drosophila melanogaster*" Genbank GI No. 6665028, Jan. 3, 2000.

Vogelstein,B., et al., "Sequence 1 from patent US 5571905" Genbank GI No. 1819311, Feb. 6, 1997.

Vogelstein,B., et al., "Sequence 1 from patent US 5576422" Genbank GI No. 1819835, Feb. 6, 1997.

Vogelstein,B., et al., "Sequence 1 from patent US 5693536" Genbank GI No. 3014589, Apr. 3, 1998.

Vogelstein,B., et al., "Sequence 2 from patent US 5571905" Genbank GI No. 1828481, Feb. 7, 1997.

Vogelstein,B., et al., "Sequence 2 from patent US 5576422" Genbank GI No. 1828732, Feb. 7, 1997.

Vogelstein,B., et al., "Sequence 2 from patent US 5693536." Genbank GI No. 3015128, Apr. 3, 1998.

Kinzler,K.W., et al., "colorectal tumor suppressor protein—human" Genbank GI No. 107363, Jul. 21, 2000.

Kinzler,K.W., et al., "colorectal mutant cancer protein" Genbank GI No. 181035, Nov. 1, 1994.

\* cited by examiner

DROSOPHILA HOMOLOGUES OF GENES AND PROTEINS IMPLICATED IN CANCER AND METHODS OF USE

REFERENCE TO PENDING APPLICATION

This application claims priority to provisional applications No. 60/170,832, filed on Dec. 14, 1999; No. 60/170,838, filed on Dec. 14, 1999; No. 60/178,580 filed on Jan. 28, 2000; No. 60/185,879, filed on Feb. 29, 2000; No. 60/185,880, filed on Feb. 29, 2000; No. 60/186,150, filed on Mar. 1, 2000; and No. 60/189,701, filed on Mar. 15, 2000; the entire contents of which are incorporated herein by reference.

BACKGROUND OF THE INVENTION

Apoptosis, also known as programmed cell death, is important in embryonic development, metamorphosis, tissue renewal, and hormone-induced tissue atrophy, and is implicated in many pathological conditions. In multicellular organisms, apoptosis ensures the elimination of superfluous cells including those that are generated in excess, have already completed their specific functions or are harmful to the whole organism. In reproductive tissues that are characterized by cyclic functional changes, massive cell death occurs under the control of hormonal signals. A growing body of evidence suggests that the intracellular "death program" activated during apoptosis is similar in different cell types and conserved during evolution (Thompson, Science (1995) 267:1456–1462; Steller, Science (1995) 267:1445–1449). Apoptosis is induced by events such as growth factor withdrawal and toxins, and is controlled by inhibitory or "anti-apoptotic" regulators, and by "pro-apoptotic" regulators that block the protective effect of inhibitors (Vaux, Curr. Biol. (1993) 3:877–878; White, Genes Dev. (1996) 10:2859–2869). Many viruses have anti-apoptosis genes that prevent their target-cells from entering into defensive apoptosis.

Apoptosis involves two essential steps: a "decision" step and an "execution" step. The Bcl-2 family of proteins, which comprises several anti- and pro-apoptotic members, is implicated in a cell's decision whether to undergo apoptosis (Kroemer, Nat. Med. (1997) 3:614–620). The execution step is mediated by the activation of caspases and cysteine proteases that induce cell death via the proteolytic cleavage of substrates vital for cellular homeostasis (Miura et al., Cell (1993) 75:653–660; Yuan et al., Cell (1993) 75:641–652). Bcl-2-related proteins act upstream from caspases in the cell death pathway (Hengartner and Horvitz, Cell (1994) 76:665–676). Recent studies demonstrated that a C. elegans gene, ced-4, which is homologous to the mammalian gene Apaf-1, can bridge between Bcl-2/ced-9 family members and caspases (Chinnaiyan et al., Science (1997) 275:1122–1126; Zou et al., (1997) Cell 90:405–413).

The regulation of apoptosis depends both on stimulatory and inhibitory pathways. One class of inhibitory proteins comprises the Inhibitor of Apoptosis Proteins, or IAPs. These proteins were initially discovered in baculoviruses, which utilize IAPs to prevent their target cell from entering into defensive apoptosis. IAPs were subsequently found to exist in many multicellular organisms including flies, mice, and humans (for review see Deveraux and Reed, Genes & Dev. (1999) 13:239–252.). IAPs contain from one to three repeats of an amino acid domain called a baculovirus inhibitor of apoptosis repeat, abbreviated "BIR". The BIR motif comprises about 70 residues arranged in tandem repeats separated by a linker of variable length. These repeats are intrinsic to the inhibitory activity of these proteins, and have been shown to inhibit caspases. BIRs also interact with and block other upstream pro-apoptotic proteins.

Growth factor receptors activate intracellular phosphorylation cascades that lead to changes in gene expression. The genes that growth factors induce fall into two classes: (1) early response genes that are induced immediately after growth factor treatment and that do not require protein synthesis for their induction, and (2) delayed response genes that require protein synthesis for induction (Almendral et al., Mol Cell Biol. (1988) 8:2140–2148; Naeve et al., Curr Opin Cell Biol. (1991) 3:261–268). Early response genes are not transcribed in resting cells, but are induced to high levels when growth factors are added to the medium. The best studied early response genes are the myc, fos and jun protooncogenes, all of which encode gene regulatory proteins that cause uncontrolled proliferation if overexpressed or hyperactivated. Thus understanding the signaling pathways of growth factor response proteins may lead to targets for cancer therapeutics.

The ADAM family of transmembrane proteins (ADAMs) contain disintegrin and metalloprotease domains and, therefore, potentially have both cell adhesion and protease activities. Members of the ADAM family have been implicated in many biological processes involving cell-cell and cell-matrix interactions, such as fertilization, processing of ectodomain proteins such as TNF, neurogenesis, muscle fusion, and Notch-mediated signaling (Schlondorff and Blobel, J Cell Sci (1999) 112(Pt 21):3603–3617; Wolfsberg et al.; J. Cell Biol. (1995) 131: 275–278).

ADAMs share all or some of the following domain structures: a signal peptide, a propeptide, a metalloproteinase domain, a disintegrin domain, a cysteine-rich domain, an epidermal growth factor (EGF)-like domain, a transmembrane region, and a cytoplasmic tail. ADAMs are widely distributed in many organs, tissues, and cells, such as brain, testis, epididymis, ovary, breast, placenta, liver, heart, lung, bone, and muscle. These proteins are capable of four potential functions: proteolysis, adhesion, fusion, and intracellular signaling.

The only known member of ADAMs in invertebrates is the Drosophila Kuzbanian (Qi et al., Science. (1999) 283 (5398):91–94). The ADAM ligand/enzyme proteins may play a role in other developmental system in Drosophila where integrins are known to be important, such as determination of synaptic specificity (Beumer et al., Development (1999)126(24):5833–5846), wing morphogenesis (Brabant et al., Ann N Y Acad Sci (1998) 857:99–109), midgut cell migration (Martin-Bermudo et al., Development (1999) 126(22):5161–9), axon guidance (Hoang and Chiba, J Neurosci (1998) 18(19):7847–7855, and olfactory memory (Connolly and Tully, Curr Biol (1998) 8(11):R386–389).

The c-Myb and v-Myb proteins are transcription factors that regulate cell proliferation and differentiation (Ness, Oncogene (1999) 18(19):3039–3046). Both Myb proteins have been shown to interact with a number of cellular proteins, some of which are transcription factors that cooperate to activate specific promoters, while others regulate the transcriptional activity of Myb (Ness, supra). Transcription factors such as myb have been found to be oncogenic either when functionally altered through fusion with other proteins or through deregulated expression (Introna and Golay, Leukemia (1999) 13(9):1301–1306). In addition, clinical trials for the treatment of human leukemias by antisense-mediated disruption of the myb gene are underway (Gewirtz, Oncogene (1999) May 18(19):3056–3062). Thus, disruption of myb function, possibly by small molecule inhibitors of protein-protein interactions, may be an effective treatment for human malignancies. Hematopoietic tumors in both humans and mice frequently up-regulate expression of the c-myb gene, but it is unclear whether this is a cause or a consequence of the leukemic state (Weston, Oncogene (1999) 18(19):3034–3038). However, support for the idea that myb may be a target for cancer treatment is found in the recent discovery that c-Myb levels in colon tumor cells may lead to persistent bcl-2 expression, thus protecting tumor cells from programmed cell death (Thompson et al., Cancer Res. (1998) 58(22):5168–5175). This finding implies that interference with increased c-Myb levels may promote apoptosis, a natural defense against renegade cancer cells.

Phosphatidylinositol, a component of eukaryotic cell membranes, is unique among phospholipids in that its head group can be phosphorylated at multiple free hydroxyls. Several phosphorylated derivatives of phosphatidylinositol, collectively termed phosphoinositides, have been identified in eukaryotic cells from yeast to mammals. Phosphoinositides are involved in the regulation of diverse cellular processes, including proliferation, survival, cytoskeletal organization, vesicle trafficking, DNA damage response, glucose transport, and platelet function. The enzymes that phosphorylate phosphatidylinositol and its derivatives are termed phosphoinositide kinases. Phosphatidylinositol (PI)-3 kinase is an enzyme that phosphorylates the D-3 position of PI and its derivatives. It is activated immediately after growth factor or differentiation factor stimulation, suggesting that PI-3 kinase (PI3K) is involved in signal transduction of the stimulation, and thus, involved in all the aforementioned pathways (Carpenter and Cantley, Curr.Opin. Cell Biol. (1996) 8:153–158). Several PI 3K-like genes have been identified in various eukaryotic organisms (Keith and Schreiber, Science (1995) 270:50–51), including the *Saccharomyces cerevisiae* TEL1 gene (Greenwell et al., Cell (1995) 82(5):823–829), *Drosophila melanogaster* cpK (Moltz et al., J. Biol. Chem. (1996) 271:13892–13899) DNA repair (mei-41) genes (Hari et al., Cell (1995) 82(5):815–821), the human ATM gene implicated in Ataxia-telangiectasia autosomal recessive disorder (Savitsky et al., Science (1995) 268:1749–1753), TRRAP (McMahon et al., Cell (1998) 94:363–374), and PCAF (Vassilev et al., Molec. Cell (1998) 2:869–875).

Cancer is a genetic disease. The idea that multiple mutations are necessary for the development of malignancy is accepted and well illustrated by studies of colorectal cancer (Kinzler and Vogelstein, Cell (1996) 87:159–170). One of the genes involved in the tumorigenesis of colon cancer is "mutated in colon cancer", or MCC (Kinzler et al., Science, (1991) 251:1366–1370). The human MCC protein is an 829-amino acid protein with a short region of similarity to the G-protein coupled m3 muscarinic acetylcholine receptor. Not much is known about the MCC protein function. Recent molecular studies on the MCC protein have provided initial clues to its involvement in the progression of cell cycle (Matsumine, Nippon Rishno (1996) 54:981–985). Clearly, identification of homologues of MCC in other organisms has significant implications for understanding the function of this gene, and ultimately, for understanding the pathogenesis of colorectal neoplasia. To date, only the human MCC gene and protein have been cloned and sequenced.

SUMMARY OF THE INVENTION

It is an object of the present invention to provide invertebrate homologs of genes implicated in cancer that can be used in genetic screening methods to characterize pathways that cancer-related genes may be involved in as well as other interacting genetic pathways. It is also an object of the invention to provide methods for screening compounds that interact with cancer-related genes such as those that may have utility as therapeutics. These and other objects are provided by the present invention which concerns the identification and characterization of novel genes in *Drosophila melanogaster*. Isolated nucleic acid molecules are provided that comprise nucleic acid sequences encoding homologs of the following cancer-related genes: Bcl-2, hereinafter referred to as dmBCL2; a regulator of apoptosis, hereinafter referred to as dmSURVIVIN; a growth factor response protein (GFRP), hereinafter referred to as dmGFRP; a protein with disintegrin and metalloprotein domains (ADAM), hereinafter referred to as dmADAM; Myb, hereinafter referred to as dmMYB; a Phosphoinositide 3 kinase (PI3K), hereinafter referred to as dmPI3K; and the protein referred to as "mutated in colon cancer" (MCC), hereinafter referred to as dmMCC. The invention also includes novel fragments and derivatives of these nucleic acid molecules. Vectors and host cells comprising the subject nucleic acid molecules are also described, as well as metazoan invertebrate organisms (e.g. insects, coelomates and pseudocoelomates) that are genetically modified to express or mis-express subject proteins.

An important utility of the novel subject nucleic acids and proteins is that they can be used in screening assays to identify candidate compounds that are potential therapeutics that interact with subject proteins. Such assays typically comprise contacting a subject protein or fragment with one or more candidate molecules, and detecting any interaction between the candidate compound and the subject protein. The assays may comprise adding the candidate molecules to cultures of cells genetically engineered to express subject proteins, or alternatively, administering the candidate compound to a metazoan invertebrate organism genetically engineered to express subject protein.

The genetically engineered metazoan invertebrate animals of the invention can also be used in methods for studying subject gene activity. These methods typically involve detecting the phenotype caused by the expression or mis-expression of the subject protein. The methods may additionally comprise observing a second animal that has the same genetic modification as the first animal and, additionally has a mutation in a gene of interest. Any difference between the phenotypes of the two animals identifies the gene of interest as capable of modifying the function of the gene encoding the subject protein.

DETAILED DESCRIPTION OF THE INVENTION

The use of invertebrate model organism genetics and related technologies can greatly facilitate the elucidation of biological pathways (Scangos, Nat. Biotechnol. (1997) 15:1220–1221; Margolis and Duyk, supra). Of particular use is the insect model organism, *Drosophila melanogaster* (hereinafter referred to generally as "Drosophila"). An extensive search for homologues of vertebrate cancer nucleic acids and their encoded proteins in Drosophila was conducted in an attempt to identify new and useful tools for probing the function and regulation of such genes, and for use as targets in drug discovery.

The novel nucleic acids encoded proteins that are homologs of the following human proteins implicated in cancer: BCL2, SURVIVIN, GFRP ADAM, MYB, PI3K, and MCC. The nucleic acids and proteins of the invention are collectively referred to as "subject nucleic acids", "subject genes", or "subject proteins". The newly identified subject nucleic acids can be used for the generation of mutant phenotypes in animal models or in living cells that can be used to study regulation of subject genes, and the use of subject genes as drug targets. Due to the ability to rapidly carry out large-scale, systematic genetic screens, the use of invertebrate model organisms such as Drosophila has great utility for analyzing the expression and mis-expression of subject proteins. Thus, the invention provides a superior approach for identifying other components involved in the synthesis, activity, and regulation of subject proteins. Systematic genetic analysis of subject genes using invertebrate model organisms can lead to the identification and validation of compound targets directed to components of the genetic pathways these genes are involved in. Model organisms or cultured cells that have been genetically engineered to express each subject gene can be used to screen candidate compounds for their ability to modulate subject genes' expression or activity, and thus are useful in the identification of new drug targets, therapeutic agents, diagnostics and prognostics useful in the treatment of disorders such as cancerous conditions. The details of the conditions used for the identification and/or isolation of novel subject nucleic acids and proteins are described in the Examples section below. Various non-limiting embodiments of the invention, applications and uses of these novel subject genes and proteins are discussed in the following sections. The entire contents of all references, including patent applications, cited herein are incorporated by reference in their entireties for all purposes. Additionally, the citation of a reference in the preceding background section is not an admission of prior art against the claims appended hereto.

Nucleic Acids of the Invention

The invention relates generally to subject nucleic acid sequences, and more particularly to subject nucleic acid sequences of Drosophila. As described in the Examples below, nucleic acid sequences (SEQ ID NOs:1, 3, 5, 7, 9, 11, and 13) were isolated from Drosophila that encode BCL2, SURVIVIN, GFRP, ADAM, MYB, PI3K, and MCC homologs, respectively. In addition to the fragments and derivatives of SEQ ID NOs:1, 3, 5, 7, 9, 11, and 13 as described in detail below, the invention includes the reverse complements thereof. Also, the subject nucleic acid sequences, derivatives and fragments thereof may be RNA molecules comprising the nucleotide sequences of SEQ ID NOs:1, 3, 5, 7, 9, 1 1, and 13 (or derivatives or fragments thereof) wherein the base U (uracil) is substituted for the base T (thymine). The DNA and RNA sequences of the invention can be single- or double-stranded. Thus, the term "isolated nucleic acid sequence", as used herein, includes the reverse complement, RNA equivalent, DNA or RNA single- or double-stranded sequences, and DNA/RNA hybrids of the sequence being described, unless otherwise indicated.

Fragments of the subject nucleic acid sequences can be used for a variety of purposes. Interfering RNA (RNAi) fragments, particularly double-stranded (ds) RNAi, can be used to generate loss-of-function phenotypes. Subject nucleic acid fragments are also useful as nucleic acid hybridization probes and replication/amplification primers. Certain "antisense" fragments, i.e. that are reverse complements of portions of the coding sequence of SEQ ID NOs:1, 3, 5, 7, 9, 11, and 13 have utility in inhibiting the function of subject proteins. The fragments are of length sufficient to specifically hybridize with the corresponding SEQ ID NOs:1, 3, 5, 7, 9, 11, and 13. The fragments consist of or comprise at least 12, preferably at least 24, more preferably at least 36, and more preferably at least 96 contiguous nucleotides of SEQ ID NOs:1, 3, 5, 7, 9, 11, and 13. When the fragments are flanked by other nucleic acid sequences, the total length of the combined nucleic acid sequence is less than 15 kb, preferably less than 10 kb or less than 5 kb, more preferably less than 2 kb, and in some cases, preferably less than 500 bases.

Additional preferred fragments of SEQ ID NO:5 encode a zinc finger domain which are located at approximately nucleotides 590–704.

Additional preferred fragments of SEQ ID NO:7 encode extracellular or intracellular domains which are located at approximately nucleotides 478–806, 856–2192, and 2241–2820.

The subject nucleic acid sequences may consist solely of SEQ ID NOs:1, 3, 5, 7, 9, 11, or 13 or fragments thereof. Alternatively, the subject nucleic acid sequences and fragments thereof may be joined to other components such as labels, peptides, agents that facilitate transport across cell membranes, hybridization-triggered cleavage agents or intercalating agents. The subject nucleic acid sequences and fragments thereof may also be joined to other nucleic acid sequences (i.e. they may comprise part of larger sequences) and are of synthetic/non-natural sequences and/or are isolated and/or are purified, i.e. unaccompanied by at least some of the material with which it is associated in its natural state. Preferably, the isolated nucleic acids constitute at least about 0.5%, and more preferably at least about 5% by weight of the total nucleic acid present in a given fraction, and are preferably recombinant, meaning that they comprise a non-natural sequence or a natural sequence joined to nucleotide (s) other than that which it is joined to on a natural chromosome.

Derivative sequences of subject nucleic acids include sequences that hybridize to the nucleic acid sequence of SEQ ID NOs:1, 3, 5, 7, 9, 11, or 13 under stringency conditions such that the hybridizing derivative nucleic acid is related to the subject nucleic acid by a certain degree of sequence identity. A nucleic acid molecule is "hybridizable" to another nucleic,acid molecule, such as a cDNA, genomic DNA, or RNA, when a single stranded form of the nucleic acid molecule can anneal to the other nucleic acid molecule. Stringency of hybridization refers to conditions under which nucleic acids are hybridizable. The degree of stringency can be controlled by temperature, ionic strength, pH, and the presence of denaturing agents such as formamide during hybridization and washing. As used herein, the term "stringent hybridization conditions" are those normally used by one of skill in the art to establish at least a 90% sequence identity between complementary pieces of DNA or DNA and RNA. "Moderately stringent hybridization conditions" are used to find derivatives having at least 70% sequence identity. Finally, "low-stringency hybridization conditions" are used to isolate derivative nucleic acid molecules that share at least about 50% sequence identity with the subject nucleic acid sequence.

The ultimate hybridization stringency reflects both the actual hybridization conditions as well as the washing conditions following the hybridization, and it is well known in the art how to vary the conditions to obtain the desired result. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). A preferred derivative nucleic acid is capable of hybridizing to SEQ ID NOs:1, 3, 5, 7, 9, 11, and 13 under stringent hybridization conditions that comprise: prehybridization of filters containing nucleic acid for 8 hours to overnight at 65° C. in a solution comprising 6×single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18–20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.2×SSC and 0.1% SDS (sodium dodecyl sulfate).

Derivative nucleic acid sequences that have at least about 70% sequence identity with SEQ ID NOs:1, 3, 5, 7, 9, 11, and 13 are capable of hybridizing to SEQ ID NOs:1, 3, 5, 7, 9, 11, and 13 under moderately stringent conditions that comprise: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% Ficoll, 1% BSA, and 500 µg/ml denatured salmon sperm DNA; hybridization for 18–20 h at 40° C. in a solution containing 35% formamide, 5×SSC, 50 mM Tris-HCl (pH7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Other preferred derivative nucleic acid sequences are capable of hybridizing to SEQ ID NOs:1, 3, 5, 7, 9, 11, and 13 under low stringency conditions that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 370 C for 1 hour.

As used herein, "percent (%) nucleic acid sequence identity" with respect to a subject sequence, or a specified portion of a subject sequence, is defined as the percentage of nucleotides in the candidate derivative nucleic acid sequence identical with the nucleotides in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403–410; hereinafter referred to generally as "BLAST") with all the search parameters set to default values. The HSP S and HSP S2 parameters are dynamic values and are established by the program itself depending upon the composition of the particular sequence and composition of the particular database against which the sequence of interest is being searched. A percent (%) nucleic acid sequence identity value is determined by the number of matching identical nucleotides divided by the sequence length for which the percent identity is being reported.

Derivative subject nucleic acid sequences usually have at least 70% sequence identity, preferably at least 80% sequence identity, more preferably at least 85% sequence identity, still more preferably at least 90% sequence identity, and most preferably at least 95% sequence identity with SEQ ID NOs:1, 3, 5, 7, 9, 11, or 13 or domain-encoding regions thereof.

In one preferred embodiment, the derivative nucleic acid encodes a polypeptide comprising a subject amino acid sequence of any of SEQ ID NOs:2, 4, 6, 8, 10, 12, or 14 or a fragment or derivative thereof as described further below under the subheading "Proteins of the Invention". A derivative subject nucleic acid sequence, or fragment thereof, may comprise 100% sequence identity with SEQ ID NOs:1, 3, 5, 7, 9, 11, or 13 but be a derivative thereof in the sense that it has one or more modifications at the base or sugar moiety, or phosphate backbone. Examples of modifications are well known in the art (Bailey, Ullmann's Encyclopedia of Industrial Chemistry (1998), 6th ed. Wiley and Sons). Such derivatives may be used to provide modified stability or any other desired property.

Another type of derivative of the subject nucleic acid sequences includes corresponding humanized sequences. A humanized nucleic acid sequence is one in which one or more codons has been substituted with a codon that is more commonly used in human genes. Preferably, a sufficient number of codons have been substituted such that a higher level expression is achieved in mammalian cells than what would otherwise be achieved without the substitutions. Tables are available that show, the codon frequency in humans for each amino acid (Wada et al., Nucleic Acids Research (1990) 18(Suppl.):2367–2411). Thus, a subject nucleic acid sequence in which the glutamic acid codon, GAA has been replaced with the codon GAG, which is more commonly used in human genes, is an example of a humanized subject nucleic acid sequence. A detailed discussion of the humanization of nucleic acid sequences is provided in U.S. Pat. No. 5,874,304 to Zolotukhin et al. Similarly, other nucleic acid derivatives can be generated with codon usage optimized for expression in other organisms, such as yeasts, bacteria, and plants, where it is desired to engineer the expression of subject proteins by using specific codons chosen according to the preferred codons used in highly expressed genes in each organism.

Nucleic acids encoding the amino acid sequence of any od SEQ ID NOs:2, 4, 6, 8, 10, 12, or 14 or fragment or derivative thereof, may be obtained from an appropriate cDNA library prepared from any eukaryotic species that encodes subject proteins such as vertebrates, preferably mammalian (e.g. primate, porcine, bovine, feline, equine, and canine species, etc.) and invertebrates, such as arthropods, particularly insects species (preferably Drosophila), *acarids, crustacea, molluscs, nematodes,* and other worms. An expression library can be constructed using known methods. For example, mRNA can be isolated to make cDNA which is ligated into a suitable expression vector for expression in a host cell into which it is introduced. Various screening assays can then be used to select for the gene or gene product (e.g. oligonucleotides of at least about 20 to 80 bases designed to identify the gene of interest, or labeled antibodies that specifically bind to the gene product). The gene and/or gene product can then be recovered from the host cell using known techniques.

Polymerase chain reaction (PCR) can also be used to isolate nucleic acids of the subject gene where oligonucleotide primers representing fragmentary sequences of interest amplify RNA or DNA sequences from a source such as a genomic or cDNA library (as described by Sambrook et al., supra). Additionally, degenerate primers for amplifying homologs from any species of interest may be used. Once a PCR product of appropriate size and sequence is obtained, it may be cloned and sequenced by standard techniques, and utilized as a probe to isolate a complete cDNA or genomic clone.

Fragmentary sequences of subject nucleic acids and derivatives may be synthesized by known methods. For example, oligonucleotides may be synthesized using an automated DNA synthesizer available from commercial suppliers (e.g. Biosearch, Novato, Calif.; Perkin-Elmer Applied Biosystems, Foster City, Calif.). Antisense RNA sequences can be produced intracellularly by transcription from an exogenous sequence, e.g. from vectors that contain antisense subject nucleic acid sequences. Newly generated sequences may be identified and isolated using standard methods.

An isolated subject nucleic acid sequence can be inserted into any appropriate cloning vector, for example bacteriophages such as lambda derivatives, or plasmids such as PBR322, pUC plasmid derivatives and the Bluescript vector (Stratagene, San Diego, Calif.). Recombinant molecules can be introduced into host cells via transformation, transfection, infection, electroporation, etc., or into a transgenic animal such as a fly. The transformed cells can be cultured to generate large quantities of the subject nucleic acid. Suitable methods for isolating and producing the subject nucleic acid sequences are well-known in the art (Sambrook et al., supra; DNA Cloning: A Practical Approach, Vol. 1, 2, 3, 4, (1995) Glover, ed., MRL Press, Ltd., Oxford, U.K.).

The nucleotide sequence encoding a subject protein or fragment or derivative thereof, can be inserted into any appropriate expression vector for the transcription and translation of the inserted protein-coding sequence. Alternatively, the necessary transcriptional and translational signals can be supplied by the native subject gene and/or its flanking regions. A variety of host-vector systems may be utilized to express the protein-coding sequence such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, DNA, plasmid DNA, or cosmid DNA. Expression of a subject protein may be controlled by a suitable promoter/enhancer element. In addition, a host cell strain may be selected which modulates the expression of the inserted sequences, or modifies and processes the gene product in the specific fashion desired.

To detect expression of the subject gene product, the expression vector can comprise a promoter operably linked to a subject gene nucleic acid, one or more origins of replication, and, one or more selectable markers (e.g. thymidine kinase activity, resistance to antibiotics, etc.). Alternatively, recombinant expression vectors can be identified by assaying for the expression of the subject gene product based on the physical or functional properties of the subject protein in in vitro assay systems (e.g. immunoassays).

The subject protein, fragment, or derivative may be optionally expressed as a fusion, or chimeric protein product (i.e. it is joined via a peptide bond to a heterologous protein sequence of a different protein). A chimeric product can be made by ligating the appropriate nucleic acid sequences encoding the desired amino acid sequences to each other in the proper coding frame using standard methods and expressing the chimeric product. A chimeric product may also be made by protein synthetic techniques, e.g. by use of a peptide synthesizer.

Once a recombinant that expresses the subject gene sequence is identified, the gene product can be isolated and purified using standard methods (e.g. ion exchange, affinity, and gel exclusion chromatography; centrifugation; differential solubility; electrophoresis). The amino acid sequence of the protein can be deduced from the nucleotide sequence of the chimeric gene contained in the recombinant and can thus be synthesized by standard chemical methods (Hunkapiller et al., Nature (1984) 310:105–111). Alternatively, native subject proteins can be purified from natural sources, by standard methods (e.g. immmunoaffinity purification).

Proteins of the Invention

Subject proteins of the invention comprise or consist of an amino acid sequence of SEQ ID NOs:2, 4, 6, 8, 10, 12, or 14 or fragments or derivatives thereof. Compositions comprising these proteins may consist essentially of the subject proteins, fragments, or derivatives, or may comprise additional components (e.g. pharmaceutically acceptable carriers or excipients, culture media, etc.).

Subject protein derivatives typically share a certain degree of sequence identity or sequence similarity with SEQ ID NOs:2, 4, 6, 8, 10, 12, or 14, or a fragment thereof. As used herein, "percent (%) amino acid sequence identity" with respect to a subject sequence, or a specified portion of a subject sequence, is defined as the percentage of amino acids in the candidate derivative amino acid sequence identical with the amino acid in the subject sequence (or specified portion thereof), after aligning the sequences and introducing gaps, if necessary to achieve the maximum percent sequence identity, as generated by BLAST (Altschul et al., supra) using the same parameters discussed above for derivative nucleic acid sequences. A % amino acid sequence identity value is determined by the number of matching identical amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, cysteine, threonine, and glycine.

In one preferred embodiment, a subject protein derivative shares at least 80% sequence identity or similarity, preferably at least 85%, more preferably at least 90%, and most preferably at least 95% sequence identity or similarity with a contiguous stretch of at least 25 amino acids, preferably at least 50 amino acids, more preferably at least 100 amino acids, and in some cases, the entire length of SEQ ID NOs:2, 4, 6, 8, 10, 12, or 14.

The preferred dmBCL2 protein derivative may consist of or comprise a sequence that shares 100% similarity with any contiguous stretch of at least 12 amino acids, preferably at least 14 amino acids, more preferably at least 17 amino acids, and most preferably at least 22 amino acids of SEQ ID NO:2. Preferred fragments of dmBCL2 proteins consist or comprise at least 10, preferably at least 12, more preferably at least 15, and most preferably at least 20 contiguous amino acids of SEQ ID NO:2.

The preferred dmSURVIVIN protein derivative may consist of or comprise a sequence that shares 100% similarity with any contiguous stretch of at least 12 amino acids, preferably at least 14 amino acids, more preferably at least 17 amino acids, and most preferably at least 22 amino acids of SEQ ID NO:4. Preferred fragments of dmSURVIVIN proteins consist or comprise at least 7, preferably at least 9, more preferably at least 12, and most preferably at least 17 contiguous amino acids of SEQ ID NO:4.

The preferred dmGFRP protein derivative may consist of or comprise a sequence that shares 100% similarity with any contiguous stretch of at least 19 amino acids, preferably at least 21 amino acids, more preferably at least 24 amino acids, and most preferably at least 29 amino acids of SEQ ID NO:6. Preferred fragments of dmGFRP proteins consist or comprise at least 8, preferably at least 10, more preferably at least 13, and most preferably at least 18 contiguous amino acids of SEQ ID NO:6.

The preferred dmADAM protein derivative may consist of or comprise a sequence that shares 100% similarity with any contiguous stretch of at least 13 amino acids, preferably at least 15 amino acids, more preferably at least 18 amino acids, and most preferably at least 23 amino acids of SEQ ID NO:8. Preferred fragments of dmADAM proteins consist or comprise at least 11, preferably at least 13, more preferably at least 16, and most preferably at least 21 contiguous amino acids of SEQ ID NO:8.

The preferred dmMYB protein derivative may consist of or comprise a sequence that shares 100% similarity with any contiguous stretch of at least 10 amino acids, preferably at least 12 amino acids, more preferably at least 15 amino acids, and most preferably at least 20 amino acids of SEQ ID NO:10. Preferred fragments of dmMYB proteins consist or comprise at least 5, preferably at least 7, more preferably at least 10, and most preferably at least 15 contiguous amino acids of SEQ ID NO:10.

The preferred dmPI3K protein derivative may consist of or comprise a sequence that shares 100% similarity with any contiguous stretch of at least 38 amino acids, preferably at least 40 amino acids, more preferably at least 43 amino acids, and most preferably at least 48 amino acids of SEQ ID NO:12. Preferred fragments of dmPI3K proteins consist or comprise at least 22, preferably at least 24, more preferably at least 27, and most preferably at least 32 contiguous amino acids of SEQ ID NO1:2.

The preferred dmMCC protein derivative may consist of or comprise a sequence that shares 100% similarity with any contiguous stretch of at least 9 amino acids, preferably at least 11 amino acids, more preferably at least 14 amino acids, and most preferably at least 19 amino acids of SEQ ID NO:14. Preferred fragments of dmMCC proteins consist or comprise at least 7, preferably at least 9, more preferably at least 12, and most preferably at least 17 contiguous amino acids of SEQ ID NO:14.

The fragment or derivative of the subject protein is preferably "functionally active" meaning that the subject protein derivative or fragment exhibits one or more functional activities associated with a full-length, wild-type subject protein comprising the amino acid sequence of SEQ ID NOs:2, 4, 6, 8, 10, 12, or 14. As one example, a fragment or derivative may have antigenicity such that it can be used in immunoassays, for immunization, for inhibition of subject activity, etc, as discussed further below regarding generation of antibodies to subject proteins. Preferably, a functionally active subject fragment or derivative is one that displays one or more biological activities associated with subject proteins. The functional activity of subject proteins, derivatives and fragments can be assayed by various methods known to one skilled in the art (Current Protocols in Protein Science (1998) Coligan et al., eds., John Wiley & Sons, Inc., Somerset, N.J.). In a preferred method, which is described in detail below, a model organism, such as Drosophila, is used in genetic studies to assess the phenotypic effect of a fragment or derivative (i.e. a mutant subject protein).

Subject protein derivatives can be produced by various methods known in the art. The manipulations which result in their production can occur at the gene or protein level. For example, a cloned subject gene sequence can be cleaved at appropriate sites with restriction endonuclease(s) (Wells et al., Philos. Trans. R. Soc. London SerA (1986) 317:415), followed by further enzymatic modification if desired, isolated, and ligated in vitro, and expressed to produce the desired derivative. Alternatively, a subject gene can be mutated in vitro or in vivo, to create and/or destroy translation, initiation, and/or termination sequences, or to create variations in coding regions and/or to form new restriction endonuclease sites or destroy preexisting ones, to facilitate further in vitro modification. A variety of mutagenesis techniques are known in the art such as chemical mutagenesis, in vitro site-directed mutagenesis (Carter et al., Nucl. Acids Res. (1986) 13:4331), use of TAB® linkers (available from Pharmacia and Upjohn, Kalamazoo, Mich.), etc.

At the protein level, manipulations include post translational modification, e.g. glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known technique (e.g. specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.). Derivative proteins can also be chemically synthesized by use of a peptide synthesizer, for example to introduce nonclassical amino acids or chemical amino acid analogs as substitutions or additions into the subject protein sequence.

Chimeric or fusion proteins can be made comprising a subject protein or fragment thereof (preferably comprising one or more structural or functional domains of the subject protein) joined at its amino- or carboxy-terminus via a peptide bond to an amino acid sequence of a different protein. Chimeric proteins can be produced by any known method, including: recombinant expression of a nucleic acid encoding the protein (comprising a coding sequence of a subject protein joined in-frame to a coding sequence for a different protein); ligating the appropriate nucleic acid sequences encoding the desired amino acid sequences to each other in the proper coding frame, and expressing the chimeric product; and protein synthetic techniques, e.g. by use of a peptide synthesizer.

Subject Gene Regulatory Elements

Subject gene regulatory DNA elements, such as enhancers or promoters, can be used to identify tissues, cells, genes and factors that specifically control subject protein production.

dmBCL2 gene regulatory DNA elements reside within nucleotides 1 to 550. Preferably at least 20, more preferably at least 25, and most preferably at least 50 contiguous nucleotides within nucleotides 1 to 550 of SEQ ID NO:1 are used.

dmSURVIVIN gene regulatory DNA elements reside within nucleotides 1 to 60. Preferably at least 20, more preferably at least 25, and most preferably at least 50 contiguous nucleotides within nucleotides 1 to 60 of SEQ ID NO:3 are used.

dmGFRP gene regulatory DNA elements reside within nucleotides 1 to 500. Preferably at least 20, more preferably at least 25, and most preferably at least 50 contiguous nucleotides within nucleotides 1 to 500 of SEQ ID NO:5 are used.

dmADAM gene regulatory DNA elements reside within nucleotides 1 to 477. Preferably at least 20, more preferably at least 25, and most preferably at least 50 contiguous nucleotides within nucleotides 1 to 477 of SEQ ID NO:7 are used.

dmMYB gene regulatory DNA elements reside within nucleotides 1 to 59. Preferably at least 20, more preferably at least 25, and most preferably at least 50 contiguous nucleotides within nucleotides 1 to 59 of SEQ ID NO:9 are used.

dmMCC gene regulatory DNA elements reside within nucleotides 1 to 41. Preferably at least 20, more preferably at least 25, and most preferably at least 40 contiguous nucleotides within nucleotides 1 to 41 of SEQ ID NO:13 are used.

Analyzing components that are specific to subject protein function can lead to an understanding of how to manipulate these regulatory processes, especially therapeutic applications, as well as an understanding of how to diagnose dysfunction in these processes.

Gene fusions with the subject regulatory elements can be made. For compact genes that have relatively few and small intervening sequences, such as those described herein for Drosophila, it is typically the case that the regulatory elements that control spatial and temporal expression patterns are found in the DNA immediately upstream of the coding region, extending to the nearest neighboring gene. Regulatory regions can be used to construct gene fusions where the regulatory DNAs are operably fused to a coding region for a reporter protein whose expression is easily detected, and these constructs are introduced as transgenes into the animal of choice. An entire regulatory DNA region can be used, or the regulatory region can be divided into smaller segments to identify sub-elements that might be specific for controlling expression a given cell type or stage of development. Reporter proteins that can be used for construction of these gene fusions include *E. coli* beta-galactosidase and green fluorescent protein (GFP). These can be detected readily in situ, and thus are useful for histological studies and can be used to sort cells that express subject proteins (O'Kane and Gehring PNAS (1987) 84(24):9123–9127; Chalfie et al., Science (1994) 263:802–805; and Cumberledge and Krasnow (1994) Methods in Cell Biology 44:143–159). Recombinase proteins, such as FLP or cre, can be used in controlling gene expression through site-specific recombination (Golic and Lindquist (1989) Cell 59(3):499–509; White et al., Science (1996) 271:805–807). Toxic proteins such as the reaper and hid cell death proteins, are useful to specifically ablate cells that normally express subject proteins in order to assess the physiological function of the cells (Kingston, In Current Protocols in Molecular Biology (1998) Ausubel et al., John Wiley & Sons, Inc. sections 12.0.3–12.10) or any other protein where it is desired to examine the function this particular protein specifically in cells that synthesize subject proteins.

Alternatively, a binary reporter system can be used, similar to that described further below, where the subject gene regulatory element is operably fused to the coding region of an exogenous transcriptional activator protein, such as the GAL4 or tTA activators described below, to create a subject gene regulatory element "driver gene". For the other half of the binary system the exogenous activator controls a separate "target gene" containing a coding region of a reporter protein operably fused to a cognate regulatory element for the exogenous activator protein, such as $UAS_G$ or a tTA-response element, respectively. An advantage of a binary system is that a single driver gene construct can be used to activate transcription from preconstructed target genes encoding different reporter proteins, each with its own uses as delineated above.

Subject gene regulatory element-reporter gene fusions are also useful for tests of genetic interactions, where the objective is to identify those genes that have a specific role in controlling the expression of subject genes, or promoting the growth and differentiation of the tissues that expresses the subject protein. Subject gene regulatory DNA elements are also useful in protein-DNA binding assays to identify gene regulatory proteins that control the expression of subject genes. The gene regulatory proteins can be detected using a variety of methods that probe specific protein-DNA interactions well known to those skilled in the art (Kingston, supra) including in vivo footprinting assays based on protection of DNA sequences from chemical and enzymatic modification within living or permeabilized cells; and in vitro footprinting assays based on protection of DNA sequences from chemical or enzymatic modification using protein extracts, nitrocellulose filter-binding assays and gel electrophoresis mobility shift assays using radioactively labeled regulatory DNA elements mixed with protein extracts. Candidate subject gene regulatory proteins can be purified using a combination of conventional and DNA-affinity purification techniques. Molecular cloning strategies can also be used to identify proteins that specifically bind subject gene regulatory DNA elements. For example, a Drosophila cDNA library in an expression vector, can be screened for cDNAs that encode subject gene regulatory element DNA-binding activity. Similarly, the yeast "one-hybrid" system can be used (Li and Herskowitz, Science (1993) 262:1870–1874; Luo et al., Biotechniques (1996) 20(4):564–568; Vidal et al., PNAS (1996) 93(19): 10315–10320).

Identification of Molecules that Interact with Subject Proteins

A variety of methods can be used to identify or screen for molecules, such as proteins or other molecules, that interact with subject proteins, or derivatives or fragments thereof. The assays may employ purified subject proteins, or cell lines or model organisms such as Drosophila and *C. elegans*, that have been genetically engineered to express subject proteins. Suitable screening methodologies are well known in the art to test for proteins and other molecules that interact with subject genes and proteins (see e.g., PCT International Publication No. WO 96/34099). The newly identified interacting molecules may provide new targets for pharmaceutical agents. Any of a variety of exogenous molecules, both naturally occurring and/or synthetic (e.g., libraries of small molecules or peptides, or phage display libraries), may be screened for binding capacity. In a typical binding experiment, the subject protein or fragment is mixed with candidate molecules under conditions conducive to binding, sufficient time is allowed for any binding to occur, and assays are performed to test for bound complexes. Assays to find interacting proteins can be performed by any method known in the art, for example, immunoprecipitation with an antibody that binds to the protein in a complex followed by analysis by size fractionation of the immunoprecipitated proteins (e.g. by denaturing or nondenaturing polyacrylamide gel electrophoresis), Western analysis, non-denaturing gel electrophoresis, etc.

Two-hybrid Assay Systems

A preferred method for identifying interacting proteins is a two-hybrid assay system or variation thereof (Fields and Song, Nature (1989) 340:245–246; U.S. Pat. No. 5,283,173; for review see Brent and Finley, Annu. Rev. Genet. (1997) 31:663–704). The most commonly used two-hybrid screen system is performed using yeast. All systems share three elements: 1) a gene that directs the synthesis of a "bait" protein fused to a DNA binding domain; 2) one or more "reporter" genes having an upstream binding site for the bait, and 3) a gene that directs the synthesis of a "prey" protein fused to an activation domain that activates transcription of the reporter gene. For the screening of proteins that interact with subject protein, the "bait" is preferably a subject protein, expressed as a fusion protein to a DNA binding domain; and the "prey" protein is a protein to be tested for ability to interact with the bait, and is expressed as a fusion protein to a transcription activation domain. The prey proteins can be obtained from recombinant biological libraries expressing random peptides.

The bait fusion protein can be constructed using any suitable DNA binding domain, such as the E. coli LexA repressor protein, or the yeast GAL4 protein (Bartel et al., BioTechniques (1993) 14:920–924, Chasman et al., Mol. Cell. Biol. (1989) 9:4746–4749; Ma et al., Cell (1987) 48:847–853; Ptashne et al., Nature (1990) 346:329–331).

The prey fusion protein can be constructed using any suitable activation domain such as GAL4, VP-16, etc. The preys may contain useful moieties such as nuclear localization signals (Ylikomi et al., EMBO J. (1992) 11:3681–3694; Dingwall and Laskey, Trends Biochem. Sci. Trends Biochem. Sci. (1991) 16:479–481) or epitope tags (Allen et al., Trends Biochem. Sci. Trends Biochem. Sci. (1995) 20:511–516) to facilitate isolation of the encoded proteins.

Any reporter gene can be used that has a detectable phenotype such as reporter genes that allow cells expressing them to be selected by growth on appropriate medium (e.g. HIS3, LEU2 described by Chien et al., PNAS (1991) 88:9572–9582; and Gyuris et al., Cell (1993) 75:791–803). Other reporter genes, such as LacZ and GFP, allow cells expressing them to be visually screened (Chien et al., supra).

Although the preferred host for two-hybrid screening is the yeast, the host cell in which the interaction assay and transcription of the reporter gene occurs can be any cell, such as mammalian (e.g. monkey, mouse, rat, human, bovine), chicken, bacterial, or insect cells. Various vectors and host strains for expression of the two fusion protein populations in yeast can be used (U.S. Pat. No. 5,468,614; Bartel et al., Cellular Interactions in Development (1993) Hartley, ed., Practical Approach Series xviii, IRL Press at Oxford University Press, New York, N.Y., pp. 153–179; and Fields and Sternglanz, Trends In Genetics (1994) 10:286–292). As an example of a mammalian system, interaction of activation tagged VP16 derivatives with a GAL4-derived bait drives expression of reporters that direct the synthesis of hygromycin B phosphotransferase, chloramphenicol acetyltransferase, or CD4 cell surface antigen (Fearon et al., PNAS (1992) 89:7958–7962). As another example, interaction of VP16-tagged derivatives with GAL4-derived baits drives the synthesis of SV40 T antigen, which in turn promotes the replication of the prey plasmid, which carries an SV40 origin (Vasavada et al., PNAS (1991) 88:10686–10690).

Typically, the bait subject gene and the prey library of chimeric genes are combined by mating the two yeast strains on solid or liquid media for a period of approximately 6–8 hours. The resulting diploids contain both kinds of chimeric genes, i.e., the DNA-binding domain fusion and the activation domain fusion.

Transcription of the reporter gene can be detected by a linked replication assay in the case of SV40 T antigen (described by Vasavada et al., supra) or using immunoassay methods, preferably as described in Alam and Cook (Anal. Biochem. (1990)188:245–254). The activation of other reporter genes like URA3, HIS3, LYS2, or LEU2 enables the cells to grow in the absence of uracil, histidine, lysine, or leucine, respectively, and hence serves as a selectable marker. Other types of reporters are monitored by measuring a detectable signal. For example, GFP and lacZ have gene products that are fluorescent and chromogenic, respectively.

After interacting proteins have been identified, the DNA sequences encoding the proteins can be isolated. In one method, the activation domain sequences or DNA-binding domain sequences (depending on the prey hybrid used) are amplified, for example, by PCR using pairs of oligonucleotide primers specific for the coding region of the DNA binding domain or activation domain. Other known amplification methods can be used, such as ligase chain reaction, use of Q replicase, or various other methods described (see Kricka et al., Molecular Probing, Blotting, and Sequencing (1995) Academic Press, New York, Chapter 1 and Table IX).

If a shuttle (yeast to E. coli) vector is used to express the fusion proteins, the DNA sequences encoding the proteins can be isolated by transformation of E. coli using the yeast DNA and recovering the plasmids from E. coli. Alternatively, the yeast vector can be isolated, and the insert encoding the fusion protein subcloned into a bacterial expression vector, for growth of the plasmid in E. coli.

A limitation of the two-hybrid system occurs when transmembrane portions of proteins in the bait or the prey fusions are used. This occurs because most two-hybrid systems are designed to function by formation of a functional transcription activator complex within the nucleus, and use of transmembrane portions of the protein can interfere with proper association, folding, and nuclear transport of bait or prey segments (Ausubel et al., supra; Allen et al., supra). Since the subject protein is a transmembrane protein, it is preferred that intracellular or extracellular domains be used for bait in a two-hybrid scheme.

Antibodies and Immunoassays

Subject proteins encoded by SEQ ID NOs:2, 4, 6, 8, 10, 12, or 14 and derivatives and fragments thereof, such as those discussed above, may be used as an immunogen to generate monoclonal or polyclonal antibodies and antibody fragments or derivatives (e.g. chimeric, single chain, Fab fragments). For example, fragments of a subject protein, preferably those identified as hydrophilic, are used as immunogens for antibody production using art-known methods such as by hybridomas; production of monoclonal antibodies in germ-free animals (PCT/US90/02545); the use of human hybridomas (Cole et al., PNAS (1983) 80:2026–2030; Cole et al., in Monoclonal Antibodies and Cancer Therapy (1985) Alan R. Liss, pp. 77–96), and production of humanized antibodies (Jones et al., Nature (1986) 321:522–525; U.S. Pat. No. 5,530,101). In a particular embodiment, subject polypeptide fragments provide specific antigens and/or immunogens, especially when coupled to carrier proteins. For example, peptides are covalently coupled to keyhole limpet antigen (KLH) and the conjugate is emulsified in Freund's complete adjuvant. Laboratory rabbits are immunized according to conventional protocol and bled. The presence of specific antibodies is assayed by solid phase immunosorbent assays using immobilized corresponding polypeptide. Specific activity or function of the antibodies produced may be determined by convenient in vitro, cell-based, or in vivo assays: e.g. in vitro binding assays, etc. Binding affinity may be assayed by determination of equilibrium constants of antigen-antibody association (usually at least about $10^7$ $M^{-1}$, preferably at least about $10^8$ $M^{-1}$, more preferably at least about $10^9$ $M^{-1}$).

Immunoassays can be used to identify proteins that interact with or bind to subject proteins. Various assays are available for testing the ability of a protein to bind to or compete with binding to a wild-type subject protein or for binding to an anti-subject protein antibody. Suitable assays include radioimmunoassays, ELISA (enzyme linked immunosorbent assay), immunoradiometric assays, gel diffusion precipitin reactions, immunodiffusion assays, in situ immunoassays (e.g., using colloidal gold, enzyme or radioisotope labels), western blots, precipitation reactions, agglutination assays (e.g., gel agglutination assays, hemagglutination assays), complement fixation assays, immunofluorescence assays, protein A assays, immunoelectrophoresis assays, etc.

Identification of Potential Drug Targets

Once new subject genes or subject interacting genes are identified, they can be assessed as potential drug targets.

Putative drugs and and molecules can be applied onto whole insects, nematodes, and other small invertebrate metazoans, and the ability of the compounds to modulate (e.g. block or enhance) subject activity can be observed. Alternatively, the effect of various compounds on subject s can be assayed using cells that have been engineered to express one or more subject s and associated proteins.

Assays of Compounds on Worms

In a typical worm assay, the compounds to be tested are dissolved in DMSO or other organic solvent, mixed with a bacterial suspension at various test concentrations, preferably OP50 strain of bacteria (Brenner, Genetics (1974) 110:421–440), and supplied as food to the worms. The population of worms to be treated can be synchronized larvae (Sulston and Hodgkin, in The nematode *C. elegans* (1988), supra) or adults or a mixed-stage population of animals.

Adult and larval worms are treated with different concentrations of compounds, typically ranging from 1 mg/ml to 0.001 mg/ml. Behavioral aberrations, such as a decrease in motility and growth, and morphological aberrations, sterility, and death are examined in both acutely and chronically treated adult and larval worms. For the acute assay, larval and adult worms are examined immediately after application of the compound and re-examined periodically (every 30 minutes) for 5–6 hours. Chronic or long-term assays are performed on worms and the behavior of the treated worms is examined every 8–12 hours for 4–5 days. In some circumstances, it is necessary to reapply the compound to the treated worms every 24 hours for maximal effect.

Assays of Compounds on Insects

Potential insecticidal compounds can be administered to insects in a variety of ways, including orally (including addition to synthetic diet, application to plants or prey to be consumed by the test organism), topically (including spraying, direct application of compound to animal, allowing animal to contact a treated surface), or by injection. Insecticides are typically very hydrophobic molecules and must commonly be dissolved in organic solvents, which are allowed to evaporate in the case of methanol or acetone, or at low concentrations can be included to facilitate uptake (ethanol, dimethyl sulfoxide).

The first step in an insect assay is usually the determination of the minimal lethal dose (MLD) on the insects after a chronic exposure to the compounds. The compounds are usually diluted in DMSO, and applied to the food surface bearing 0–48 hour old embryos and larvae. In addition to MLD, this step allows the determination of the fraction of eggs that hatch, behavior of the larvae, such as how they move/feed compared to untreated larvae, the fraction that survive to pupate, and the fraction that eclose (emergence of the adult insect from puparium). Based on these results more detailed assays with shorter exposure times may be designed, and larvae might be dissected to look for obvious morphological defects. Once the MLD is determined, more specific acute and chronic assays can be designed.

In a typical acute assay, compounds are applied to the food surface for embryos, larvae, or adults, and the animals are observed after 2 hours and after an overnight incubation. For application on embryos, defects in development and the percent that survive to adulthood are determined. For larvae, defects in behavior, locomotion, and molting may be observed. For application on adults, behavior and neurological defects are observed, and effects on fertility are noted.

For a chronic exposure assay, adults are placed on vials containing the compounds for 48 hours, then transferred to a clean container and observed for fertility, neurological defects, and death.

Assay of Compounds Using Cell Cultures

Compounds that modulate (e.g. block or enhance) subject gene activity may also be assayed using cell culture. For example, various compounds added to cells expressing subject may be screened for their ability to modulate the activity of subject genes. Assays for changes in subject gene functions can be performed on cultured cells expressing endogenous normal or mutant subject genes. Such studies also can be performed on cells transfected with vectors capable of expressing the subject genes, or functional domains of one of the subject genes, in normal or mutant form. In addition, to enhance the signal measured in such assays, cells may be cotransfected with genes encoding subject proteins.

As an example, various compounds added to cells expressing dmBCL2 or dmSURVIVIN may be screened for their ability to modulate the activity of dmBCL2 or dmSURVIVIN genes based upon measurements of apoptosis. For example, cells might be transfected with normal or mutant dmBCL2 or dmSURVIVIN, and grown in presence of various compounds. Effect of compounds on cell survival may be measured by terminal deoxynucleotidyltransferase-mediated dUTP nick end labeling (TUNEL) assay (Gorczyca W., et al., 1998, 91:217–238).

As another example, various compounds added to cells expressing dmGFRP may be screened for their ability to modulate the activity of dmGFRP genes based upon measurements of cell growth and proliferation. For example, cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79). Cell Proliferation may also be examined using [$^3$H]-thymidine incorporation (Chen, J., 1996, Oncogene 13:1395–403; Jeoung, J., 1995, J. Biol. Chem. 270:18367–73). This assay allows for quantitative characterization of S-phase DNA syntheses. In this assay, cells synthesizing DNA will incorporate[$^3$H]-thymidine into newly synthesized DNA. Incorporation can then bemeasured by standard techniques such as by counting of radioisotope in a scintillation counter (e.g., Beckman LS 3800 Liquid Scintillation Counter).

As another example, various compounds added to cells expressing dmADAM may be screened for their ability to modulate the activity of dmADAM genes based upon measurements of protease activity. For example, $\alpha_2$-macroglobulin ($\alpha_2$-M) complex formation assay (Nagase H., et al., Ann. N.Y. Acad Sci. 1994 732:294–302; Feinman R D Ann. N.Y. Acad Sci. 1994 737:245–266) is performed using purified dmADAM protein on $\alpha_2$-M in presence or absence of compounds.

As another example, various compounds added to cells expressing dmMYB may be screened for their ability to modulate the activity of dmMYB genes based upon measurements of DNA binding and transcriptional activity. For example, Binding of dmMYB gene to a specific nucleotide sequence, or DNA sequence, may be examined by Electrophoretic Mobility Shift Assay (see e.g., Oncogene. 1998 Mar 5;16(9):1171–81; Sambrook et al., supra; Glover, supra). Briefly, in Electrophoretic Mobility Shift Assay, complementary, single-stranded oligonucleotides are synthesized and hybridized to a final concentration of 10–15 $\mu g/\mu l$. Double stranded DNA is verified by gel electrophoretic analysis (e.g., on a 7% polyacrylamide gel, by methods known in the art), and end labeled with 20 $\mu$Ci [32P] $\gamma$-dATP. Preparations of Drosophila nuclear extracts for use in mobility shift assays may be done as described in Dignam et al., 1983, Nucleic Acids Res. 11:1475–1489. For binding reactions involving competition, compounds are also added to the reaction mixture (e.g., 5–1000 ng). Resulting binding products are then analyzed by polyacrylamide gel electrophoresis. Gels are then dried and visualized by exposure to film (e.g., Kodak X-OMAT R X-ray film).

As another example, various compounds added to cells expressing dmPI3K may be screened for their ability to modulate the activity of dmPI3K genes based upon measurements of kinase activity. For example, cell lysates of cells transfected with wild-type or mutant dmPI3K are precipitated with anti-dmPI3K antibodies, and washed immunoprecipitates are subjected to in vitro kinase assay in presence or absence of compounds.

Compounds that selectively modulate the subject genes are identified as potential drug candidates having subject gene specificity.

Identification of small molecules and compounds as potential pharmaceutical compounds from large chemical libraries requires high-throughput screening (HTS) methods (Bolger, Drug Discovery Today (1999) 4:251–253). Several of the assays mentioned herein can lend themselves to such screening methods. For example, cells or cell lines expressing wild type or mutant subject proteins or their fragments, and a reporter gene can be subjected to compounds of interest, and depending on the reporter genes, interactions can be measured using a variety of methods such as color detection, fluorescence detection (e.g. GFP), autoradiography, scintillation analysis, etc.

Generation and Genetic Analysis of Animals and Cell Lines with Altered Expression of Subject Genes Both genetically modified animal models (i.e. in vivo models), such as *C. elegans* and Drosophila, and in vitro models such as genetically engineered cell lines expressing or mis-expressing subject pathway genes, are useful for the functional analysis of these proteins. Model systems that display detectable phenotypes, can be used for the identification and characterization of subject pathway genes or other genes of interest and/or phenotypes associated with the mutation or mis-expression of subject pathway protein. The term "mis-expression" as used herein encompasses mis-expression due to gene mutations. Thus, a mis-expressed subject pathway protein may be one having an amino acid sequence that differs from wild-type (i.e. it is a derivative of the normal protein). A mis-expressed subject pathway protein may also be one in which one or more amino acids have been deleted, and thus is a "fragment" of the normal protein. As used herein, "mis-expression" also includes ectopic expression (e.g. by altering the normal spatial or temporal expression), over-expression (e.g. by multiple gene copies), underexpression, non-expression (e.g. by gene knockout or blocking expression that would otherwise normally occur), and further, expression in ectopic tissues. As used in the following discussion concerning in vivo and in vitro models, the term "gene of interest" refers to a subject pathway gene, or any other gene involved in regulation or modulation, or downstream effector of the subject pathway.

The in vivo and in vitro models may be genetically engineered or modified so that they 1) have deletions and/or insertions of one or more subject pathway genes, 2) harbor interfering RNA sequences derived from subject pathway genes, 3) have had one or more endogenous subject pathway genes mutated (e.g. contain deletions, insertions, rearrangements, or point mutations in subject gene or other genes in the pathway), and/or 4) contain transgenes for mis-expression of wild-type or mutant forms of such genes. Such genetically modified in vivo and in vitro models are useful for identification of genes and proteins that are involved in the synthesis, activation, control, etc. of subject pathway gene and/or gene products, and also downstream effectors of subject gene function, genes regulated by subject, etc. The model systems can be used for testing potential pharmaceutical compounds that interact with the subject pathway, for example by administering the compound to the model system using any suitable method (e.g. direct contact, ingestion, injection, etc.) and observing any changes in phenotype, for example defective movement, lethality, etc. Various genetic engineering and expression modification methods which can be used are well-known in the art, including chemical mutagenesis, transposon mutagenesis, antisense RNAi, dsRNAi, and transgene-mediated mis-expression.

Generating Loss-of-function Mutations by Mutagenesis

Loss-of-function mutations in an invertebrate metazoan subject gene can be generated by any of several mutagenesis methods known in the art (Ashburner, In *Drosophila melanogaster:* A Laboratory Manual (1989), Cold Spring Harbor, N.Y., Cold Spring Harbor Laboratory Press: pp. 299–418; Fly pushing: The Theory and Practice of *Drosophila melanogaster* Genetics (1997) Cold Spring Harbor Press, Plainview, N.Y.; The nematode *C. elegans* (1988) Wood, Ed., Cold Spring Harbor Laboratory Press, Cold Spring harbor, N.Y.). Techniques for producing mutations in a gene or genome include use of radiation (.e.g., X-ray, UV, or gamma ray); chemicals (e.g., EMS, MMS, ENU, formaldehyde, etc.); and insertional mutagenesis by mobile elements including dysgenesis induced by transposon insertions, or transposon-mediated deletions, for example, male recombination, as described below. Other methods of altering expression of genes include use of transposons (e.g., P element, EP-type "overexpression trap" element, mariner element, piggyBac transposon, hermes, minos, sleeping beauty, etc.) to misexpress genes; gene targeting by homologous recombination; antisense; double-stranded RNA interference; peptide and RNA aptamers; directed deletions; homologous recombination; dominant negative alleles; and intrabodies.

Transposon insertions lying adjacent to a gene of interest can be used to generate deletions of flanking genomic DNA, which if induced in the germline, are stably propagated in subsequent generations. The utility of this technique in generating deletions has been demonstrated and is well-known in the art. One version of the technique using collections of P element transposon induced recessive lethal mutations (P lethals) is particularly suitable for rapid identification of novel, essential genes in Drosophila (Cooley et al., Science (1988) 239:1121–1128; Spralding et al., PNAS (1995) 92:0824–10830). Since the sequence of the P elements are known, the genomic sequence flanking each transposon insert is determined either by plasmid rescue (Hamilton et al., PNAS (1991) 88:2731–2735) or by inverse polymerase chain reaction (Rehm,).

A more recent version of the transposon insertion technique in male Drosophila using P elements is known as P-mediated male recombination (Preston and Engels, Genetics (1996) 144:1611–1638).

Gene targeting approaches using homologous recombination have proven to be successful in Drosophila (Rong and Golic, Science (2000) 288:2013–20018) and potentially provide a general method of generating directed mutations in any gene-of-interest. This method uses broken-ended extrachromosomal DNA, created in vivo, to produce homology-directed changes in a target locus. First, a "targeting construct" is designed for the gene-of-interest which allows the replacement of the normal endogenous gene with a specifically designed mutation, such as a deletion, insertion or point mutation, via homologous recombination. The targeting construct is typically carried in an appropriate transposon-mediated transgenesis vector (e.g. P element-, piggyBac-, hermes-, minos-, or mariner-based vectors) which inserts the targeting construct randomly within the genome of the organism. The targeting construct is converted to a recombinogenic extrachromosomal form by inducing the expression of separate transgenes encoding a site-specific recombinase (e.g. FLP, cre, Kw, etc.) which excises the targeting construct, and a rare-cutting site-specific endonuclease (e.g. Scel, Crel, HO, etc.) which generates recombinogenic ends that direct homologous recombination and gene replacement of the endogenous locus. Though this method has only been shown to work in Dros, it has application to worms, other animals, plants, algae etc.

Generating Loss-of-function Phenotypes Using RNA-based Methods

Subject genes may be identified and/or characterized by generating loss-of-function phenotypes in animals of interest through RNA-based methods, such as antisense RNA (Schubiger and Edgar, Methods in Cell Biology (1994) 44:697–713). One form of the antisense RNA method involves the injection of embryos with an antisense RNA that is partially homologous to the gene of interest (in this case the subject gene). Another form of the antisense RNA method involves expression of an antisense RNA partially homologous to the gene of interest by operably joining a portion of the gene of interest in the antisense orientation to a powerful promoter that can drive the expression of large quantities of antisense RNA, either generally throughout the animal or in specific tissues. Antisense RNA-generated loss-of-function phenotypes have been reported previously for several Drosophila genes including cactus, pecanex, and Krüppel (LaBonne et al., Dev. Biol. (1989) 136(1):1–16; Schuh and Jackle, Genome (1989) 31(1):422–425; Geisler et al., Cell (1992) 71(4):613–621).

Loss-of-function phenotypes can also be generated by cosuppression methods (Bingham Cell (1997) 90(3):385–387; Smyth, Curr. Biol. (1997) 7(12):793–795; Que and Jorgensen, Dev. Genet. (1998) 22(1):100–109). Cosuppression is a phenomenon of reduced gene expression produced by expression or injection of a sense strand RNA corresponding to a partial segment of the gene of interest. Cosuppression effects have been employed extensively in plants and *C. elegans* to generate loss-of-function phenotypes, and there is a single report of cosuppression in Drosophila, where reduced expression of the Adh gene was induced from a white-Adh transgene using cosuppression methods (Pal-Bhadra et al., Cell (1997) 90(3):479–490).

Another method for generating loss-of-function phenotypes is by double-stranded RNA interference (dsRNAi). This method is based on the interfering properties of double-stranded RNA derived from the coding regions of gene, and has proven to be of great utility in genetic studies of *C. elegans* (Fire et al., Nature (1998) 391:806–811), and can also be used to generate loss-of-function phenotypes in Drosophila (Kennerdell and Carthew, Cell (1998) 95:1017–1026; Misquitta and Patterson PNAS (1999) 96:1451–1456). In one example of this method, complementary sense and antisense RNAs derived from a substantial portion of a gene of interest, such as subject gene, are synthesized in vitro. The resulting sense and antisense RNAs are annealed in an injection buffer, and the double-stranded RNA injected or otherwise introduced into animals (such as in their food or by soaking in the buffer containing the RNA). Progeny of the injected animals are then inspected for phenotypes of interest (PCT publication no. WO99/32619). In another embodiment of the method, the dsRNA can be delivered to the animal by bathing the animal in a solution containg a sufficient concentration of the dsRNA. In another embodiment of the method, dsRNA derived from subject genes can be generated in vivo by simultaneous expression of both sense and antisense RNA from appropriately positioned promoters operably fused to subject sequences in both sense and antisense orientations. In yet another embodiment of the method the dsRNA can be delivered to the animal by engineering expression of dsRNA within cells of a second organism that serves as food for the animal, for example engineering expression of dsRNA in *E. coli* bacteria which are fed to *C. elegans*, or engineering expression of dsRNA in baker's yeast which are fed to Drosophila, or engineering expression of dsRNA in transgenic plants which are fed to plant eating insects such as Leptinotarsa or Heliothis.

Recently, RNAi has been successfully used in cultured Drosophila cells to inhibit expression of targeted proteins (Dixon lab, University of Michigan, Caplen et al., Gene. (2000) 252(1–2):95–105). Thus, cell lines in culture can be manipulated using RNAi both to perturb and study the function of subject pathway components and to validate the efficacy of therapeutic strategies that involve the manipulation of this pathway.

Generating Loss-of-function Phenotypes Using Peptide and RNA Aptamers

Another method for generating loss-of-function phenotypes is by the use of peptide aptamers, which are peptides or small polypeptides that act as dominant inhibitors of protein function. Peptide aptamers specifically bind to target proteins, blocking their function ability (Kolonin and Finley, PNAS (1998) 95:14266–14271). Due to the highly selective nature of peptide aptamers, they may be used not only to target a specific protein, but also to target specific functions of a given protein. Further, peptide aptamers may be expressed in a controlled fashion by use of promoters that regulate expression in a temporal, spatial or inducible manner. Peptide aptamers act dominantly; therefore, they can be used to analyze proteins for which loss-of-function mutants are not available.

Peptide aptamers that bind with high affinity and specificity to a target protein may be isolated by a variety of techniques known in the art. In one method, they are isolated from random peptide libraries by yeast two-hybrid screens (Xu et al., PNAS (1997) 94:12473–12478). They can also be isolated from phage libraries (Hoogenboom et al., Immunotechnology (1998) 4:1–20) or chemically generated peptides/libraries.

RNA aptamers are specific RNA ligands for proteins, that can specifically inhibit protein function of the gene (Good et al., Gene Therapy (1997) 4:45–54; Ellington. et al., Biotechnol. Annu. Rev. (1995) 1:185–214). In vitro selection methods can be used to identify RNA aptamers having a selected specificity (Bell et al., J. Biol. Chem. (1998) 273:14309–14314). It has been demo nstrated that RNA aptamers can inhibit protein function in Drosophila (Shi et al., Proc. Natl. Acad. Sci USA (19999) 96:10033–10038). Accordingly, RNA aptamers can be used to decrease the expression of subject protein or derivative thereof, or a protein that interacts with the subject protein.

Transgenic an imals can be generated to test peptide or RNA aptamers in vivo (Kolonin, M G, and Finley, R L, Genetics (1998) 95:4266–4271). For example, transgenic Drosophila lines expressing the desired aptamers may be generated by P element mediated transformation (discussed below). The phenotypes of the progeny expressing the aptamers can then be characterized.

Generating Loss of Function Phenotypes Using Intrabodies

Intracellularly expressed antibodies, or intrabodies, are single-chain antibody molecules designed to specifically bind and inactivate target molecules inside cells. Intrabodies have been used in cell assays and in whole organisms such as Drosophila (Chen et al., Hum. Gen. Ther. (1994) 5:595–601; Hassanzadeh et al., Febs Lett. (1998) 16(1, 2):75–80 and 81–86). Inducible expression vectors can be constructed with intrabodies that react specifically with subject protein. These vectors can be introduced into model organisms and studied in the same manner as described above for aptamers.

Transgenesis

Typically, transgenic animals are created that contain gene fusions of the coding regions of the subject gene (from either genomic DNA or cDNA) or genes engineered to encode antisense RNAs, cosuppression RNAs, interfering dsRNA, RNA aptamers, peptide aptamers, or intrabodies operably joined to a specific promoter and transcriptional enhancer whose regulation has been well characterized, preferably heterologous promoters/enhancers (i.e. promoters/enhancers that are non-native to the subject pathway genes being expressed).

Methods are well known for incorporating exogenous nucleic acid sequences into the genome of animals or cultured cells to create transgenic animals or recombinant cell lines. For invertebrate animal models, the most common methods involve the use of transposable elements. There are several suitable transposable elements that can be used to incorporate nucleic acid sequences into the genome of model organisms. Transposable elements are particularly useful for inserting sequences into a gene of interest so that the encoded protein is not properly expressed, creating a "knock-out" animal having a loss-of-function phenotype. Techniques are well-established for the use of P element in Drosophila (Rubin and Spradling, Science (1982) 218:348–53; U.S. Pat. No. 4,670,388) and Tc1 in *C. elegans* (Zwaal et al., Proc. Natl. Acad. Sci. U.S.A. (1993) 90:7431–7435; and *Caenorhabditis elegans:* Modern Biological Analysis of an Organism (1995) Epstein and Shakes, Eds.). Other Tc1-like transposable elements can be used such as minos, mariner and sleeping beauty. Additionally, transposable elements that function in a variety of species, have been identified, such as PiggyBac (Thibault et al., Insect Mol Biol (1999) 8(1):119–23), hobo, and hermes.

P elements, or marked P elements, are preferred for the isolation of loss-of-function mutations in Drosophila subject genes because of the precise molecular mapping of these genes, depending on the availability and proximity of pre-existing P element insertions for use as a localized transposon source (Hamilton and Zinn, Methods in Cell Biology (1994) 44:81–94; and Wolfner and Goldberg, Methods in Cell Biology (1994) 44:33–80). Typically, modified P elements are used which contain one or more elements that allow detection of animals containing the P element. Most often, marker genes are used that affect the eye color of Drosophila, such as derivatives of the Drosophila white or rosy genes (Rubin and Spradling, Science (1982) 218(4570):348–353; and Klemenz et al., Nucleic Acids Res. (1987) 15(10):3947–3959). However, in principle, any gene can be used as a marker that causes a reliable and easily scored phenotypic change in transgenic animals. Various other markers include bacterial plasmid sequences having selectable markers such as ampicillin resistance (Steller and Pirrotta, EMBO. J. (1985) 4:167–171); and lacZ sequences fused to a weak general promoter to detect the presence of enhancers with a developmental expression pattern of interest (Bellen et al., Genes Dev. (1989) 3(9):1288–1300). Other examples of marked P elements useful for mutagenesis have been reported (Nucleic Acids Research (1998) 26:85–88;).

A preferred method of transposon mutagenesis in Drosophila employs the "local hopping" method described by Tower et al. (Genetics (1993) 133:347–359). Each new P insertion line can be tested molecularly for transposition of the P element into the gene of interest (e.g. any of subject genes) by assays based on PCR. For each reaction, one PCR primer is used that is homologous to sequences contained within the P element and a second primer is homologous to the coding region or flanking regions of the gene of interest. Products of the PCR reactions are detected by agarose gel electrophoresis. The sizes of the resulting DNA fragments reveal the site of P element insertion relative to the gene of interest. Alternatively, Southern blotting and restriction mapping using DNA probes derived from genomic DNA or cDNAs of the gene of interest can be used to detect transposition events that rearrange the genomic DNA of the gene. P transposition events that map to the gene of interest can be assessed for phenotypic effects in heterozygous or homozygous mutant Drosophila.

In another embodiment, Drosophila lines carrying P insertions in the gene of interest, can be used to generate localized deletions using known methods (Kaiser, Bioassays (1990) 12(6):297–301; Harnessing the power of Drosophila genetics, In *Drosophila melanogaster:* Practical Uses in Cell and Molecular Biology, Goldstein and Fyrberg, Eds., Academic Press, Inc. San Diego, Calif.). This is particularly useful if no P element transpositions are found that disrupt the gene of interest. Briefly, flies containing P elements inserted near the gene of interest are exposed to a further round of transposase to induce excision of the element. Progeny in which the transposon has excised are typically identified by loss of the eye color marker associated with the transposable element. The resulting progeny will include flies with either precise or imprecise excision of the P element, where the imprecise excision events often result in deletion of genomic DNA neighboring the site of P insertion. Such progeny are screened by molecular techniques to identify deletion events that remove genomic sequence from the gene of interest, and assessed for phenotypic effects in heterozygous and homozygous mutant Drosophila.

Recently a transgenesis system has been described that may have universal applicability in all eye-bearing animals and which has been proven effective in delivering transgenes to diverse insect species (Berghammer et al., Nature (1999) 402:370–371). This system includes: an artificial promoter active in eye tissue of all animal species, preferably containing three Pax6.binding sites positioned upstream of a TATA box (3×P3; Sheng et al., Genes Devel. (1997) 11:1122–1131); a strong and visually detectable marker gene, such as GFP or other autofluorescent protein genes (Pasher et al., Gene (1992) 111:229–233; U.S. Pat. No 5,491,084); and promiscuous vectors capable of delivering transgenes to a broad range of animal species. Examples of promiscuous vectors include transposon-based vectors derived from Hermes, PiggyBac, or mariner, and vectors based on pantropic $VSV_G$-pseudotyped retroviruses (Burns et al., In Vitro Cell Dev Biol Anim (1996) 32:78–84; Jordan et al., Insect Mol Biol (1998) 7: 215–222; U.S. Pat. No. 5,670,345). Thus, since the same transgenesis system can be used in a variety of phylogenetically diverse animals, comparative functional studies are greatly facilitated, which is especially helpful in evaluating new applications to pest management.

In C. elegans, Tc1 transposable element can be used for directed mutagenesis of a gene of interest. Typically, a Tc1 library is prepared by the methods of Zwaal et al., supra and Plasterk, supra, using a strain in which the Tc1 transposable element is highly mobile and present in a high copy number. The library is screened for Tc1 insertions in the region of interest using PCR with one set of primers specific for Tc1 sequence and one set of gene-specific primers and C. elegans strains that contain Tc1 transposon insertions within the gene of interest are isolated.

In addition to creating loss-of-function phenotypes, transposable elements can be used to incorporate the gene of interest, or mutant or derivative thereof, as an additional gene into any region of an animal's genome resulting in mis-expression (including over-expression) of the gene. A preferred vector designed specifically for misexpression of genes in transgenic Drosophila, is derived from pGMR (Hay et al., Development (1994) 120:2121–2129), is 9 Kb long, and contains: an origin of replication for E. coli; an ampicillin resistance gene; P element transposon 3' and 5' ends to mobilize the inserted sequences; a White marker gene; an expression unit comprising the TATA region of hsp70 enhancer and the 3'untranslated region of α-tubulin gene. The expression unit contains a first multiple cloning site (MCS) designed for insertion of an enhancer and a second MCS located 500 bases downstream, designed for the insertion of a gene of interest. As an alternative to transposable elements, homologous recombination or gene targeting techniques can be used to substitute a gene of interest for one or both copies of the animal's homologous gene. The transgene can be under the regulation of either an exogenous or an endogenous promoter element, and be inserted as either a minigene or a large genomic fragment. In one application, gene function can be analyzed by ectopic expression, using, for example, Drosophila (Brand et al., Methods in Cell Biology (1994) 44:635–654) or C. elegans (Mello and Fire, Methods in Cell Biology (1995) 48:451–482).

Examples of well-characterized heterologous promoters that may be used to create the transgenic animals include heat shock promoters/enhancers, which are useful for temperature induced mis-expression. In Drosophila, these include the hsp70 and hsp83 genes, and in C. elegans, include hsp 16-2 and hsp 16-41. Tissue specific promoters/enhancers are also useful, and in Drosophila, include eyeless (Mozer and Benzer, Development (1994) 120:1049–1058), sevenless (Bowtell et al., PNAS (1991) 88(15):6853–6857), and glass-responsive promoters/enhancers (Quiring et al., Science (1994) 265:785–789) which are useful for expression in the eye; and enhancers/promoters derived from the dpp or vestigal genes which are useful for expression in the wing (Staehling-Hampton et al., Cell Growth Differ. (1994) 5(6):585–593; Kim et al., Nature (1996) 382:133–138). Finally, where it is necessary to restrict the activity of dominant active or dominant negative transgenes to regions where the pathway is normally active, it may be useful to use endogenous promoters of genes in the pathway, such as the subject pathway genes.

In C. elegans, examples of useful tissue specific promoters/enhancers include the myo-2 gene promoter, useful for pharyngeal muscle-specific expression; the hlh-1 gene promoter, useful for body- muscle-specific expression; and the gene promoter, useful for touch-neuron-specific gene expression. In a preferred embodiment, gene fusions for directing the mis-expression of subject pathway genes are incorporated into a transformation vector which is injected into nematodes along with a plasmid containing a dominant selectable marker, such as rol-6. Transgenic animals are identified as those exhibiting a roller phenotype, and the transgenic animals are inspected for additional phenotypes of interest created by mis-expression of the subject pathway gene.

In Drosophila, binary control systems that employ exogenous DNA are useful when testing the mis-expression of genes in a wide variety of developmental stage-specific and tissue-specific patterns. Two examples of binary exogenous regulatory systems include the UAS/GAL4 system from yeast (Hay et al., PNAS (1997) 94(10):5195–5200; Ellis et al., Development (1993) 119(3):855–865), and the "Tet system" derived from E. coli (Bello et al., Development (1998) 125:2193–2202). The UAS/GAL4 system is a well-established and powerful method of mis-expression in Drosophila which employs the $UAS_G$ upstream regulatory sequence for control of promoters by the yeast GAL4 transcriptional activator protein (Brand and Perrimon, Development (1993) 118(2):401–15). In this approach, transgenic Drosophila, termed "target" lines, are generated where the gene of interest to be mis-expressed is operably fused to an appropriate promoter controlled by $UAS_G$. Other transgenic Drosophila strains, termed "driver" lines, are generated where the GAL4 coding region is operably fused to promoters/enhancers that direct the expression of the GAL4 activator protein in specific tissues, such as the eye, wing, nervous system, gut, or musculature. The gene of interest is not expressed in the target lines for lack of a transcriptional activator to drive transcription from the promoter joined to the gene of interest. However, when the UAS-target line is crossed with a GAL4 driver line, mis-expression of the gene of interest is induced in resulting progeny in a specific pattern that is characteristic for that GAL4 line. The technical simplicity of this approach makes it possible to sample the effects of directed mis-expression of the gene of interest in a wide variety of tissues by generating one transgenic target line with the gene of interest, and crossing that target line with a panel of pre-existing driver lines.

In the "Tet" binary control system, transgenic Drosophila driver lines are generated where the coding region for a tetracycline-controlled transcriptional activator (tTA) is operably fused to promoters/enhancers that direct the expression of tTA in a tissue-specific and/or developmental stage-specific manner. The driver lines are crossed with transgenic Drosophila target lines where the coding region for the gene of interest to be mis-expressed is operably fused to a promoter that possesses a tTA-responsive regulatory element. When the resulting progeny are supplied with food supplemented with a sufficient amount of tetracycline, expression of the gene of interest is blocked. Expression of the gene of interest can be induced at will simply by removal of tetracycline from the food. Also, the level of expression of the gene of interest can be adjusted by varying the level of tetracycline in the food. Thus, the use of the Tet system as a binary control mechanism for mis-expression has the advantage of providing a means to control the amplitude and timing of mis-expression of the gene of interest, in addition to spatial control. Consequently, if a gene of interest (e.g. a subject gene) has lethal or deleterious effects when mis-expressed at an early stage in development, such as the embryonic or larval stages, the function of the gene of interest in the adult can still be assessed by adding tetracycline to the food during early stages of development and removing tetracycline later so as to induce mis-expression only at the adult stage.

Dominant negative mutations, by which the mutation causes a protein to interfere with the normal function of a wild-type copy of the protein, and which can result in loss-of-function or reduced-function phenotypes in the presence of a normal copy of the gene, can be made using known methods (Hershkowitz, Nature (1987) 329:219–222). In the case of active monomeric proteins, overexpression of an inactive form, achieved, for example, by linking the mutant gene to a highly active promoter, can cause competition for natural substrates or ligands sufficient to significantly reduce net activity of the normal protein. Alternatively, changes to active site residues can be made to create a virtually irreversible association with a target.

Assays for Change in Gene Expression

Various expression analysis techniques may be used to identify genes which are differentially expressed between a cell line or an animal expressing a wild type subject gene compared to another cell line or animal expressing a mutant subject gene. Such expression profiling techniques include differential display, serial analysis of gene expression (SAGE), transcript profiling coupled to a gene database query, nucleic acid array technology, subtractive hybridization, and proteome analysis (e.g. mass-spectrometry and two-dimensional protein gels). Nucleic acid array technology may be used to determine a global (i.e., genome-wide) gene expression pattern in a normal animal for comparison with an animal having a mutation in subject gene. Gene expression profiling can also be used to identify other genes (or proteins) that may have a functional relation to subject (e.g. may participate in a signaling pathway with the subject gene). The genes are identified by detecting changes in their expression levels following mutation, i.e., insertion, deletion or substitution in, or overexpression, under-expression, mis-expression or knock-out, of the subject gene.

Phenotypes Associated with Subject Pathway Gene Mutations

After isolation of model animals carrying mutated or mis-expressed subject pathway genes or inhibitory RNAs, animals are carefully examined for phenotypes of interest. For analysis of subject pathway genes that have been mutated (i.e. deletions, insertions, and/or point mutations) animal models that are both homozygous and heterozygous for the altered subject pathway gene are analyzed. Examples of specific phenotypes that may be investigated include lethality; sterility; feeding behavior, perturbations in neuromuscular function including alterations in motility, and alterations in sensitivity to pharmaceuticals. Some phenotypes more specific to flies include alterations in: adult behavior such as, flight ability, walking, grooming, phototaxis, mating or egg-laying; alterations in the responses of sensory organs, changes in the morphology, size or number of adult tissues such as, eyes, wings, legs, bristles, antennae, gut, fat body, gonads, and musculature; larval tissues such as mouth parts, cuticles, internal tissues or imaginal discs; or larval behavior such as feeding, molting, crawling, or puparian formation; or developmental defects in any germline or embryonic tissues. Some phenotypes more specific to nematodes include: locomotory, egg laying, chemosensation, male mating, and intestinal expulsion defects. In various cases, single phenotypes or a combination of specific phenotypes in model organisms might point to specific genes or a specific pathway of genes, which facilitate the cloning process.

Genomic sequences containing a subject pathway gene can be used to confirm whether an existing mutant insect or worm line corresponds to a mutation in one or more subject pathway genes, by rescuing the mutant phenotype. Briefly, a genomic fragment containing the subject pathway gene of interest and potential flanking regulatory regions can be subcloned into any appropriate insect (such as Drosophila) or worm (such as *C. elegans*) transformation vector, and injected into the animals. For Drosophila, an appropriate helper plasmid is used in the injections to supply transposase for transposon-based vectors. Resulting germline transformants are crossed for complementation testing to an existing or newly created panel of Drosophila or *C. elegans* lines whose mutations have been mapped to the vicinity of the gene of interest (Fly Pushing: The Theory and Practice of Drosophila Genetics, supra; and *Caenorhabditis elegans: Modern Biological Analysis of an Organism* (1995), Epstein and Shakes, eds.). If a mutant line is discovered to be rescued by this genomic fragment, as judged by complementation of the mutant phenotype, then the mutant line likely harbors a mutation in the subject pathway gene. This prediction can be further confirmed by sequencing the subject pathway gene from the mutant line to identify the lesion in the subject pathway gene.

Identification of Genes that Modify Subject Genes

The characterization of new phenotypes created by mutations or misexpression in subject genes enables one to test for genetic interactions between subject genes and other genes that may participate in the same, related, or interacting genetic or biochemical pathway(s). Individual genes can be used as starting points in large-scale genetic modifier screens as described in more detail below. Alternatively, RNAi methods can be used to simulate loss-of-function mutations in the genes being analyzed. It is of particular interest to investigate whether there are any interactions of subject genes with other well-characterized genes, particularly genes involved in regulation of apoptosis for dmBCL2 and dmSURVIVIN, cell growth and differentiation for dmGFRP, adhesion and proteolysis for dmADAM, DNA binding and transcription for dmMYB, and signal transduction for dmPI3K.

Genetic Modifier Screens

A genetic modifier screen using invertebrate model organisms is a particularly preferred method for identifying genes that interact with subject genes, because large numbers of animals can be systematically screened making it more possible that interacting genes will be identified. In Drosophila, a screen of up to about 10,000 animals is considered to be a pilot-scale screen. Moderate-scale screens usually employ about 10,000 to about 50,000 flies, and large-scale screens employ greater than about 50,000 flies. In a genetic modifier screen, animals having a mutant phenotype due to a mutation in or misexpression of one or more subject genes are further mutagenized, for example by chemical mutagenesis or transposon mutagenesis.

The procedures involved in typical Drosophila genetic modifier screens are well-known in the art (Wolfner and Goldberg, Methods in Cell Biology (1994) 44:33–80; and Karim et al., Genetics (1996) 143:315–329). The procedures used differ depending upon the precise nature of the mutant allele being modified. If the mutant allele is genetically recessive, as is commonly the situation for a loss-of-function allele, then most typically males, or in some cases females, which carry one copy of the mutant allele are exposed to an effective mutagen, such as EMS, MMS, ENU, triethylamine, diepoxyalkanes, ICR-170, formaldehyde, X-rays, gamma rays, or ultraviolet radiation. The mutagenized animals are crossed to animals of the opposite sex that also carry the mutant allele to be modified. In the case where the mutant allele being modified is genetically dominant, as is commonly the situation for ectopically expressed genes, wild type males are mutagenized and crossed to females carrying the mutant allele to be modified.

The progeny of the mutagenized and crossed flies that exhibit either enhancement or suppression of the original phenotype are presumed to have mutations in other genes, called "modifier genes", that participate in the same phenotype-generating pathway. These progeny are immediately crossed to adults containing balancer chromosomes and used as founders of a stable genetic line. In addition, progeny of the founder adult are retested under the original screening conditions to ensure stability and reproducibility of the phenotype. Additional secondary screens may be employed, as appropriate, to confirm the suitability of each new modifier mutant line for further analysis.

Standard techniques used for the mapping of modifiers that come from a genetic screen in Drosophila include meiotic mapping with visible or molecular genetic markers; male-specific recombination mapping relative to P-element insertions; complementation analysis with deficiencies, duplications, and lethal P-element insertions; and cytological analysis of chromosomal aberrations (Fly Pushing: Theory and Practice of Drosophila Genetics, supra; Drosophila: A Laboratory Handbook, supra). Genes corresponding to modifier mutations that fail to complement a lethal P-element may be cloned by plasmid rescue of the genomic sequence surrounding that P-element. Alternatively, modifier genes may be mapped by phenotype rescue and positional cloning (Sambrook et al., supra).

Newly identified modifier mutations can be tested directly for interaction with other genes of interest known to be involved or implicated with subject genes using methods described above. Also, the new modifier mutations can be tested for interactions with genes in other pathways that are not believed to be related to subject genes' pathways.

The modifier mutations may also be used to identify "complementation groups". Two modifier mutations are considered to fall within the same complementation group if animals carrying both mutations in trans exhibit essentially the same phenotype as animals that are homozygous for each mutation individually and, generally are lethal when in trans to each other (Fly Pushing: The Theory and Practice of Drosophila Genetics, supra). Generally, individual complementation groups defined in this way correspond to individual genes.

When subject modifier genes are identified, homologous genes in other species can be isolated using procedures based on cross-hybridization with modifier gene DNA probes, PCR-based strategies with primer sequences derived from the modifier genes, and/or computer searches of sequence databases. For therapeutic applications related to the function of subject genes, human and rodent homologs of the modifier genes are of particular interest.

Although the above-described Drosophila genetic modifier screens are quite powerful and sensitive, some genes that interact with subject genes may be missed in this approach, particularly if there is functional redundancy of those genes. This is because the vast majority of the mutations generated in the standard mutagenesis methods will be loss-of-function mutations, whereas gain-of-function mutations that could reveal genes with functional redundancy will be relatively rare. Another method of genetic screening in Drosophila has been developed that focuses specifically on systematic gain-of-function genetic screens (Rorth et al., Development (1998) 125:1049–1057). This method is based on a modular mis-expression system utilizing components of the GAL4/UAS system (described above) where a modified P element, termed an "enhanced P" (EP) element, is genetically engineered to contain a GAL4-responsive UAS element and promoter. Any other transposons can also be used for this system. The resulting transposon is used to randomly tag genes by insertional mutagenesis (similar to the method of P element mutagenesis described above). Thousands of transgenic Drosophila strains, termed EP lines, can be generated, each containing a specific UAS-tagged gene. This approach takes advantage of the preference of P elements to insert at the 5'-ends of genes. Consequently, many of the genes that are tagged by insertion of EP elements become operably fused to a GAL4-regulated promoter, and increased expression or mis-expression of the randomly tagged gene can be induced by crossing in a GAL4 driver gene.

Systematic gain-of-function genetic screens for modifiers of phenotypes induced by mutation or mis-expression of a subject gene can be performed by crossing several thousand Drosophila EP lines individually into a genetic background containing a mutant or mis-expressed subject gene, and further containing an appropriate GAL4 driver transgene. It is also possible to remobilize the EP elements to obtain novel insertions. The progeny of these crosses are then analyzed for enhancement or suppression of the original mutant phenotype as described above. Those identified as having mutations that interact with the subject gene can be tested further to verify the reproducibility and specificity of this genetic interaction. EP insertions that demonstrate a specific genetic interaction with a mutant or mis-expressed subject gene, have a physically tagged new gene which can be identified and sequenced using PCR or hybridization screening methods, allowing the isolation of the genomic DNA adjacent to the position of the EP element insertion.

EXAMPLES

The following examples describe the isolation and cloning of the nucleic acid sequence of SEQ ID NOs:1, 3, 5, 7, 9, 11, and 13 and how these sequences, and derivatives and fragments thereof, as well as other subject pathway nucleic acids and gene products can be used for genetic studies to elucidate mechanisms of the subject pathway as well as the discovery of potential pharmaceutical agents that interact with the pathway.

These Examples are provided merely as illustrative of various aspects of the invention and should not be construed to limit the invention in any way.

Example 1

Preparation of Drosophila cDNA Library

A Drosophila expressed sequence tag (EST) cDNA library was prepared as follows. Tissue from mixed stage embryos (0–20 hour), imaginal disks and adult fly heads were collected and total RNA was prepared. Mitochondrial rRNA was removed from the total RNA by hybridization with biotinylated rRNA specific oligonucleotides and the resulting RNA was selected for polyadenylated mRNA. The resulting material was then used to construct a random primed library. First strand cDNA synthesis was primed using a six nucleotide random primer. The first strand cDNA was then tailed with terminal transferase to add approximately 15 dGTP molecules. The second strand was primed using a primer which contained a NotI site followed by a 13 nucleotide C-tail to hybridize to the G-tailed first strand cDNA. The double stranded cDNA was ligated with BstX1 adaptors and digested with NotI. The cDNA was then fractionated by size by electrophoresis on an agarose gel and the cDNA greater than 700 bp was purified. The cDNA was ligated with NotI, BstX1 digested pCDNA-sk+vector (a derivative of pBluescript, Stratagene) and used to transform E. coli (XL1blue). The final complexity of the library was 6×10$^6$ independent clones.

The cDNA library was normalized using a modification of the method described by Bonaldo et al. (Genome Research (1996) 6:791–806). Biotinylated driver was prepared from the cDNA by PCR amplification of the inserts and allowed to hybridize with single stranded plasmids of the same library. The resulting double-stranded forms were removed using strepavidin magnetic beads, the remaining single stranded plasmids were converted to double stranded molecules using Sequenase (Amersham, Arlington Hills, Ill.), and the plasmid DNA stored at −20° C. prior to transformation. Aliquots of the normalized plasmid library were used to transform E. coli (XL1blue or DH10B), plated at moderate density, and the colonies picked into a 384-well master plate containing bacterial growth media using a Qbot robot (Genetix, Christchurch, UK). The clones were allowed to grow for 24 hours at 37° C. then the master plates were frozen at −80° C. for storage. The total number of colonies picked for sequencing from the normalized library was 240,000. The master plates were used to inoculate media for growth and preparation of DNA for use as template in sequencing reactions. The reactions were primarily carried out with primer that initiated at the 5' end of the cDNA inserts. However, a minor percentage of the clones were also sequenced from the 3'end. Clones were selected for 3' end sequencing based on either further biological interest or the selection of clones that could extend assemblies of contiguous sequences ("contigs") as discussed below. DNA sequencing was carried out using ABI377 automated sequencers and used either ABI FS, dirhodamine or BigDye chemistries (Applied Biosystems, Inc., Foster City, Calif.).

Analysis of sequences were done as follows: the traces generated by the automated sequencers were base-called using the program "Phred" (Gordon, Genome Res. (1998) 8:195–202), which also assigned quality values to each base. The resulting sequences were trimmed for quality in view of the assigned scores. Vector sequences were also removed. Each sequence was compared to all other fly EST sequences using the BLAST program and a filter to identify regions of near 100% identity. Sequences with potential overlap were then assembled into contigs using the programs "Phrap", "Phred" and "Consed" (Phil Green, University of Washington, Seattle, Wash.;). The resulting assemblies were then compared to existing public databases and homology to known proteins was then used to direct translation of the consensus sequence. Where no BLAST homology was available, the statistically most likely translation based on codon and hexanucleotide preference was used. The Pfam (Bateman et al., Nucleic Acids Res. (1999) 27:260–262) and Prosite (Hofmann et al., Nucleic Acids Res. (1999) 27(1) :215–219) collections of protein domains were used to identify motifs in the resulting translations. The contig sequences were archived in an Oracle-based relational database (FlyTag™, Exelixis, Inc., South San Francisco, Calif.)

Example 2

Cloning of Nucleic Acid Sequences

Unless otherwise noted, the PCR conditions used for cloning the subject nucleic acid sequences was as follows: A denaturation step of 94° C., 5 min; followed by 35 cycles of: 94° C. 1 min, 55° C. 1 min 72° C. 1 min; then, a final extension at 72° C. 10 min.

All DNA sequencing reactions were performed using standard protocols for the BigDye sequencing reagents (Applied Biosystems, Inc.) and products were analyzed using ABI 377 DNA sequencers. Trace data obtained from the ABI 377 DNA sequencers was analyzed and assembled into contigs using the Phred-Phrap programs.

Well-separated, single colonies were streaked on a plate and end-sequenced to verify the clones. Single colonies were picked and the enclosed plasmid DNA was purified using Qiagen REAL Preps (Qiagen, Inc., Valencia, Calif.). Samples were then digested with appropriate enzymes to excise insert from vector and determine size, for example the vector pOT2, and can be excised with XhoI/EcoRI; or pBluescript (Stratagene) and can be excised with BssH II. Clones were then sequenced using a combination of primer walking and in vitro transposon tagging strategies.

For primer walking, primers were designed to the known DNA sequences in the clones, using the Primer-3 software (Steve Rozen, Helen J. Skaletsky (1998) Primer3.). These primers were then used in sequencing reactions to extend the sequence until the full sequence of the insert was determined.

The GPS-1 Genome Priming System in vitro transposon kit (New England Biolabs, Inc., Beverly, Mass.) was used for transposon-based sequencing, following manufacturer's protocols. Briefly, multiple DNA templates with randomly interspersed primer-binding sites were generated. These clones were prepared by picking 24 colonies/clone into a Qiagen REAL Prep to purify DNA and sequenced by using supplied primers to perform bidirectional sequencing from both ends of transposon insertion.

Sequences were then assembled using Phred/Phrap and analyzed using Consed. Ambiguities in the sequence were resolved by resequencing several clones.

For dmBCL2, this effort resulted in a contiguous nucleotide sequence of 1647 bases in length, encompassing an open reading frame (ORF) of 951 nucleotides encoding a predicted protein of 317 amino acids. The ORF extends from base 551–1501 of SEQ ID NO:1.

For dmSURVIVIN, this effort resulted in a contiguous nucleotide sequence of 624 bases in length, encompassing an open reading frame (ORF) of 459 nucleotides encoding a predicted protein of 153 amino acids. The ORF extends from base 61–519 of SEQ ID NO:3.

For dmGFRP, this effort resulted in a contiguous nucleotide sequence of 2595 bases in length, encompassing an open reading frame (ORF) of 1434 nucleotides encoding a predicted protein of 478 amino acids. The ORF extends from base 501–1932 of SEQ ID NO:5.

For dmADAM, this effort resulted in a contiguous nucleotide sequence of 3994 bases in length, encompassing an open reading frame (ORF) of 2343 nucleotides encoding a predicted protein of 781 amino acids. The ORF extends from base 478–2820 of SEQ ID NO:7.

For dmMYB, this effort resulted in a contiguous nucleotide sequence of 2242 bases in length, encompassing an open reading frame (ORF) of 2085 nucleotides encoding a predicted protein of 695 amino acids. The ORF extends from base 60–2147 of SEQ ID NO:9.

For dmPI3K, this effort resulted in a contiguous nucleotide sequence of 5706 bases in length, encompassing an open reading frame (ORF) of 5706 nucleotides encoding a predicted protein of 1902 amino acids.

For drnMCC, this effort resulted in a contiguous nucleotide sequence of 1595 bases in length, encompassing an open reading frame (ORF) of 1014 nucleotides encoding a predicted protein of 338 amino acids. The ORF extends from base 42–1058 of SEQ ID NO:13.

Example 3
Analysis of dmBCL2 Nucleic Acid Sequences

Upon completion of cloning, the sequences were analyzed using the Pfam, PSORT, and Prosite programs. Pfam predicted an apoptosis regulator protein domain (PF00452) at amino acids 146–208, corresponding to nucleotides 988–1174. Other potential motifs include: N-Glycosylation site (PS00001, PDOC00001) at amino acids 163–166 (nucleotides 1039–1048); cAMP and cGMP protein kinase phosphorylation sites (PS00004, PDOC00004) at amino acids 28–31, 121–124, and 285–288 (nucleotides 634–643, 913–922, and 1405–1414); Protein kinase C phosphorylation site (PS00005, PDOC00005) at amino acids 83–85, 124–126, and 307–309 (nucleotides 799–808, 922–931, and 1471–1480); Casein Kinase II phosphorylation site (PS00006, PDOC00006) at amino acids 17–20, and 148–151 (nucleotides 601–610, and 994–1003); N-myristolation site (PS00008, PDOC00008) at amino acids 30–35, 44–49, 45–50, 47–52, 51–56, 68–73, and 268–273 (nucleotides 640–655, 682–697, 685–700, 691–706, 703–718, and 1354–1369); and amidation site (PS00009, PDOC00009) at amino acid 260–263 (nucleotides 1330–1339).

Nucleotide and amino acid sequences for the dmBCL2 nucleic acid sequence and its encoded proteins were searched against all available nucleotide and amino acid sequences in the public databases, using BLAST (Altschul et al., supra). Table 1 below summarizes the results. The 5 most similar sequences are listed.

TABLE 1

| GI# | DESCRIPTION |
| --- | --- |
| DNA BLAST | |
| 5670596 = AC007624 | *Drosophila melanogaster* chromosome 2 clone BACR10F15 (D621) RPCI-98 10.F.15 map 42E-43A strain y; cn bw sp, ***SEQUENCING IN PROGRESS ***, 54 unordered pieces |
| 4887256 = AC007624 | *Drosophila melanogaster* chromosome 2 clone BACR10F15 (D621) RPCI-98 10.F.15 map 42E-43A strain y2; cn bw sp, *SEQUENCING IN PROGRESS*, 20 unordered pieces. |
| 4885670 = AC007593 | *Drosophila melanogaster* chromosome 2 clone BACR01C10 (D620) RPCI-98 01.C.10 map 42E-43A strain y2; cn bw sp, *SEQUENCING IN PROGRESS*, 29 unordered pieces |
| 4417483 = AI513093 | *Drosophila melanogaster* cDNA clone GH01265 3prime, mRNA sequence |
| 2152793 = AA440915 | *Drosophila melanogaster* cDNA clone LD12719 5prime, mRNA sequence |
| PROTEIN BLAST | |
| 5802578 = AAD51719 | Bcl-2-related ovarian killer protein [*Homo sapiens*] |
| 6456033 = AAF09129 | Bcl-2 related ovarian killer [*Homo sapiens*] |
| 2645560 = AAB87418 | Bcl-2-related ovarian killer protein [*Rattus norvegicus*] |

TABLE 1-continued

| GI# | DESCRIPTION |
| --- | --- |
| 2689660 = AAC53582 | apoptosis activator Mtd [*Mus musculus*] |
| 3676403 = AAC61928 | Bcl-2-related ovarian killer protein [*Rattus norvegicus*] |

The closest homolog predicted by BLAST analysis is a Bcl2-related ovarian killer protein, with 35% identity and 53% homology with dmBCL2.

The BLAST analysis also revealed several other apoptosis regulator proteins that share significant amino acid homology with dmBCL2.

BLAST results for the dmBCL2 amino acid sequence indicate 10 amino acid residues as the shortest stretch of contiguous amino acids that is novel with respect to published sequences and 12 amino acids as the shortest stretch of contiguous amino acids for which there are no sequences contained within public database sharing 100% sequence similarity.

All proteins belonging to the Bcl-2 family contain either a BH1, BH2, BH3, or BH4 domain (Reed et al., Adv. Exp. Med. Biol. (1996) 406:99–112). All anti-apoptotic proteins contain BH1 and BH2 domains; some of them contain an additional N-terminal BH4 domain (e.g. Bcl-2, Bcl-x(L), Bcl-w), which is not seen in pro-apoptotic proteins with the exception of Bcl-x(S). All pro-apoptotic proteins contain a BH3 domain (except for Bad) necessary for dimerization with other proteins of Bcl-2 family and crucial for their killing activity; some of them also contain BH1 and BH2 domains (Bax, Bak). The BH3 domain is also present in some anti-apoptotic proteins, such as Bcl-2 or Bcl-x(L). The protein encoded by dmBCL2 contains only a BH3 domain and thus it is most likely a pro-apoptotic protein.

Example 4
Analysis of dmSURVIVIN Nucleic Acid Sequences

Upon completion of cloning, the sequences we re analyzed using the Pfam and Prosite programs. Pfam predicted a BIR (Inhibitor of apoptosis, PF00653) homology domain at amino acids 31–101 (nucleotides 153–363). Potential motifs included: N-glycosylation sites (PS00001, PDOC00001) at amino acids 65–68 and 108–111 (nucleotides 255–264 and 384–393); Protein kinase C phosphorylation sites (PS00005, PDOC00005) at amino acids 34–36, 61–63, and 129–131 (nucleotides 162–168, 243–249, and 447–453); Casein kinase II phosphorylation sites (PS00006, PDOC00006) at amino acids 61–64, and 103–106 (nucleotides 243–252, and 369–378), and tyrosine kinase phosphorylation site (PS00007, PDOC00007) at amino acids 50–57 (nucleotides 210–231).

Nucleotide and amino acid sequences for the dmSURVIVIN nucleic acid sequence and its encoded protein were se arched against all available nucleotide and amino acid sequences in the public databases, using BLAST (Altschul et al., supra). Table 2 below summarizes the results. The 5 most similar sequences are listed.

TABLE 2

| GI# | DESCRIPTION |
| --- | --- |
| DNA BLAST | |
| 6223261 = AC013070 | *Drosophila melanogaster*, *SEQUENCING IN PROGRESS*, in ordered pieces |

TABLE 2-continued

| GI# | DESCRIPTION |
| --- | --- |
| 5670523 = AC007824 | *Drosophila melanogaster* chromosome 3 clone BACR02L16 (D715) RPCI-98 02.L.16 map 89E-90A strain y; cn bw sp, *SEQUENCING IN PROGRESS*, 91 unordered pieces |
| 5053157 = AC007807 | *Drosophila melanogaster* chromosome 3 clone BACR01E04 (D714) RPCI-98 01.E.4 map 89E-89E strain y; cn bw sp, *SEQUENCING IN PROGRESS*, 32 unordered pieces. |
| 5670524 = AC007807 | *Drosophila melanogaster* chromosome 3 clone BACR01E04 (D714) RPCI-98 01.E.4 map 89E-89E strain y; cn bw sp, *SEQUENCING IN PROGRESS*, 98 unordered pieces |
| 3135206 = AB013819 | *Mus musculus* mRNA for TIAP, complete cds |
| PROTEIN BLAST | |
| 4959079 = AAD34226 | Inhibitor of apoptosis homolog [Homo sapiens] |
| 2315863 = AAC51660 | Apoptosis inhibitor survivin [Homo sapiens] |
| 4588768 = AAD26199 | Survivin140 [*Mus musculus*] |
| 4959077 = AAD34225 | Inhibitor of apoptosis homolog [*Mus musculus*] |
| 4588770 = AAD26201 | Survivin121 [*Mus musculus*] |

The closest homolog predicted by BLAST analysis is an inhibitor of apoptosis homolog from human with 40% identity and 57% homology to dmSURVIVIN.

The BLAST analysis also revealed several other apoptosis inhibitor and survivin proteins which share significant amino acid homology with dmSURVIVIN.

Members of the IAP family contain two or three BIR repeats and a RING finger in their C-terminus. Human NAIP is the only known exception to IAPs in that it does not contain a C-terminal RING-finger domain. NAIP is a neuronal protein found to be deleted in many cases of spinal muscular atrophy (Chen Q., et al., Genomics Feb. 15, 1998; 48(1):121–7). Spinal muscular atrophies (SMA), which are characterized by motor neuron loss and progressive paralysis, are among the most common autosomal recessive disorders. The SMA region of chromosome 5q13.1 is distinguished by variable amplification of genomic sequence incorporating a number of genes and pseudogenes. Recently, two SMA candidate genes mapping to this area were identified: survival motor neuron (SMN) and neuronal apoptosis inhibitory protein (NAIP). The telomeric copy of SMN (SMNtel) is deleted in over 95% of cases of SMA, with NAIP deletions primarily seen in type I SMA. The Alu-rich NAIP-SMNtel interval contains the microsatellite polymorphisms that are deleted in as many as 80% of type I SMA chromosomes, focusing attention on this region in the pathogenesis of type I SMA.

Members of the IAP family typically contain two or three BIR (Inhibitor of apoptosis domain) repeats and a RING finger in their C-terminus. dmSURVIVIN contains one BIR domain and no RING finger. However, all of the perfectly conserved elements of a BIR domain are present. Interestingly, phylogenetically dmSURVIVIN is most closely related to human NAIP, which is the only known exception to IAPs containing C-terminal RING-finger domains. NAIP is a neuronal protein that is absent in many cases of spinal muscular atrophy (Chen Q., et al., Genomics Feb. 15, 1998; 48(1):121–7). Accordingly, the animal and cell models of dmSURVIVIN expression and misexpression described above may be useful in the study of spinal muscular atrophy.

BLAST results for the dmSURVIVIN amino acid sequence indicate 7 amino acid residues as the shortest stretch of contiguous amino acids that is novel with respect to published sequences and 12 amino acids as the shortest stretch of contiguous amino acids for which there are no sequences contained within public database sharing 100% sequence similarity.

Example 5
Analysis of dmGFRP Nucleic Acid Sequences

Upon completion of cloning, the sequences were analyzed using the Pfam and Prosite programs. Pfam predicted a zinc finger domain at amino acid residues 30–67, corresponding to nucleotides 590–704.

Nucleotide and amino acid sequences for the dmGFRP nucleic acid sequence and encoded protein were searched against all available nucleotide and amino acid sequences in the public databases, using BLAST (Altschul et al., supra). Table 3 below summarizes the results. The 5 most similar sequences are listed.

TABLE 3

| GI# | DESCRIPTION |
| --- | --- |
| DNA BLAST | |
| 5670561 = AC007575 | *Drosophila melanogaster* chromosome 3 clone BACR42H10 (D671) RPCI-98 42.H.10 map 82F-83A strain y; cn bw sp, *SEQUENCING IN PROGRESS*, 38 unordered pieces |
| 4878045 = AC007575 | *Drosophila melanogaster* chromosome 3 clone BACR42H10 (D671) RPCI-98 42.H.10 map 82F-83A strain y; cn bw sp, *SEQUENCING IN PROGRESS*, 38 unordered pieces |
| 4878046 = AC007532 | *Drosophila melanogaster* chromosome 3 clone BACR01D10 (D670) RPCI-98 01.D.10 map 82F-82F strain y; cn bw sp, *SEQUENCING IN PROGRESS*, 39 unordered pieces |
| 5670562 = AC007532 | *Drosophila melanogaster* chromosome 3 clone BACR01D10 (D670) RPCI-98 01.D.10 map 82F-82F strain y; cn bw sp, *SEQUENCING IN PROGRESS*, 39 unordered pieces |
| 6437379 = AC013956 | *Drosophila melanogaster*, *** SEQUENCING IN PROGRESS***, in ordered pieces |
| PROTEIN BLAST | |
| 631839 = A53770 | growth factor-responsive protein, vascular smooth muscle - rat |
| 469478 = AAA19321 | SM-20 [*Rattus norvegicus*] |
| 5923812 = AAD56365 | EGL-9 [*Caenorhabditis elegans*] |
| 3880763 = CAA16314 | (AL021475) Weak similarity with apoptosis protein RP-8; cDNA EST EMBL:D68399 comes from this gene; cDNA EST EMBL:C12479 comes from this gene; cDNA EST yk284b6.5 comes from this gene; cDNA EST yk358g4.5 comes from this gene; cDNA EST EMBL:M88987 comes from this gene [*Caenorhabditis elegans*] |
| 3876300 = CAA94893 | Weak similarity with apoptosis protein RP-8; cDNA EST EMBL:D68399 comes from this gene; cDNA EST EMBL:C12479 comes from this gene; cDNA EST yk284b6.5 comes from this gene; cDNA EST yk358g4.5 comes from this gene; cDNA EST EMBL:M88987 comes from this gene [*Caenorhabditis elegans*] |

The closest homolog predicted by BLAST analysis is a growth factor responsive protein from rat, with 50% sequence identity and 67% sequence homology to the C-terminal region of dmGFRP. However, the overall identity between the two proteins is only 29%.

BLAST results for the dmGFRP amino acid sequence indicate 8 amino acid residues as the shortest stretch of contiguous amino acids that is novel with respect to published sequences and 19 amino acids as the shortest stretch of contiguous amino acids for which there are no sequences contained within public database sharing 100% sequence similarity.

Example 6
Analysis of dmADAM Nucleic Acid Sequences

Upon completion of cloning, the sequences were analyzed using the Pfam and Prosite programs. PFAM predicted 2 transmembrane domains at amino acids 110–126 and 572–588, corresponding to nucleotides 807–855, and 2193–2241, respectively. PFAM also predicted four functional domains: a disintegrin domain.(PF00200) at amino acids 285–363 (nucleotides 1332–1566); a zinc-binding metalloprotease domain (PF00099) at amino acids 206–220 (nucleotides 1095–1137); an EGF-like domain (PF00008) at amino acids 519–546 (nucleotides 2034–2115); and a laminin-EGF-like domain (PF00053) at amino acids 522–559 (nucleotides 2043–2154).

Nucleotide and amino acid sequences for the dmADAM nucleic acid sequences and their encoded proteins were searched against all available nucleotide and amino acid sequences in the public databases, using BLAST (Altschul et al., supra). Table 4 below summarizes the results. The 5 most similar sequences are listed.

TABLE 4

| GI# | DESCRIPTION |
| --- | --- |
| DNA BLAST | |
| 6554259 = AC017740 | *Drosophila melanogaster,* \*\*\*SEQUENCING IN PROGRESS\*\*\*, in ordered pieces |
| 4446690 = AI532555 | *Drosophila melanogaster* cDNA clone SD04095 5prime, mRNA sequence |
| 4446544 = AI523409 | *Drosophila melanogaster* cDNA clone SD03917 5prime, mRNA sequence |
| 394331 = AI293908 | *Drosophila melanogaster* cDNA clone LP07167 5prime, mRNA sequence |
| 4934221 = 394331 | *Drosophila melanogaster* genome survey sequence TET3 end of BAC # BACR18C01 of RPCI-98 library from *Drosophila melanogaster* (fruit fly), genomic survey sequence |
| PROTEIN BLAST | |
| 3873969 = CAB03832 | Similarity to Mouse meltrin alpha protein, *Caenorhabditis elegans.* |
| 3878182 = CAA94147 | Similarity to Mouse meltrin alpha protein, *Caenorhabditis elegans.* |
| 2137512 = S60257 | meltrin alpha - mouse |
| 1584290 = 2122364B | meltrin alpha [*Mus musculus*] |
| 1054587 = BAA08912 | meltrin alpha [*Mus musculus*] |

The closest homolog predicted by BLAST analysis is a *C. elegans* sequence with similarity to mouse meltrin, with an overall 40% identity and 56% homology to dmADAM.

Internally, dmADAM has several domains of interest: a distinct zinc-metalloprotease motif, which can be placed into the M12b sub-family of Zn-proteases (known as the reprolysins), one and possibly two EGF domains, and a disintegrin domain.

Globally, dmADAM shows wide, weak homology to a number of sequences. There are approximately 45 sequences with similar homology domains. Overall, dmADAM shows 20–25% sequence identity with a wide range of ADAM, MDC, fertilin and meltrin proteins from different organisms. Most, if not all, of these sequences are metalloproteases with EGF and/or disintegrin domains, however they have a wide range of specificities.

The domain structure of dmADAM places it clearly in the ADAM family (a disintegrin and a metalloprotease), of which family only a single alternate member is known from Drosophila: Kuzbanian.

BLAST results for the dmADAM amino acid sequence indicate 11 amino acid residues as the shortest stretch of contiguous amino acids that is novel with respect to published sequences and 13 amino acids as the shortest stretch of contiguous amino acids for which there are no sequences contained within public database sharing 100% sequence similarity.

Example 7
Analysis of dmMYB Nucleic Acid Sequences

Upon completion of cloning, the sequences were analyzed using the Pfam and Prosite programs. PFAM predicted a Myb-like DNA binding domain (PF00249) at amino acids 348–390, corresponding to nucleotide residues 1101–1229. Prosite predicted several likely nuclear localization signals, at amino acids 18–21, 19–22, 20–23, 146–152, 343–346, 344–347, 378–384, 441–447, 444–450, 484–487, 499–505, 501–504, 502–505, and 504–510, corresponding to nucleotides 111–122, 114–125, 117–128,495–515, 1086–1097, 1089–1100, 1191–1211, 1380–1400, 1389–1409, 1509–1520, 1554–1547, 1560–1571, 1563–1574, and 1569–1589, respectively.

Nucleotide and amino acid sequences for the dmMYB nucleic acid sequence and the encoded protein were searched against all available nucleotide and amino acid sequences in the public databases, using BLAST (Altschul et al., supra). Table 5 below summarizes the results. The 5 most similar sequences are listed.

TABLE 5

| GI# | DESCRIPTION |
| --- | --- |
| DNA BLAST | |
| 6436998 = AC014337 | *Drosophila melanogaster,* \*\*\*SEQUENCING IN PROGRESS\*\*\*, in ordered pieces |
| 4056409 = AC005443 | *Drosophila melanogaster,* chromosome 2L, region 34B5-34B9, P1 clone DS05554, complete sequence |
| 3478471 = AI110147 | *Drosophila melanogaster* cDNA clone GH09630 5prime, mRNA sequence |
| 4200817 = AI386806 | *Drosophila melanogaster* cDNA clone GH17072 5prime, mRNA sequence |
| 4245268 = AI402181 | *Drosophila melanogaster* cDNA clone GH09630 3prime, mRNA sequence. |
| PROTEIN BLAST | |
| 4107317 = CAA22645 | putative transcription factor tfiiib component [*Schizosaccharomyces pombe*] |
| 2133106 = S62141 | RNA polymerase III transcription factor TFIIIB chain B"-yeast (*Saccharomyces cerevisiae*) |
| 1301890 = CAA95906 | ORF YNL039w [*Saccharomyces cerevisiae*] |
| 1019115 = AAC49073 | transcription factor TFIIIB B" component [*Saccharomyces cerevisiae*] |
| 1052983 = AAC49348 | transcription factor TFIIIB90 [*Saccharomyces cerevisiae*] | dmMYB has a multitude of nuclear localization signals as predicted by PSORT2. PFAM reveals a weak homology to PF00249, a myb-like DNA-binding domain. BLAST analysis of the amino acid sequence shows ~33% identity to a number of transcription factor IIIB (TFIIIB90=TFIIIB") proteins from yeast. TFIIIB is an important determinant of the biosynthetic capacity of cells, controlling the production of essential products such as tRNA and 5S rRNA (White, Int. J. Oncol. (1998) 12(4):741–748). The unrelated tumor suppressors RB and p53 both exert inhibitory influences upon TFIIIB. In contrast, several viruses have been shown to activate TFIIIB, including HBV and HTLV-1, and thus it has been suggested that deregulation of TFIIIB may be a significant step towards tumor development (White, supra).

BLAST results for the dmMYB amino acid sequence indicate 5 amino acid residues as the shortest stretch of contiguous amino acids that is novel with respect to published sequences and 10 amino acids as the shortest stretch of contiguous amino acids for which there are no sequences contained within public database sharing 100% sequence similarity.

Example 8
Analysis of dmPI3K Nucleic Acid Sequences

Upon completion of cloning, the sequences were analyzed using the Pfam and Prosite programs. Prosite predicted a PI3K domain (PDOC00710) at amino acids 1570–1890 (nucleotides 4710–5672).

Nucleotide and amino acid sequences for the dmPI3K nucleic acid sequence and encoded proteins were searched against all available nucleotide and amino acid sequences in the public databases, using BLAST (Altschul et al., supra). Table 6 below summarizes the results. The 5 most similar sequences are listed.

TABLE 6

| GI# | DESCRIPTION |
|---|---|
| DNA BLAST | |
| 6436787 = AC014548 | *Drosophila melanogaster*, \*\*\*SEQUENCING IN PROGRESS\*\*\*, in ordered pieces |
| 5656713 = AC005712 | *Drosophila melanogaster* chromosome 2 clone DS06766 (D434) map 41D1-41D2 strain y; cn bw sp, \*\*\*SEQUENCING IN PROGRESS\*\*\*, 25 unordered pieces |
| 5649331 = AC008181 | *Drosophila melanogaster* chromosome 2 clone DS07289 (D337) map 41E3-41E6 strain y; cn bw sp, \*\*\*SEQUENCING IN PROGRESS\*\*\*, 6 unordered pieces |
| 4951078 = AL071036 | *Drosophila melanogaster* genome survey sequence TET3 end of BAC: BACR31H22 of RPCI-98 library from *Drosophila melanogaster* (fruit fly), genomic survey sequence |
| 4151928 = AF110377 | *Homo sapiens* PCAF-associated factor 400 (PAF400) mRNA, complete cds |
| PROTEIN BLAST | |
| 4165077 = AAD09420 | TRRAP protein [*Homo sapiens*] |
| 4151929 = AAD04629 | PCAF-associated factor 400 [*Homo sapiens*] |
| 3694663 = AAC62433 | similar to hypothetical proteins P38811 (PID:g731689) and Q10064 (PID:g1351684) [*Homo sapiens*] |
| 626646 = S46715 | hypothetical protein YHR099w - yeast (*Saccharomyces cerevisiae*) |
| 487929 = AAB68923 | Tra1p [*Saccharomyces cerevisiae*] |

The closest homolog predicted by BLAST analysis is the human TRRAP and PCAF proteins, with 55% sequence identity and 71% sequence homology to dmPI3K. The homologies are particularly strong in the C-terminus region of the dmPI3K.

BLAST results for the dmPI3K amino acid sequence indicate 22 amino acid residues as the shortest stretch of contiguous amino acids that is novel with respect to published sequences and 38 amino acids as the shortest stretch of contiguous amino acids for which there are no sequences contained within public database sharing 100% sequence similarity.

Example 9
Analysis of dmMCC Nucleic Acid Sequences

Nucleotide and amino acid sequences the dmMCC nucleic acid sequences and their encoded proteins were searched against all available nucleotide and amino acid sequences in the public databases, using BLAST (Altschul et al., supra). Table 7 below summarizes the results. The 5 most similar sequences are listed.

TABLE 7

| GI# | DESCRIPTION |
|---|---|
| DNA BLAST | |
| 6664986 = AC019911 | *Drosophila melanogaster*, \*\*\*SEQUENCING IN PROGRESS\*\*\*, in ordered pieces |
| 6665028 = AC019869 | *Drosophila melanogaster*, \*\*\*SEQUENCING IN PROGRESS\*\*\*1, in ordered pieces |
| 1819311 = I28535 | Sequence 1 from U.S. Pat. No. 5571905 |
| 1819835 = I29044 | Sequence 1 from U.S. Pat. No. 5576422 |
| 3014589 = I78435 | Sequence 1 from U.S. Pat. No. 5693536 |
| PROTEIN BLAST | |
| 1828481 = AAB42935 | Sequence 2 from U.S. Pat. No. 5571905 |
| 1828732 = AAB43186 | Sequence 2 from U.S. Pat. No. 5576422 |
| 3015128 = AAC12008 | Sequence 2 from U.S. Pat. No. 5693536 |
| 107363 = A33166 | colorectal tumor suppressor protein - human |
| 181035 = AAA52069 | colorectal mutant cancer protein [*Homo sapiens*] |

The 5 closest homologs predicted by BLAST analysis are the human wild type or mutated MCC gene, with 52% overall identity and 78% overall homology with dmMCC. BLAST results for the dmMCC amino acid sequence indicate 7 amino acid residues as the shortest stretch of contiguous amino acids that is novel with respect to published sequences and 9 amino acids as the shortest stretch of contiguous amino acids for which there are no sequences contained within public database sharing 100% sequence similarity.

Example 10
Analysis of DNA Fragmentation by TUNEL

Cells are transfected with wild-type or recombinant dmBCL2or dmSURVIVIN, and grown in the presence of various compounds in the cell culture medium. Nontransfected cells are used as controls. In situ detection of apoptotic cells is performed on cytospin preparations as well as on adherent cells cultured on chamber slides by using the In Situ Cell Death Detection Kit, Fluorescein (Boehringer Mannheim, Indianapolis, Ind.) following the manufacturer's instruction. Slides are then counterstained with 4',6-diamidino-2-phenylindole. Image acquisition is performed with a cooled charge-coupled device camera (Photometrics, Tucson, Ariz.) coupled with a Zeiss Axioscope fluorescent microscope and controlled by a Power Macintosh 710/800. Frames of the nuclei are taken separately and the images are pseudocolored and merged.

FACScan analysis of apoptosis is performed as follows: $10^6$ cells per sample are fixed with 2% paraformaldehyde in PBS (10 min on ice), washed three times with TBS (50 mM Tris.HCl in saline solution, pH 7.5), permeabilized with ice-cold acetone (1 min on ice), and washed twice in TBS and once in distilled water. Staining is performed by incubating cells for 1 hr at 37° C. in 25 μl (final volume) of TUNEL reaction mixture (In Situ Cell Death Detection Kit, Fluorescein; Boehringer Mannheim). Samples are then analyzed by FACScan. Cells with fragmented DNA appear positive. Apoptotic cells are defined on the basis of a negative control represented by cells treated with TUNEL reaction mixture without the enzyme.

DNA contents of cells may also be analyzed by Propidium Iodide (PI) Staining. PI staining is performed as follows: $10^5$ cells are incubated overnight at 4° C. in 0.2 ml of hypotonic fluorochrome solution, containing 50 mg/ml PI (Sigma, St. Louis, Mo.), 0.1% sodium citrate (Sigma), and 0.1% Triton X-100 (Sigma). Analysis is performed with FACScan. Cells with subdiploid DNA content are considered apoptotic cells.

Example 11
Protease Assays

The α2-Macroglobulin(α2M) complex formation assay is used to assay the protease activity of dmADAM in presence or absence of compounds of interest. dmADAM protein from transfected cells is prepared in serum-free medium and concentrated 10-fold using an Amicon Centricon-10 filter (Millipore Corp, Bedford, Mass.). Assays are carried out in 100 mM NaCl, 50 mM Tris (pH 7.4), 10 mM CaCl2, and 0.02% sodium azide. The α2M substrate is added either in the form of fetal bovine serum at a final concentration of 25% or purified α2M at a concentration of 1 µg/µl. Reactions are terminated after incubation at 37° C. for 16 hr by boiling in SDS sample buffer (0.63 ml 1M Tris-HCl, pH 6.8;1.0 ml glycerol; 0.5 ml β-mercaptoethanol; 1.75 ml 20% SDS; 6.12 ml H2O; (10 ml total), store at −20° C. in aliquots). dmADAM/α2M reaction products are detected by immunoblotting with an antibody specific for dmADAM.

Example 12
Gel Mobility-Shift Assay

Myb-binding site oligonucleotides are annealed and then extended with the Klenow fragment in presence of [α-$^{32}$P] dCTP to make double-stranded probes for the assay (Yang and Klessig, Proc. Natl. Acad. Sci. USA (1996) 93:14972–14977). DNA binding reactions are performed in 20 µl of binding buffer (10 mM Tris, pH 8.0/50 mM NaCl/1 mM dithiothreitol/1 mM EDTA/1 µg/µl BSA/10% glycerol) that contain 2 µg of double-stranded poly(dI-dC), 200 ng of the purified recombinant dmMYB protein, in presence or absence of compounds, and 0.5–2 ng of $^{32}$P-labeled probe (10,000–40,000 cpm). After incubation at 4° C. for 30 min, the reaction mixtures are electrophoresed on a 5% polyacrylamide gel in 0.5×Tris.borate.EDTA buffer at 100 V. The gels are then dried and autoradiographed.

Example 13
Autophosphorylation Assay

Cells transfected with dm PI3K are lysed in TNNE buffer (10 mM Tris-HCl (pH 8.0), 150 mM NaCl, 1% Nonidet P-40, and 2 mM EDTA) containing 1 mM sodium orthovanadate, 50 units/ml aprotinin, 0.1 mM phenylmethylsulfonyl fluoride, and 10 mM NaF. Insoluble materials are removed by centrifugation. For immunoprecipitation, the cell lysates are precleared with protein A-Sepharose 4B (Amersham Pharmacia Biotech) for 1 h at 4° C. After removing the beads, the lysates are incubated for 2 h at 4° C. with anti-dmPI3K antibodies and protein-A Sepharose. The immune complex is washed several times with TNNE buffer and then with kinase buffer (20 mM HEPES (pH 7.4), 10 mM MgCl$_2$, and 10 mM MnCl$_2$). Following addition of [γ-32P]ATP (370 kBq, 110 TBq/mmol), the immunoprecipitates are incubated for 30 min at 30° C. and then separated by 7.5% SDS-polyacrylamide gel electrophoresis. The gels are dried and subjected to autoradiography.

What is claimed is:

1. An isolated nucleic acid molecule comprising a nucleotide sequence as set forth in SEQ ID NO:1.

2. The isolated nucleic acid molecule of claim 1 that encodes an amino acid sequence as set forth in SEQ ID NO:2.

3. A vector comprising the nucleic acid molecule of claim 1.

4. A host cell comprising the vector of claim 3.

5. A process for producing a protein comprising culturing host cell of claim 4, under conditions suitable for expression of a protein comprising the amino acid sequence as set forth in SEQ ID NO:2 and recovering said protein.

* * * * *

SEQUENCE LISTING

<160> NUMBER OF SEQ ID NOS: 14

<210> SEQ ID NO 1
<211> LENGTH: 1647
<212> TYPE: DNA
<213> ORGANISM: Drosophila melanogaster

<400> SEQUENCE: 1

```
ttcggcacga gggagagggt ggtaggccga ttccctctcc ccactgcccg ttgaaattca      60
gaatactaag ctctcggtta aacgcggcga aaagaaagc aagctctgag cggctgaaaa      120
aaaaatgaag tgaaataaaa ctgggatcgc ggcaccagca acaagtttta gtggctcttc      180
tttgtgcgtt tcgttcgtgt ttgctgccct gcgctttgct cgccacattc gtcgccgact      240
tttattttgt tttgcccatt ttatcagaat cggagcacct ccaaaaaagc ccaagacgag      300
ctgagcctca gctgcgtcga ggtgagctga tccactccgc tcccctttcg tgcgctgccc      360
accgctcccc accgctcaca cccgatccca tccaatccaa tccgatccgc tccgctccga      420
gtgcatagtg catgcaaagt cgcggggctg ggctttcgga attacacaac ccacatgggg      480
cagcgccaac aaaggcctca gcagcaacaa tagcgggcag ccaagcattg ccctgccctc      540
gacttcgacc atggctccca ccaccagtcc gccacccaag ctggccaagt tcaagtcctc      600
gtcgctggac cacgagatct acacggccaa tcgccgcggc accattgcca cggcctccag      660
cgactggaag gcgctccgcg gaggcgtcgg tggaggagca ggaggacccg gtagcgtacc      720
caatccctct aacggacgct cccttcacgc cggcggaccc atgacacggg ccgcctccac      780
atcctcgctg gctagcagta cgcgcacgat gactaactac caggagtaca aaatggatat      840
catcaaccag gggaaatgtc tgtgtggtca gtacatcaga gcgcggctgc gacgggcagg      900
agtcctcaac cggaaggtga cacagcgttt gcgcaacatc ctggaccccg gctcctcgca      960
```

-continued

```
cgtggtctat gaagttttcc cggcactgaa cagcatgggc gaggaactgg agcggatgca    1020
cccgcgggtg tacacaaaca tatcgcgaca gctgtcgagg gccccgtttg gcgagctgga    1080
ggacagcgac atggcgccca tgttgctcaa cctagttgcc aaggatcttt ttcgctccag    1140
catcacctgg ggcaagataa tctcgatatt tgccgtatgc ggcggctttg ccatagactg    1200
cgtgcgccag ggacatttcg actacctaca gtgcctgatt gacggtctgg ctgagatcat    1260
aggacgacct ggtctactgg ctgatcgaca acggcggatg gttgggcctg tcgcggcaca    1320
tccgaccccg ggtcggcgaa tttacgttct tgggatggtt gacgctgttc gtgactatct    1380
ctgcaggcgc atatatggtc tcaaacgtgt gtcggcgcat ggaggtcaa ctgtattcgc     1440 tgctgttcta gattcgcttg ggatcgcgtc gttaagaaat acaatcgtac catttagtca    1500
atgagagctt caaatcattc ctgcttccat gggcaccagt cgtttagtag tatgtaacgg    1560
accctgtttt acgtataata ttgttattcc ctttctcctc tttttgtaca tacaaggcta    1620
ttctaggcgc aaaaaaaaaa aaaaaaa                                        1647
```

<210> SEQ ID NO 2
<211> LENGTH: 317
<212> TYPE: PRT
<213> ORGANISM: Drosophila melanogaster

<400> SEQUENCE: 2

```
Met Ala Pro Thr Thr Ser Pro Pro Lys Leu Ala Lys Phe Lys Ser
1               5                   10                  15

Ser Ser Leu Asp His Glu Ile Tyr Thr Ala Asn Arg Arg Gly Thr Ile
                20                  25                  30

Ala Thr Ala Ser Ser Asp Trp Lys Ala Leu Arg Gly Val Gly Gly
        35                  40                  45

Gly Ala Gly Gly Pro Gly Ser Val Pro Asn Pro Ser Asn Gly Arg Ser
    50                  55                  60

Leu His Ala Gly Gly Pro Met Thr Arg Ala Ala Ser Thr Ser Ser Leu
65                  70                  75                  80

Ala Ser Ser Thr Arg Thr Met Thr Asn Tyr Gln Glu Tyr Lys Met Asp
                85                  90                  95

Ile Ile Asn Gln Gly Lys Cys Leu Cys Gly Gln Tyr Ile Arg Ala Arg
            100                 105                 110

Leu Arg Arg Ala Gly Val Leu Asn Arg Lys Val Thr Gln Arg Leu Arg
        115                 120                 125

Asn Ile Leu Asp Pro Gly Ser Ser His Val Val Tyr Glu Val Phe Pro
    130                 135                 140

Ala Leu Asn Ser Met Gly Glu Glu Leu Glu Arg Met His Pro Arg Val
145                 150                 155                 160

Tyr Thr Asn Ile Ser Arg Gln Leu Ser Arg Ala Pro Phe Gly Glu Leu
                165                 170                 175

Glu Asp Ser Asp Met Ala Pro Met Leu Leu Asn Leu Val Ala Lys Asp
            180                 185                 190

Leu Phe Arg Ser Ser Ile Thr Trp Gly Lys Ile Ile Ser Ile Phe Ala
        195                 200                 205

Val Cys Gly Gly Phe Ala Ile Asp Cys Val Arg Gln Gly His Phe Asp
    210                 215                 220

Tyr Leu Gln Cys Leu Ile Asp Gly Leu Ala Glu Ile Ile Gly Arg Pro
225                 230                 235                 240

Gly Leu Leu Ala Asp Arg Gln Arg Arg Met Val Gly Pro Val Ala Ala
```

```
                       245                 250                 255
His Pro Thr Pro Gly Arg Arg Ile Tyr Val Leu Gly Met Val Asp Ala
                260                 265                 270

Val Arg Asp Tyr Leu Cys Arg Arg Ile Tyr Gly Leu Lys Arg Val Ser
            275                 280                 285

Ala His Trp Arg Ser Thr Val Phe Ala Ala Val Leu Asp Ser Leu Gly
        290                 295                 300

Ile Ala Ser Leu Arg Asn Thr Ile Val Pro Phe Ser Gln
305                 310                 315
```

<210> SEQ ID NO 3
<211> LENGTH: 624
<212> TYPE: DNA
<213> ORGANISM: Drosophila melanogaster

<400> SEQUENCE: 3

```
ttcggcacga gaaaaaaccc aaaataagta tttcgcttta aaactgttta ttaaaaggat    60
atggaatcgc cagtggtaaa cgaagttgca gccagcttgg gcggtgaaaa gctggaggtc   120
tttcgcaagc tgaacctcct ggaacagcat cgcgtggaga gctacaagag ttggcccttt   180
ccggagaccg catcctgcag catttcgaag atggccgagg cgggattcta ttggacgggc   240
accaagcggg aaaacgacac tgccacttgt tttgtgtgcg gaaagaccct ggatggctgg   300
gagcccgaag atgatccgtg gaaggagcac gtgaaacatg cacccccaatg cgagttcgcc   360
aagctatcgt gtcccgaaag gaatttaacc gtatcacaat ttctggaaat cttggaacc   420
gtcgttaaag gcagcataga gaaacctgc aaagccttca atcgagctt cgttcgggag   480
aatgagaagc gtctagatga gtttacgcgt aatcaaaaat agagcgctaa ttttaaacc   540
ttaaatatac atatataaaa ctcgctattt atcaagattt ttaataaaac gcaatgttag   600
tccaaaaaaa aaaaaaaaaa aaaa                                         624
```

<210> SEQ ID NO 4
<211> LENGTH: 153
<212> TYPE: PRT
<213> ORGANISM: Drosophila melanogaster

<400> SEQUENCE: 4

```
Met Glu Ser Pro Val Val Asn Glu Val Ala Ala Ser Leu Gly Gly Glu
1               5                   10                  15

Lys Leu Glu Val Phe Arg Lys Leu Asn Leu Leu Glu Gln His Arg Val
            20                  25                  30

Glu Ser Tyr Lys Ser Trp Pro Phe Pro Glu Thr Ala Ser Cys Ser Ile
        35                  40                  45

Ser Lys Met Ala Glu Ala Gly Phe Tyr Trp Thr Gly Thr Lys Arg Glu
    50                  55                  60

Asn Asp Thr Ala Thr Cys Phe Val Cys Gly Lys Thr Leu Asp Gly Trp
65                  70                  75                  80

Glu Pro Glu Asp Asp Pro Trp Lys Glu His Val Lys His Ala Pro Gln
                85                  90                  95

Cys Glu Phe Ala Lys Leu Ser Cys Pro Glu Arg Asn Leu Thr Val Ser
            100                 105                 110

Gln Phe Leu Glu Ile Leu Gly Thr Val Val Lys Gly Ser Ile Glu Lys
        115                 120                 125

Thr Cys Lys Ala Phe Lys Ser Ser Phe Val Arg Glu Asn Glu Lys Arg
    130                 135                 140
```

Leu Asp Glu Phe Thr Arg Asn Gln Lys
145                 150

<210> SEQ ID NO 5
<211> LENGTH: 2595
<212> TYPE: DNA
<213> ORGANISM: Drosophila melanogaster

<400> SEQUENCE: 5

| | | | | | |
|---|---|---|---|---|---|
| ttcggcacga | ggcccatcgc | tatcaaaaag | aaatttagt | gctgagttaa | gaattttcc | 60 |
| cttttttgc | acagtttacg | cggtttttat | aaacaagggg | cgtaatagag | ctcaaggcag | 120 |
| ggtataaaac | agtcaatagg | gttaaaagtt | gcaaccctaa | aacgtcttac | aaaagagaat | 180 |
| actcgcagga | aaaaccaaca | acaatgcaca | tatagctgcc | cgtgcgtctg | tgtgtgtgcg | 240 |
| ttgtatgtgc | gttttttttt | gtttatttgg | caaattcggt | ggcctacgtg | attaaaataa | 300 |
| gcacaaacag | tcttaagtga | aatgttggct | aaaacgcccg | agtgccgtaa | ttcgcattga | 360 |
| taacaaatag | ccataatctg | cgagcgtgtg | tgtgtgtgat | tgcctcagtt | ggcgtaggtg | 420 |
| aggtggggta | aaaaaagctg | ggagagctgt | caaggttaaa | atcggtcgtc | gcctttggct | 480 |
| ctcctctccc | gcaaaatgca | atgagcaggg | gtcgcggaaa | ggtcagggat | tcagcaagcc | 540 |
| attccggctc | ccactccgca | tccaaatcgg | ccatggaccc | gccgcgctgc | tccatctgcg | 600 |
| gcactcagca | gcaactactg | cgctgcgcca | agtgcaaggc | cgtctactac | tgctccccg | 660 |
| ctcaccagca | tctccattgg | cccgaccacc | gcaccgagtg | ccgcctcctg | acccgccaaa | 720 |
| agctcaacag | cagcaacaac | aataagcagc | agcagcggca | gcagatccag | caactgcaac | 780 |
| aagctgtggc | atctgccaat | ctggaatgca | gcggcgccgg | cgccaactgc | tccaccgccc | 840 |
| agatgatgac | gcctgcccac | caggcgcaga | gttggcccgc | cgaggtagac | aacctgctga | 900 |
| atctcctcgg | gcagccgggc | agccaggaga | aggctgcagc | tgcggaaacg | gaaacaggtc | 960 |
| aaaggcagca | gcagcaccag | catcatcacc | ataatggcga | aaagagctcc | agctatcaaa | 1020 |
| tcggtctggc | ggatgccagc | ttcatgggat | caggaagtga | gcgccgctat | gaggatctgt | 1080 |
| gccgtaacat | catcagcgac | atgaaccagt | atggtctgtc | cgtggtggac | gacttcctgg | 1140 |
| ggatggagac | gggcctgaag | atcctcaacg | aggttcgaag | catgtacaac | gcaggagcct | 1200 |
| tccaggatgg | ccaagtggtg | accaaccaga | cgcccgatgc | accgcggtg | cgcggtgaca | 1260 |
| agatccgagg | cgataagatc | aagtgggttg | gtggcaatga | gccgggctgc | agcaatgtct | 1320 |
| ggtatctgac | caatcagatt | gactctgtgg | tgtatcgtgt | taacacgatg | aaggataatg | 1380 |
| gcatcttggg | caactaccac | atcagggagc | gcacgagggc | aatggtcgct | tgttatccgg | 1440 |
| gatcgggaac | tcactacgtc | atgcatgtgg | acaatcccca | aaaggatggc | cgcgttataa | 1500 |
| cggccatata | ctacctgaat | atcaactggg | atgcgcggga | aagtggcggc | attctgcgaa | 1560 |
| ttcggccaac | acccggaacc | acagtggcgg | atattgagcc | caagtttgat | cgcctgatat | 1620 |
| tcttctggtc | tgacattcgg | aatccccacg | aagtgcagcc | cgctcaccgt | acccgctatg | 1680 |
| ccatcaccgt | ctggtacttc | gatgccaagg | aacgcgagga | ggccctcatt | agggccaagc | 1740 |
| tggaaaacag | caagacgaac | aatctggcag | ctcaagccca | agcccaacag | gctgaaccag | 1800 |
| actccaccac | cacaccaccc | gcagcaccag | cttcatccgc | atccagtctg | ccggttagca | 1860 |
| tgtccacggg | aacgggagcg | ctgaacgcca | atgtgtcgag | taattcctgc | gccaccagca | 1920 |
| gcgaaatatg | cacgtaaccc | aagccgacag | cgcagctaaa | ggcaaccaaa | aagtgtaaat | 1980 |
| tattttcaac | caaacacaca | tgtataaagc | tagttaaaaa | ctatttatag | cttcggaggg | 2040 |

-continued

```
gcggcagcgc aagcccgcat tgcgaaagtt aatcaaagct cctttagtcg ttaagccttc    2100
tagtttagtc tctaagtcgt acccttagtc attttcgcat taaccattag cttactgcca    2160
tgtcagcgtc cgagttggtt gtttattaat tttagtttgt tgcatctttg tcaggacctt    2220
ttgcctagct cattcttagt ttttggctgc caaagtatta tacctaaaga gaagttaact    2280
agattcaata acataagcaa ctgtcgcgac gctcattgca tcttatctca aaattattta    2340
acaagccagt aaatcgtgga caaacgcggt cactggctaa cactcaatct gtcgactctc    2400
atgcatcttg ttagacatct ttttcatatc gtttacatct aataacaaac ggaaataaat    2460
gtttgtccaa atacgttctc ttgttatctg taaatcatga agtatgtata tttatgacat    2520
atctacatat tgtatgtata ttttttatat taaacaaaag cctgagctga tgaaaaaaaa    2580
aaaaaaaaaa aaaaa                                                     2595
```

<210> SEQ ID NO 6
<211> LENGTH: 478
<212> TYPE: PRT
<213> ORGANISM: Drosophila melanogaster

<400> SEQUENCE: 6

```
Met Ser Arg Gly Arg Gly Lys Val Arg Asp Ser Ala Ser His Ser Gly
 1               5                  10                  15

Ser His Ser Ala Ser Lys Ser Ala Met Asp Pro Arg Cys Ser Ile
            20                  25                  30

Cys Gly Thr Gln Gln Gln Leu Leu Arg Cys Ala Lys Cys Lys Ala Val
        35                  40                  45

Tyr Tyr Cys Ser Pro Ala His Gln His Leu His Trp Pro Asp His Arg
    50                  55                  60

Thr Glu Cys Arg Leu Leu Thr Arg Gln Lys Leu Asn Ser Ser Asn Asn
65                  70                  75                  80

Asn Lys Gln Gln Gln Arg Gln Gln Ile Gln Gln Leu Gln Gln Ala Val
                85                  90                  95

Ala Ser Ala Asn Leu Glu Cys Ser Gly Ala Gly Ala Asn Cys Ser Thr
            100                 105                 110

Ala Gln Met Met Thr Pro Ala His Gln Ala Gln Ser Trp Pro Ala Glu
        115                 120                 125

Val Asp Asn Leu Leu Asn Leu Leu Gly Gln Pro Gly Ser Gln Glu Lys
    130                 135                 140

Ala Ala Ala Ala Glu Thr Glu Thr Gly Gln Arg Gln Gln Gln His Gln
145                 150                 155                 160

His His His His Asn Gly Glu Lys Ser Ser Tyr Gln Ile Gly Leu
                165                 170                 175

Ala Asp Ala Ser Phe Met Gly Ser Gly Ser Glu Arg Arg Tyr Glu Asp
            180                 185                 190

Leu Cys Arg Asn Ile Ile Ser Asp Met Asn Gln Tyr Gly Leu Ser Val
        195                 200                 205

Val Asp Asp Phe Leu Gly Met Glu Thr Gly Leu Lys Ile Leu Asn Glu
    210                 215                 220

Val Arg Ser Met Tyr Asn Ala Gly Ala Phe Gln Asp Gly Gln Val Val
225                 230                 235                 240

Thr Asn Gln Thr Pro Asp Ala Pro Ala Val Arg Gly Asp Lys Ile Arg
                245                 250                 255

Gly Asp Lys Ile Lys Trp Val Gly Gly Asn Glu Pro Gly Cys Ser Asn
            260                 265                 270
```

Val Trp Tyr Leu Thr Asn Gln Ile Asp Ser Val Val Tyr Arg Val Asn
                275                 280                 285

Thr Met Lys Asp Asn Gly Ile Leu Gly Asn Tyr His Ile Arg Glu Arg
            290                 295                 300

Thr Arg Ala Met Val Ala Cys Tyr Pro Gly Ser Gly Thr His Tyr Val
305                 310                 315                 320

Met His Val Asp Asn Pro Gln Lys Asp Gly Arg Val Ile Thr Ala Ile
                325                 330                 335

Tyr Tyr Leu Asn Ile Asn Trp Asp Ala Arg Glu Ser Gly Gly Ile Leu
            340                 345                 350

Arg Ile Arg Pro Thr Pro Gly Thr Thr Val Ala Asp Ile Glu Pro Lys
                355                 360                 365

Phe Asp Arg Leu Ile Phe Phe Trp Ser Asp Ile Arg Asn Pro His Glu
            370                 375                 380

Val Gln Pro Ala His Arg Thr Arg Tyr Ala Ile Thr Val Trp Tyr Phe
385                 390                 395                 400

Asp Ala Lys Glu Arg Glu Glu Ala Leu Ile Arg Ala Lys Leu Glu Asn
                405                 410                 415

Ser Lys Thr Asn Asn Leu Ala Ala Gln Ala Gln Ala Gln Gln Ala Glu
            420                 425                 430

Pro Asp Ser Thr Thr Thr Pro Pro Ala Ala Pro Ala Ser Ser Ala Ser
                435                 440                 445

Ser Leu Pro Val Ser Met Ser Thr Gly Thr Gly Ala Leu Asn Ala Asn
            450                 455                 460

Val Ser Ser Asn Ser Cys Ala Thr Ser Ser Glu Ile Cys Thr
465                 470                 475

<210> SEQ ID NO 7
<211> LENGTH: 3994
<212> TYPE: DNA
<213> ORGANISM: Drosophila melanogaster

<400> SEQUENCE: 7

| | | | | | |
|---|---|---|---|---|---|
| ttcggcacga | ggtcaaaagc | acaccccgtc | ctcgaggagt | tctcaactta | cactgtgata | 60 |
| cgaccgcagg | tggaacatgg | acgcactaag | cgcagcctgc | taaccactct | ggatgccacc | 120 |
| gacggccttc | acacgccgca | gattagcctg | agttacaccc | acgagggcaa | gcgggtcgtc | 180 |
| gtcgacctgc | agcgcaacga | tctcctcctg | ccgaattccc | acttcctgcg | ctaccaaaat | 240 |
| gccagcagag | gagccactcc | tggccatgtg | gttacccct | ttaccaagac | tgaggttgat | 300 |
| ttatgccatt | atcagggaca | cattcgtggt | aaaccagaat | ctgtggtagc | actctccacc | 360 |
| tgtgatggtg | ctctggatgg | catcgtaatc | gatggcaggc | agacgtactt | cattcatccc | 420 |
| catatcgacg | gcagggggcg | attgcaggat | gaccactatc | tgcttaagca | ggcagacatg | 480 |
| catccgacga | acgccacctg | tggctatgat | aaccacaggg | acgaccatag | tcacgactac | 540 |
| gaaaaggctg | acgggataa | cggacttgga | ggagggattc | cttcactgcc | actccgcctt | 600 |
| gatggcggag | aattctcgag | gaccctgctc | cggaagaggc | gtcaggcgga | cgatagcagt | 660 |
| caattgatcc | ggccttacaa | tgccaacaaa | tactccagct | acgtggagct | ggtcatcgtt | 720 |
| gtggacaata | aggtttacaa | aaatttccaa | gagaacacca | agaaggtgca | ccagtattgc | 780 |
| aaaggcattg | ccaatataat | caatgcgctc | tatgtcccct | gaatatatt | tgtggcgctg | 840 |
| gtgggtgtgg | tgatttggaa | cgagagcaac | gaaatcgagt | ctccagcga | cggcgacctg | 900 |
| acactgcgaa | atttttgaa | ctaccgtagc | accaagctgg | tgctggatca | tcctaacgat | 960 |

```
aatgcccagc tgctgaccaa ggagaacttc gccggcggtg tggtgggcaa ggcactgaag    1020
ggtcccatct gcacgtacga gtactccggc ggagtgagca tgcagcacag tcctaacccg    1080
gcaatggtgg ccacaacaat ggcccacgag atggggcaca actttggcat ggagcacgat    1140
acatcggatt gtcattgtcg ggatgagaag tgtgtgatgg ctgcctcgag tacctcgttt    1200
attccagtta actggagcag ctgcagcatt gatcagctca caatagcctt ctcgcgcgga    1260
atgaactact gcctgaggaa caagccggaa aggttgttcg aatcaccgac ctgtggcaat    1320
ggtttcgtgg agcctggtga acagtgcgat tgcggattac ccgagcactg tgaaaatgcc    1380
tgttgcaatg ctcagacctg catgttgcac tctaaaaatg ccacctgtgc taccggagaa    1440
tgctgtgatc tgaccacatg tcgacccaaa ttggcgggca gtgcctgtcg agaggctgaa    1500
aacgagtgcg atttaccaga gtactgcacc ggggaatctg agtactgtcc ggcggatgtc    1560
ttccggcggg acacggagcc atgcgacggc ggtcaagcat actgcttcca cggcacatgt    1620
cgatctcact ccaatcagtg tcgaacattg tggggaccca cgggtgataa ctcggagcat    1680
tgctacaaca agaacacgga gggcactagg ctaggaaatt gcggctataa cagactgaac    1740 aagaccttt tgcgctgcga agagcagcat gtcaattgcg gaatgctcca ctgcatccac    1800
ttaaacgaac gactcgaatt cggtatgaa tcggcggctg tgctatccca ttcctatata    1860
agtcacgatc gcaagattgt cgcttgtcgc actgccttgg tggatctggg tttgcagacc    1920
accgatcccg gccttacgcc caatggagcc aaatgcggcg tggataagat gtgtgtggat    1980
cagcgttgcc tgccggtgga cgcggttcgg cagaagggca tgggaaagcc atgtccggag    2040
gattgcaatg gcaatggcat ctgcaacagt cgaggccact gccactgcga tgtaggattc    2100
ggtggggaat cgtgctcgaa ggcaggatct ggaggttccc cggacagtgg accagccaca    2160
gatccaaatg gttccgtggg cttcaagcga ttcctttacg tgctgttctt ctttgtgctg    2220
cccgttgtgg ccctcttttg gttcctctat cactgctaca agaacggcat gctgacgcgc    2280
ggaaaactgg cggacaatat gtatgtatcg acctcctcct tcagcattgg ctcgaaagag    2340
gacaccagtc ccgacagcag tatctccacc acactagcac ataaacagac ccctgcacgc    2400
actgcaccac ctccactacc actgcacacc aatcgccagc tttctggtat tgtaactaac    2460
acggctccgg ccaccattac taacatacac gccatcctgc cgcgccacaa gtccaatcca    2520
gatgtagtgc atcagttaaa tattccgccg ccctctgtgc caaaaagcca tagcactcat    2580
gaggtgcgac caaaggcggc caccttgaaa cctctaactc tcctgcactc cacgcactca    2640
acctccaata caacaacac tgagtcactt aaccagaatg acaagagcaa cacgaacaac    2700
agcacactga gacgcaagct ggatatcacg gctccgcggc tgaatgccac cacaaacccca    2760 ctggcactca ccgagggcgc ccagttcata cagagcgacc ccgcgaggtg tgccaaaaac    2820
taaaccagca caattaacta cagtgaaata cgcttgcact gccacagaaa tacagcatga    2880
ctttgcgctt ggcccatggc atttcaatat cattgcagaa tttttttattt ttatattgac    2940 ctcgaaatca aatgggttca gtgttgcaga ttacgaatta ttaggatagg ttctttttg    3000 tattatttt cttatataca ttaatatagt cgttatattg agaaatacac aatcctagat    3060
tgagaaaaaa gagaacacaa atagaatata cgtgatttag tgaaagtatt taggattttt    3120
ttttaatctg caatggtata tctataattt gaaaaaccga agacaactct tcattttcgt    3180
tcacattttt gtgttaatgc ctcattaaca atcaattaac ccacaatccc cactaacata    3240
gtccataatt tgaatttgtt cctagttta tttttcctaa ttttgtatgt tctgcaaata    3300
aatgtgactc tttaaaaaaa aaaaaaaaaa aaaaaaaaaa aaaaaaaaaa aaaaaaaaaa    3360
```

-continued

```
aaaaaaaaaa acccggggtt ttttagggcc ccctaaatgg ttggggttta aaccataggg    3420
ttttgtttaa atgggagccg ggttttaacg tgaacgtcca atttaccccc cggccttgcc    3480
attaatggaa gaccggtgga aattaataaa ccattttgcc gcctgggaac ccttcccaac    3540
cggtttgatg accctgattc gccaggggat taagcccctt ggcggccttg ggtaaaaaat    3600
tggcccaggg ggaaaccggg gggccaaaaa attgcccttt tgcccccgt ttaattaaaa    3660
attggggaaa cttcacccgg gatgggttga acaaaaaaa atattttaaa taaccccta     3720
agggaaaaag gcgggttttc accgaacccc cccattttgg aaattttgtg agaacctgcg    3780
gaaaatgttg gggttttctt ccagaggatg aaacctttat ttgtgtattg aaaacgggtt    3840
aaagggtga ccctttccca ttaccagttc accgtttttt tggcataggg actccgatga    3900
gctttcatta gggggcaaaa tgggaataag gccggtaaaa acttggctta tttttttag    3960
cggctttaaa agccgcatat tccgtttgaa gggg                                3994
```

<210> SEQ ID NO 8
<211> LENGTH: 781
<212> TYPE: PRT
<213> ORGANISM: Drosophila melanogaster

<400> SEQUENCE: 8

```
Met His Pro Thr Asn Ala Thr Cys Gly Tyr Asp Asn His Arg Asp Asp
 1               5                  10                  15

His Ser His Asp Tyr Glu Lys Ala Asp Gly Asp Asn Gly Leu Gly Gly
             20                  25                  30

Gly Ile Pro Ser Leu Pro Leu Arg Leu Asp Gly Gly Glu Phe Ser Arg
         35                  40                  45

Thr Leu Leu Arg Lys Arg Arg Gln Ala Asp Asp Ser Ser Gln Leu Ile
     50                  55                  60

Arg Pro Tyr Asn Ala Asn Lys Tyr Ser Ser Tyr Val Glu Leu Val Ile
 65                  70                  75                  80

Val Val Asp Asn Lys Val Tyr Lys Leu Asn Phe Gln Glu Asn Thr Lys Lys
                 85                  90                  95

Val His Gln Tyr Cys Lys Gly Ile Ala Asn Ile Ile Asn Ala Leu Tyr
            100                 105                 110

Val Pro Leu Asn Ile Phe Val Ala Leu Val Gly Val Ile Trp Asn
        115                 120                 125

Glu Ser Asn Glu Ile Glu Phe Ser Ser Asp Gly Asp Leu Thr Leu Arg
    130                 135                 140

Asn Phe Leu Asn Tyr Arg Ser Thr Lys Leu Val Leu Asp His Pro Asn
145                 150                 155                 160

Asp Asn Ala Gln Leu Leu Thr Lys Glu Asn Phe Ala Gly Gly Val Val
                165                 170                 175

Gly Lys Ala Leu Lys Gly Pro Ile Cys Thr Tyr Glu Tyr Ser Gly Gly
            180                 185                 190

Val Ser Met Gln His Ser Pro Asn Pro Ala Met Val Ala Thr Thr Met
        195                 200                 205

Ala His Glu Met Gly His Asn Phe Gly Met Glu His Asp Thr Ser Asp
    210                 215                 220

Cys His Cys Arg Asp Glu Lys Cys Val Met Ala Ala Ser Ser Thr Ser
225                 230                 235                 240

Phe Ile Pro Val Asn Trp Ser Ser Cys Ser Ile Asp Gln Leu Thr Ile
                245                 250                 255
```

-continued

```
Ala Phe Ser Arg Gly Met Asn Tyr Cys Leu Arg Asn Lys Pro Glu Arg
            260                 265                 270

Leu Phe Glu Ser Pro Thr Cys Gly Asn Gly Phe Val Glu Pro Gly Glu
            275                 280                 285

Gln Cys Asp Cys Gly Leu Pro Glu His Cys Glu Asn Ala Cys Cys Asn
            290                 295                 300

Ala Gln Thr Cys Met Leu His Ser Lys Asn Ala Thr Cys Ala Thr Gly
305                 310                 315                 320

Glu Cys Cys Asp Leu Thr Thr Cys Arg Pro Lys Leu Ala Gly Ser Ala
                    325                 330                 335

Cys Arg Glu Ala Glu Asn Glu Cys Asp Leu Pro Glu Tyr Cys Thr Gly
                340                 345                 350

Glu Ser Glu Tyr Cys Pro Ala Asp Val Phe Arg Arg Asp Thr Glu Pro
            355                 360                 365

Cys Asp Gly Gly Gln Ala Tyr Cys Phe His Gly Thr Cys Arg Ser His
            370                 375                 380

Ser Asn Gln Cys Arg Thr Leu Trp Gly Pro Thr Gly Asp Asn Ser Glu
385                 390                 395                 400

His Cys Tyr Asn Lys Asn Thr Glu Gly Thr Arg Leu Gly Asn Cys Gly
                    405                 410                 415

Tyr Asn Arg Leu Asn Lys Thr Phe Leu Arg Cys Glu Glu Gln His Val
                420                 425                 430

Asn Cys Gly Met Leu His Cys Ile His Leu Asn Glu Arg Leu Glu Phe
            435                 440                 445

Gly Met Glu Ser Ala Ala Val Leu Ser His Ser Tyr Ile Ser His Asp
450                 455                 460

Arg Lys Ile Val Ala Cys Arg Thr Ala Leu Val Asp Leu Gly Leu Gln
465                 470                 475                 480

Thr Thr Asp Pro Gly Leu Thr Pro Asn Gly Ala Lys Cys Gly Val Asp
                    485                 490                 495

Lys Met Cys Val Asp Gln Arg Cys Leu Pro Val Asp Ala Val Arg Gln
                500                 505                 510

Lys Gly Met Gly Lys Pro Cys Pro Glu Asp Cys Asn Gly Asn Gly Ile
            515                 520                 525

Cys Asn Ser Arg Gly His Cys His Cys Asp Val Gly Phe Gly Gly Glu
            530                 535                 540

Ser Cys Ser Lys Ala Gly Ser Gly Gly Ser Pro Asp Ser Gly Pro Ala
545                 550                 555                 560

Thr Asp Pro Asn Gly Ser Val Gly Phe Lys Arg Phe Leu Tyr Val Leu
                    565                 570                 575

Phe Phe Phe Val Leu Pro Val Val Ala Leu Phe Trp Phe Leu Tyr His
                580                 585                 590

Cys Tyr Lys Asn Gly Met Leu Thr Arg Gly Lys Leu Ala Asp Asn Met
            595                 600                 605

Tyr Val Ser Thr Ser Ser Phe Ser Ile Gly Ser Lys Glu Asp Thr Ser
            610                 615                 620

Pro Asp Ser Ser Ile Ser Thr Thr Leu Ala His Lys Gln Thr Pro Ala
625                 630                 635                 640

Arg Thr Ala Pro Pro Pro Leu Pro Leu His Thr Asn Arg Gln Leu Ser
                    645                 650                 655

Gly Ile Val Thr Asn Thr Ala Pro Ala Thr Ile Thr Asn Ile His Ala
                660                 665                 670

Ile Leu Pro Arg His Lys Ser Asn Pro Asp Val Val His Gln Leu Asn
```

|     | 675 |     |     |     | 680 |     |     |     | 685 |     |     |
| --- | --- | --- | --- | --- | --- | --- | --- | --- | --- | --- | --- |
| Ile | Pro | Pro | Ser | Val | Pro | Lys | Ser | His | Ser | Thr | His | Glu | Val | Arg |
|     |     |     | 690 |     |     |     |     | 695 |     |     |     | 700 |

Pro Lys Ala Ala Thr Leu Lys Pro Leu Thr Leu Leu His Ser Thr His
705                710                715                720

Ser Thr Ser Asn Asn Asn Asn Thr Glu Ser Leu Asn Gln Asn Asp Lys
               725                730                735

Ser Asn Thr Asn Asn Ser Thr Leu Arg Arg Lys Leu Asp Ile Thr Ala
           740                745                750

Pro Arg Leu Asn Ala Thr Thr Asn Pro Leu Ala Leu Thr Glu Gly Ala
           755                760                765

Gln Phe Ile Gln Ser Asp Pro Ala Arg Cys Ala Lys Asn
770                775                780

<210> SEQ ID NO 9
<211> LENGTH: 2242
<212> TYPE: DNA
<213> ORGANISM: Drosophila melanogaster

<400> SEQUENCE: 9

| ttcggcacga | ggtgaaactg | cggttgagcc | tggaagaagc | taagagtac | ccaggcagga | 60 |
| gtgtccatgcg | gcgccagcgc | atcaaggctc | cggccaacct | gtcgcttatc | aaacgcaagc | 120 |
| cacgcaggga | ggagctccca | acggcgaaaa | aggaggatga | ggaggaggag | gcggtggtgg | 180 |
| tggaagcaga | ggctgagtcc | ccgccgttg | catcgacccc | tgctgcggaa | ttggaactag | 240 |
| aggctgatgc | aatcgccttc | aagatgcccg | caagctcggc | tgggcagctg | aagaggtat | 300 |
| tccactcgga | cctcgaggac | aatgtcattc | agatggactt | gcagaagacc | accaatggct | 360 |
| tccctatgtc | gcccagcaag | gctcaagccc | gtcagcgtgt | gcgacccact | ccggtatttg | 420 |
| gccagcgacg | caacagcttc | gtgggctcac | ccatggccag | tgattatgag | ggcgactatc | 480 |
| agtcgccagc | cacgcccacg | cggcgagagc | gctatcttag | cggttcttca | tcgggaactc | 540 |
| ctttgcagca | gcaggtgcac | tcgcctatgc | ctccgtcccc | ctataaatac | ctaccgcccg | 600 |
| ctagtccggg | catgggacgc | attcgcaccg | aatccacctg | ttccacctat | tccgaaggag | 660 |
| gtagcaagca | gaggaagggc | gacgataggt | cgcaaagtca | aattggacag | cggttaaatg | 720 |
| cccggcgaga | ctttgaaacc | cgtttcaata | agggtgtacc | cgacaagtcc | acgttcaaga | 780 |
| tgatggacat | gatcttctac | aatccggaga | acaatcccat | ggtgcccaaa | cagtcggtga | 840 |
| cgaccatcaa | ggatgagtct | ggtggcgatg | attccaagcc | cgcagtcagt | caactattgg | 900 |
| aacccaaggg | agagtccaca | tccgctatgt | tagtgcctca | gctaaagctt | gatgccaatg | 960 |
| gcgagatgat | cattgatgag | aaaacattgg | agatcgaaac | cacggccgag | gtggaggccc | 1020 |
| gcaaggtgct | agccaactca | tcgttaatcc | taatggacga | gactacggga | gataatggat | 1080 |
| tctataaacg | ccacaagcgc | acgccatact | ggacctccga | tgagaccgtc | cgcttctacc | 1140 |
| gcagcctgca | gatcattggg | acggacttct | cgctgatgtg | ccaaatgttt | ccaacacgtt | 1200 |
| cacgtcggga | tctaaagctg | aagtacaaaa | aggaagagcg | aaccaatggg | cagctcataa | 1260 |
| acaaagcact | cctctatcct | aaggccttca | acattcagga | gctcaaggat | caactggaag | 1320 |
| aggaggaccg | cgaaagggaa | gaaaatgatc | gcaagtggag | ggaaatcgca | cgagctcttc | 1380 |
| cgggaaaccc | taagaagcgt | tcccgagtac | agcagcaaag | caaggcctca | agggcactaa | 1440 |
| acgatggtga | tgttgtctac | gaaaacgagc | acgtaacgag | tacaaagctc | ggcaagcacg | 1500 |
| cctgggccaa | aaggcgaaag | gagttggaga | ccgatgagaa | cgacggaagt | gcgccggcca | 1560 |

-continued

```
aacgtaagcc aaaggctaag cgacgatctc ccaaggtttc agttccagcg gcaacggaaa    1620
gcctgtctga tgtggcggcc attaagcagg aaaaaacgat caaaaccgaa caaacgagta    1680
gtcatttgcc aacgggggga gaactgcagg ctgagctcaa tggcctcctc atggatgatc    1740
cggtggaata tgacgtagat gtaaacaagc cacgtgataa aactattatc aatatggatg    1800
atggtaccct aagctatgtc agcgacgtcg aacccgcccc agagacgccc aatcgaaagg    1860
cagagacata tttaataaac ttcattgaag accaagatca tgaacttata cgccggatg     1920 accccattcc gccgtccact accgaaccgg atatcgaaca aattctcgcc gagcttgcgg    1980
aaggatctct ggctctcgtc tcgtccttgg atccagagca cgaggatcgt gtgctcaacg    2040
aaatctacat gctggacaaa aaacgggcg agttgtgcga aacgcctctg aaaataccag     2100
agcatattgt tcaatgcata atgaatgtta tgcagccaga ggactaacga cattttatat    2160
ttatatctta agagtatttg ttaacagtta taatttatta aagcatttcg ctagatgtat    2220
ttacaaaaaa aaaaaaaaaa aa                                             2242
```

<210> SEQ ID NO 10
<211> LENGTH: 695
<212> TYPE: PRT
<213> ORGANISM: Drosophila melanogaster

<400> SEQUENCE: 10

```
Met Ser Met Arg Arg Gln Arg Ile Lys Ala Pro Ala Asn Leu Ser Leu
1               5                   10                  15

Ile Lys Arg Lys Pro Arg Arg Glu Glu Leu Pro Thr Ala Lys Lys Glu
            20                  25                  30

Asp Glu Glu Glu Ala Val Val Glu Ala Glu Ala Ser Pro
        35                  40                  45

Pro Val Ala Ser Thr Pro Ala Ala Glu Leu Glu Leu Glu Ala Asp Ala
    50                  55                  60

Ile Ala Phe Lys Met Pro Ala Ser Ser Ala Gly Gln Leu Glu Glu Val
65                  70                  75                  80

Phe His Ser Asp Leu Glu Asp Asn Val Ile Gln Met Asp Leu Gln Lys
                85                  90                  95

Thr Thr Asn Gly Phe Pro Met Ser Pro Ser Lys Ala Gln Ala Arg Gln
            100                 105                 110

Arg Val Arg Pro Thr Pro Val Phe Gly Gln Arg Arg Asn Ser Phe Val
        115                 120                 125

Gly Ser Pro Met Ala Ser Asp Tyr Glu Gly Asp Tyr Gln Ser Pro Ala
    130                 135                 140

Thr Pro Thr Arg Arg Glu Arg Tyr Leu Ser Gly Ser Ser Ser Gly Thr
145                 150                 155                 160

Pro Leu Gln Gln Gln Val His Ser Pro Met Pro Pro Ser Pro Tyr Lys
                165                 170                 175

Tyr Leu Pro Pro Ala Ser Pro Gly Met Gly Arg Ile Arg Thr Glu Ser
            180                 185                 190

Thr Cys Ser Thr Tyr Ser Glu Gly Gly Ser Lys Gln Arg Lys Gly Asp
        195                 200                 205

Asp Arg Ser Gln Ser Gln Ile Gly Gln Arg Leu Asn Ala Arg Arg Asp
    210                 215                 220

Phe Glu Thr Arg Phe Asn Lys Gly Val Pro Asp Lys Ser Thr Phe Lys
225                 230                 235                 240

Met Met Asp Met Ile Phe Tyr Asn Pro Glu Asn Asn Pro Met Val Pro
```

-continued

```
                245                 250                 255
Lys Gln Ser Val Thr Thr Ile Lys Asp Glu Ser Gly Gly Asp Asp Ser
            260                 265                 270
Lys Pro Ala Val Ser Gln Leu Leu Glu Pro Lys Gly Glu Ser Thr Ser
            275                 280                 285
Ala Met Leu Val Pro Gln Leu Lys Leu Asp Ala Asn Gly Glu Met Ile
            290                 295                 300
Ile Asp Glu Lys Thr Leu Glu Ile Glu Thr Thr Ala Glu Val Glu Ala
305                 310                 315                 320
Arg Lys Val Leu Ala Asn Ser Ser Leu Ile Leu Met Asp Glu Thr Thr
                325                 330                 335
Gly Asp Asn Gly Phe Tyr Lys Arg His Lys Arg Thr Pro Tyr Trp Thr
            340                 345                 350
Ser Asp Glu Thr Val Arg Phe Tyr Arg Ser Leu Gln Ile Ile Gly Thr
            355                 360                 365
Asp Phe Ser Leu Met Cys Gln Met Phe Pro Thr Arg Ser Arg Arg Asp
            370                 375                 380
Leu Lys Leu Lys Tyr Lys Lys Glu Glu Arg Thr Asn Gly Gln Leu Ile
385                 390                 395                 400
Asn Lys Ala Leu Leu Tyr Pro Lys Ala Phe Asn Ile Gln Glu Leu Lys
                405                 410                 415
Asp Gln Leu Glu Glu Glu Asp Arg Glu Arg Glu Glu Asn Asp Arg Lys
            420                 425                 430
Trp Arg Glu Ile Ala Arg Ala Leu Pro Gly Asn Pro Lys Lys Arg Ser
            435                 440                 445
Arg Val Gln Gln Gln Ser Lys Ala Ser Arg Ala Leu Asn Asp Gly Asp
            450                 455                 460
Val Val Tyr Glu Asn Glu His Val Thr Ser Thr Lys Leu Gly Lys His
465                 470                 475                 480
Ala Trp Ala Lys Arg Arg Lys Glu Leu Glu Thr Asp Glu Asn Asp Gly
                485                 490                 495
Ser Ala Pro Ala Lys Arg Lys Pro Lys Ala Lys Arg Arg Ser Pro Lys
            500                 505                 510
Val Ser Val Pro Ala Ala Thr Glu Ser Leu Ser Asp Val Ala Ala Ile
            515                 520                 525
Lys Gln Glu Lys Thr Ile Lys Thr Glu Gln Thr Ser Ser His Leu Pro
            530                 535                 540
Thr Gly Gly Glu Leu Gln Ala Glu Leu Asn Gly Leu Leu Met Asp Asp
545                 550                 555                 560
Pro Val Glu Tyr Asp Val Asp Val Asn Lys Pro Arg Asp Lys Thr Ile
                565                 570                 575
Ile Asn Met Asp Asp Gly Thr Leu Ser Tyr Val Ser Val Glu Pro
            580                 585                 590
Ala Pro Glu Thr Pro Asn Arg Lys Ala Glu Thr Tyr Leu Ile Asn Phe
            595                 600                 605
Ile Glu Asp Gln Asp His Glu Leu Ile Thr Pro Asp Asp Pro Ile Pro
            610                 615                 620
Pro Ser Thr Thr Glu Pro Asp Ile Glu Gln Ile Leu Ala Glu Leu Ala
625                 630                 635                 640
Glu Gly Ser Leu Ala Leu Val Ser Ser Leu Asp Pro Glu His Glu Asp
                645                 650                 655
Arg Val Leu Asn Glu Ile Tyr Met Leu Asp Lys Lys Thr Gly Glu Leu
            660                 665                 670
```

Cys Glu Thr Pro Leu Lys Ile Pro Glu His Ile Val Gln Cys Ile Met
            675                 680                 685

Asn Val Met Gln Pro Glu Asp
            690                 695

<210> SEQ ID NO 11
<211> LENGTH: 5706
<212> TYPE: DNA
<213> ORGANISM: Drosophila melanogaster

<400> SEQUENCE: 11

| | | | | | |
|---|---|---|---|---|---|
| atggtgccag | attctgtcaa | acggctgttt | gacatccatc | aaaacggcac | agcagtactc        60 |
| cttcttttcg | aacgccttta | caatgcgctc | aacaagccgg | tggcattgct | cagttgttca       120 |
| atggttgaaa | caaactgat | gggcagggat | cagtacggcc | tcgtacagta | caaacactgt       180 |
| tctgcggtta | agagtggagg | agagtggggt | tacattttcc | gtgctgatcc | atcgacgcga       240 |
| tccggacctg | gcggccaagg | gcccagaggt | cgaacggtaa | cgctgctgac | tgtggacgat       300 |
| gacgaagagg | aggccgcctc | ggtcagcaag | agatcagcaa | gtgagaacgg | cagtcagtta       360 |
| gaacacgcaa | gtgaaagtgg | cagtcagttg | gaactcgcaa | gtgagaacgg | cagtgagcta       420 |
| gaaaacgcat | gtatgaacgc | gcagacagtg | aataaggagt | acgggagtga | aaacacgtgc       480 |
| gttatgctat | aaaaatggc | gatgcgtccc | gagatctggc | ctcaaccatt | tgatattaag       540 |
| cttaattggc | ttgataaagt | tcttgctaca | gtggaaaccc | ctcatcacaa | cttaaacaac       600 |
| atatgtactg | aatagattt | tttaacattt | ttaactacta | tactaagtcc | agatcagttg       660 |
| gtgtcaatta | tacgaccggt | tcaacgaggc | ctgtccttgt | gtataattca | tcaaaataca       720 |
| cgaattgtgc | ggttaatgca | tatgttttg | acgcgaataa | tggcaatttt | tccacctgac       780 |
| acccaacaca | agcatgaaga | tcttgatttg | ttatataccg | ctgttagtaa | aatgatcgct       840 |
| gaaaacctaa | caagttacga | aaagagtcca | caaccgaatg | cttcttcgct | ttttggtacc       900 |
| ttaatgattt | tgaaagcgtg | cactactaat | aatgcaagtt | atattgatcg | aattttagtc       960 |
| cagtttataa | gggttctgaa | tcatcttaca | agggatcata | ttaacaccat | tggtggtaac      1020 |
| actgttatta | gccaatctcc | tgattcaaat | gctttacctt | tagaactctt | agttctctct      1080 |
| ttggaattaa | tcaagaatag | gatctttgta | atgagtgtgg | aaatcagaaa | acttttcata      1140 |
| ggcaccattt | tggttagtct | tatagaaaag | agcacggagg | taaaaattat | aaaatgtata      1200 |
| attaaaatgc | tggatgaatg | gattaaaacg | aaagagccaa | atgttatgac | acaagttcct      1260 |
| tctattcgcg | aaaagtcggc | cttgctggta | aagttaatgc | aaaacgttga | aagaaatttt      1320 |
| actgatgaaa | tagagcttaa | tatacaattc | ttggaaatca | taaatttat | atatagagat      1380 |
| gaaattctta | acaaaactga | gttaacaaac | aaactagagg | gagctttttt | aaacggatta      1440 |
| cgttttcaaa | atccaaacgt | acgctcgaaa | tttttgaga | ttttagactc | atcaatgcgg      1500 |
| cgtagacttc | acgatcgatt | gttatatata | atttgttccc | aagcttggga | cacaattggt      1560 |
| tcccattatt | ggataaaaca | atgcattgaa | ttgcttattt | taacagccaa | tacaatgatg      1620 |
| caaattcaat | gttcaaatga | acaatttaaa | atacccagca | ttacttcagt | cattccagtg      1680 |
| aattcatcag | aaacacagga | aaattccttt | gtatccttct | tatcctctca | ttccgaatct      1740 |
| tttgacatta | tacaaactgt | tgatgataaa | gacgacgtgt | atgatatcga | tttaaatgct      1800 |
| gatcgcaaag | aagattgtca | acaaatacta | ccaaatcgac | gtgttactct | tgttgaacta      1860 |
| gtttacaagc | aagctgaatt | tttagaagca | aaccgaaata | ttaggaccga | ccagatgctt      1920 |

-continued

```
gtcgccacat ctcagctatg tcatattgat acacagttag ctcaaagcgt atggttatct    1980
atgtttccac gtatttggag tatattcact gaagatcaaa ggtgtaatat cacaaaagaa    2040
ctgattccct ttttatcgtc tggaactaac gttaatcaaa aagactgcca tccaagtaca    2100
ttaaatactt ttgtagagag tttaactaaa tgtgcgccac ccatatatat tccacctaat    2160
ttattagcat acctaggcaa atctcataac ctatggcata gagctatact tgttttagaa    2220
gatatggccg ttaatcaatc aatgcaatcc aaggatattg atggcggtga aaatcaattc    2280
tctgacttgg atgtacaaca atcaaataat atatttgatt cactttcaaa atgtattct    2340 tcgatgcatg aggaagatct ttgggctggc ctatggctta aatttgcaca ctacccggaa    2400
acaaatatag ctgtttcgta tgagcaaatg ggattttcg aagaagccca aggtgcctat    2460
gatctagcaa tgaccaaatt taaacaagat ctaagtaatg gtgtagttaa tacatatgtt    2520
aatagtgaat tattattgtg ggaaaatcac tggatgcgat gtgctaaaga attgaaccaa    2580
tgggacattt tactggacta tgcccaaact aataaggaca aaaatatgtt tttgattctg    2640
gaaagttcgt ggcgcgtacc tgattggaat ttgatgaaaa tcgcactggc taaaacagaa    2700
caatgctatt taaaacacta cggctttaaa atcaacctt acaagggta tttgagtatt    2760 ctccaccaag aagaaggca aacaggcaat atcgaacgat atgttgaaat tgcatccagc    2820
ttatgcattc gtgaatggcg tcgattgccg aacatagttt cacatattca tttgccatat    2880
cttcaagcat cacaacaaat tatggagctt catgaagcaa gtcaaatcca tcagggactt    2940
gctcaatcgc gcaacaattc acttcacgat atgaaagcta tcgtgaaaac ttggcgtaat    3000
cgtttaccta ttatttctga tgacttatcg cattggagtg acatatttac atggagacaa    3060
catcactacc aaataataac acaacaccta gaacaacaat cggatcaagg aagtacaatg    3120
ctaggagttc acgcatcagc acaagctata atttcttttg gaaaaatagc tcggaaacac    3180
aatttgactg gtgtttgtca ggagacgttg tccaggatat atacaattcc gtctgttcct    3240
atcgtggatt gttttcagaa aattcggcag caagtaaaat gctacctgca aatgccctca    3300
acatctggaa aaaatgaaat taatgaagcc ttggaagtaa ttgagtccac gaatttaaaa    3360
tacttcactg gtgaaatgaa tgctgaattt tacgctctaa agggctatt attagcacaa    3420 attggaagat cagaagaggc tggaaaatca tttagtgttg ctgctcagct tcatgatggt    3480
cttaccaaag cctgggcaat gtggggtgac tatatggaac aaatattttt aaaagaaagg    3540
aaaatcacat tagccgtcga tgctttaatt tgttatttac aagcaagcag aaatcaaatt    3600
gaaagcaaaa cccgaaaata tattgcaaaa gttttgtggt ttctgtctta tgataataat    3660
actaaaatcc tcataagcac tttagaaaag catgtggcag gcattccacc ctcttattgg    3720
ctaccatgga ttcctcagtt gctctgttgc ttagaacagt tcgaagggga tgttatatta    3780
aatctcttaa gccaaattgg acgcctttat cctcaagcag tatatttccc gattcggact    3840
ttatatttga ctttaaaaat cgaacaacgc gaaaaacata aaactgctga acaggctgta    3900 aaagttcat gctcgaacat cgatggaact actttaagct ttggaagggg agcaagtcac    3960
ggaaacattc catcaataaa tcccattaaa gcaactccgc ccatgtggcg ctgctctaag    4020
gtgatgcaat acagagaga agtacatcca acaatattaa gttcattgga aggaattgta    4080
gaccaaatgg tttggtttag agaaagctgg acagaggaag ttcttcgaca actacgccaa    4140
ggcctaatta aatgctatgc catagccttt gaaaaaggg atactgttca acattctacc    4200 ataacaccctc acacgttgca ttttgtcaaa agctgggtt ctacgtttgg cattggaata    4260
gaaaatgttc cgggatcagt aacctcctca atttctaatt cagcagcctc ggagtctctt    4320
```

```
gctcgacgcg cccaagttac tttttcaagat ccagtatttc aaaaaatgaa ggagcaattc    4380
actaatgact tcgatttttc aaaacctggt gccatgaaat tgcacaactt gatatcaaaa    4440
ttaaaaacat ggataaaagt cctggagact aaagttaaaa aattacccac gtccttttg     4500 atagaagaca agtgtaggtt tttatcaaac tttagtcaga agacagctga ggttgaactt    4560
cctggagaat tgttaattcc cttatcatct cattattatg taagaatcgc aagattcatg    4620
ccgcgtgtgg aaattgtaca aaaaataac acagcagcgc gtaggttata tataagaggt     4680
actaacggga aaatctatcc gtaccttgta gttcttgatt caggtttggg agatgctcgc    4740
cgagaggaaa gagttttgca gttaaaacgc atgttgaatt actatttaga aaaacaaaaa    4800
gagacaagtc gaagatttct taacataacg gtaccaaggg ttgtcccgat atcgccccaa    4860
atgagattgg cagaagataa cccaaacagt atttcattgt taaaaatatt taaaaaatgc    4920
tgtcaaagta tgcaggttga ctacgacatg ccaatagtta agtattatga ccgtctttct    4980
gaagtacagg caagaggcac tccaactaca catacccctat tgagagaaat attctctgaa   5040
attcaatgga ctatggtccc aaaaacatta ctaaagcatt gggctttgaa acattcttg     5100 gcggctactg acttttggca tttccgaaaa atgcttaccc tgcagttggc tttggcattt    5160
ttatgcgaac acgctttgaa tcttactcga ctgaatgcgg atatgatgta ccttcatcaa    5220
gactcaggac ttatgaacat atcttatttt aagtttgatg taaatgatga taagtgccag    5280
cttaatcaac accgacctgt accatttcgc ctgactccga atgttggtga attcataaca    5340
cattttggaa taactggacc tttatctgca gcaattgtgg caacggctcg gtgttttatt    5400
caaccaaatt acaaattaag ctcaatatta caaaccattt taagagatga aataatagcc    5460
ctgcaaaaaa aaggattcag agaatgtaaa ctaatcgaag gctctgaaga ccgttattcc    5520
gatgaaaatt gtatggagca ctcagtaaac attgtgaatt cagcggtgga tatcataatg    5580
acgcgtttta ataaaatatc ttatttgat agcattgaaa ataagaagat ttccgtgctc     5640
gttcaatcgg caactaacat tgataatctt tgtcgtatgg atcctgcttg gcatccctgg    5700
ctataa                                                                5706
```

<210> SEQ ID NO 12
<211> LENGTH: 1901
<212> TYPE: PRT
<213> ORGANISM: Drosophila melanogaster

<400> SEQUENCE: 12

```
Met Val Pro Asp Ser Val Lys Arg Leu Phe Asp Ile His Gln Asn Gly
1               5                   10                  15

Thr Ala Val Leu Leu Phe Glu Arg Leu Tyr Asn Ala Leu Asn Lys
            20                  25                  30

Pro Val Ala Leu Leu Ser Cys Ser Met Val Glu Asn Lys Leu Met Gly
        35                  40                  45

Arg Asp Gln Tyr Gly Leu Val Gln Tyr Lys His Cys Ser Ala Val Lys
    50                  55                  60

Ser Gly Gly Glu Trp Gly Tyr Ile Phe Arg Ala Asp Pro Ser Thr Arg
65                  70                  75                  80

Ser Gly Pro Gly Gly Gln Gly Pro Arg Gly Arg Thr Val Thr Leu Leu
                85                  90                  95

Thr Val Asp Asp Asp Glu Glu Glu Ala Ala Ser Val Ser Lys Arg Ser
            100                 105                 110

Ala Ser Glu Asn Gly Ser Gln Leu Glu His Ala Ser Glu Ser Gly Ser
```

-continued

```
            115                 120                 125
Gln Leu Glu Leu Ala Ser Glu Asn Gly Ser Glu Leu Glu Asn Ala Cys
    130                 135                 140

Met Asn Ala Gln Thr Val Asn Lys Glu Tyr Gly Ser Glu Asn Thr Cys
145                 150                 155                 160

Val Met Leu Leu Lys Met Ala Met Arg Pro Glu Ile Trp Pro Gln Pro
                165                 170                 175

Phe Asp Ile Lys Leu Asn Trp Leu Asp Lys Val Leu Ala Thr Val Glu
            180                 185                 190

Thr Pro His His Asn Leu Asn Asn Ile Cys Thr Gly Ile Asp Phe Leu
        195                 200                 205

Thr Phe Leu Thr Thr Ile Leu Ser Pro Asp Gln Leu Val Ser Ile Ile
    210                 215                 220

Arg Pro Val Gln Arg Gly Leu Ser Leu Cys Ile Ile His Gln Asn Thr
225                 230                 235                 240

Arg Ile Val Arg Leu Met His Met Phe Leu Thr Arg Ile Met Ala Ile
                245                 250                 255

Phe Pro Pro Asp Thr Gln His Lys His Glu Asp Leu Asp Leu Leu Tyr
            260                 265                 270

Thr Ala Val Ser Lys Met Ile Ala Glu Asn Leu Thr Ser Tyr Glu Lys
        275                 280                 285

Ser Pro Gln Pro Asn Ala Ser Ser Leu Phe Gly Thr Leu Met Ile Leu
    290                 295                 300

Lys Ala Cys Thr Thr Asn Asn Ala Ser Tyr Ile Asp Arg Ile Leu Val
305                 310                 315                 320

Gln Phe Ile Arg Val Leu Asn His Leu Thr Arg Asp His Ile Asn Thr
                325                 330                 335

Ile Gly Gly Asn Thr Val Ile Ser Gln Ser Pro Asp Ser Asn Ala Leu
            340                 345                 350

Pro Leu Glu Leu Leu Val Leu Ser Leu Glu Leu Ile Lys Asn Arg Ile
        355                 360                 365

Phe Val Met Ser Val Glu Ile Arg Lys Leu Phe Ile Gly Thr Ile Leu
    370                 375                 380

Val Ser Leu Ile Glu Lys Ser Thr Glu Val Lys Ile Ile Lys Cys Ile
385                 390                 395                 400

Ile Lys Met Leu Asp Glu Trp Ile Lys Thr Lys Glu Pro Asn Val Met
                405                 410                 415

Thr Gln Val Pro Ser Ile Arg Glu Lys Ser Ala Leu Leu Val Lys Leu
            420                 425                 430

Met Gln Asn Val Glu Lys Lys Phe Thr Asp Glu Ile Glu Leu Asn Ile
        435                 440                 445

Gln Phe Leu Glu Ile Ile Asn Phe Ile Tyr Arg Asp Glu Ile Leu Lys
    450                 455                 460

Gln Thr Glu Leu Thr Asn Lys Leu Glu Gly Ala Phe Leu Asn Gly Leu
465                 470                 475                 480

Arg Phe Gln Asn Pro Asn Val Arg Ser Lys Phe Phe Glu Ile Leu Asp
                485                 490                 495

Ser Ser Met Arg Arg Leu His Asp Arg Leu Leu Tyr Ile Ile Cys
            500                 505                 510

Ser Gln Ala Trp Asp Thr Ile Gly Ser His Tyr Trp Ile Lys Gln Cys
        515                 520                 525

Ile Glu Leu Leu Ile Leu Thr Ala Asn Thr Met Met Gln Ile Gln Cys
    530                 535                 540
```

-continued

```
Ser Asn Glu Gln Phe Lys Ile Pro Ser Ile Thr Ser Val Ile Pro Val
545                 550                 555                 560

Asn Ser Ser Glu Thr Gln Glu Asn Ser Phe Val Ser Phe Leu Ser Ser
                565                 570                 575

His Ser Glu Ser Phe Asp Ile Ile Gln Thr Val Asp Asp Lys Asp Asp
            580                 585                 590

Val Tyr Asp Ile Asp Leu Asn Ala Asp Arg Lys Glu Asp Cys Gln Gln
        595                 600                 605

Ile Leu Pro Asn Arg Arg Val Thr Leu Val Glu Leu Val Tyr Lys Gln
    610                 615                 620

Ala Glu Phe Leu Glu Ala Asn Arg Asn Ile Arg Thr Asp Gln Met Leu
625                 630                 635                 640

Val Ala Thr Ser Gln Leu Cys His Ile Asp Thr Gln Leu Ala Gln Ser
                645                 650                 655

Val Trp Leu Ser Met Phe Pro Arg Ile Trp Ser Ile Phe Thr Glu Asp
            660                 665                 670

Gln Arg Cys Asn Ile Thr Lys Glu Leu Ile Pro Phe Leu Ser Ser Gly
        675                 680                 685

Thr Asn Val Asn Gln Lys Asp Cys His Pro Ser Thr Leu Asn Thr Phe
    690                 695                 700

Val Glu Ser Leu Thr Lys Cys Ala Pro Pro Ile Tyr Ile Pro Pro Asn
705                 710                 715                 720

Leu Leu Ala Tyr Leu Gly Lys Ser His Asn Leu Trp His Arg Ala Ile
                725                 730                 735

Leu Val Leu Glu Asp Met Ala Val Asn Gln Ser Met Gln Ser Lys Asp
            740                 745                 750

Ile Asp Gly Gly Glu Asn Gln Phe Ser Asp Leu Asp Val Gln Gln Ser
        755                 760                 765

Asn Asn Ile Phe Asp Ser Leu Ser Lys Met Tyr Ser Ser Met His Glu
    770                 775                 780

Glu Asp Leu Trp Ala Gly Leu Trp Leu Lys Phe Ala His Tyr Pro Glu
785                 790                 795                 800

Thr Asn Ile Ala Val Ser Tyr Glu Gln Met Gly Phe Phe Glu Glu Ala
                805                 810                 815

Gln Gly Ala Tyr Asp Leu Ala Met Thr Lys Phe Lys Gln Asp Leu Ser
            820                 825                 830

Asn Gly Val Val Asn Thr Tyr Val Asn Ser Glu Leu Leu Leu Trp Glu
        835                 840                 845

Asn His Trp Met Arg Cys Ala Lys Glu Leu Asn Gln Trp Asp Ile Leu
    850                 855                 860

Leu Asp Tyr Ala Gln Thr Asn Lys Asp Lys Asn Met Phe Leu Ile Leu
865                 870                 875                 880

Glu Ser Ser Trp Arg Val Pro Asp Trp Asn Leu Met Lys Ile Ala Leu
                885                 890                 895

Ala Lys Thr Glu Gln Cys Tyr Leu Lys His Tyr Gly Phe Lys Ile Asn
            900                 905                 910

Leu Tyr Lys Gly Tyr Leu Ser Ile Leu His Gln Glu Arg Gln Thr
        915                 920                 925

Gly Asn Ile Glu Arg Tyr Val Glu Ile Ala Ser Ser Leu Cys Ile Arg
    930                 935                 940

Glu Trp Arg Arg Leu Pro Asn Ile Val Ser His Ile His Leu Pro Tyr
945                 950                 955                 960
```

-continued

```
Leu Gln Ala Ser Gln Gln Ile Met Glu Leu His Glu Ala Ser Gln Ile
            965                 970                 975
His Gln Gly Leu Ala Gln Ser Arg Asn Asn Ser Leu His Asp Met Lys
            980                 985                 990
Ala Ile Val Lys Thr Trp Arg Asn Arg Leu Pro Ile Ile Ser Asp Asp
        995                 1000                1005
Leu Ser His Trp Ser Asp Ile Phe Thr Trp Arg Gln His His Tyr
    1010                1015                1020
Gln Ile Ile Thr Gln His Leu Glu Gln Gln Ser Asp Gln Gly Ser
    1025                1030                1035
Thr Met Leu Gly Val His Ala Ser Ala Gln Ala Ile Ile Ser Phe
    1040                1045                1050
Gly Lys Ile Ala Arg Lys His Asn Leu Thr Gly Val Cys Gln Glu
    1055                1060                1065
Thr Leu Ser Arg Ile Tyr Thr Ile Pro Ser Val Pro Ile Val Asp
    1070                1075                1080
Cys Phe Gln Lys Ile Arg Gln Val Lys Cys Tyr Leu Gln Met
    1085                1090                1095
Pro Ser Thr Ser Gly Lys Asn Glu Ile Asn Glu Ala Leu Glu Val
    1100                1105                1110
Ile Glu Ser Thr Asn Leu Lys Tyr Phe Thr Gly Glu Met Asn Ala
    1115                1120                1125
Glu Phe Tyr Ala Leu Lys Gly Leu Leu Leu Ala Gln Ile Gly Arg
    1130                1135                1140
Ser Glu Glu Ala Gly Lys Ser Phe Ser Val Ala Ala Gln Leu His
    1145                1150                1155
Asp Gly Leu Thr Lys Ala Trp Ala Met Trp Gly Asp Tyr Met Glu
    1160                1165                1170
Gln Ile Phe Leu Lys Glu Arg Lys Ile Thr Leu Ala Val Asp Ala
    1175                1180                1185
Leu Ile Cys Tyr Leu Gln Ala Ser Arg Asn Gln Ile Glu Ser Lys
    1190                1195                1200
Thr Arg Lys Tyr Ile Ala Lys Val Leu Trp Phe Leu Ser Tyr Asp
    1205                1210                1215
Asn Asn Thr Lys Ile Leu Ile Ser Thr Leu Glu Lys His Val Ala
    1220                1225                1230
Gly Ile Pro Pro Ser Tyr Trp Leu Pro Trp Ile Pro Gln Leu Leu
    1235                1240                1245
Cys Cys Leu Glu Gln Phe Glu Gly Asp Val Ile Leu Asn Leu Leu
    1250                1255                1260
Ser Gln Ile Gly Arg Leu Tyr Pro Gln Ala Val Tyr Phe Pro Ile
    1265                1270                1275
Arg Thr Leu Tyr Leu Thr Leu Lys Ile Glu Gln Arg Glu Lys His
    1280                1285                1290
Lys Thr Ala Glu Gln Ala Val Lys Ser Ser Cys Ser Asn Ile Asp
    1295                1300                1305
Gly Thr Thr Leu Ser Phe Gly Arg Gly Ala Ser His Gly Asn Ile
    1310                1315                1320
Pro Ser Ile Asn Pro Ile Lys Ala Thr Pro Pro Met Trp Arg Cys
    1325                1330                1335
Ser Lys Val Met Gln Leu Gln Arg Glu Val His Pro Thr Ile Leu
    1340                1345                1350
Ser Ser Leu Glu Gly Ile Val Asp Gln Met Val Trp Phe Arg Glu
```

-continued

```
              1355                1360                1365

Ser Trp Thr Glu Val Leu Arg Gln Leu Arg Gln Gly Leu Ile
    1370            1375                1380

Lys Cys Tyr Ala Ile Ala Phe Glu Lys Arg Asp Thr Val Gln His
    1385            1390                1395

Ser Thr Ile Thr Pro His Thr Leu His Phe Val Lys Lys Leu Gly
    1400            1405                1410

Ser Thr Phe Gly Ile Gly Ile Glu Asn Val Pro Gly Ser Val Thr
    1415            1420                1425

Ser Ser Ile Ser Asn Ser Ala Ala Ser Glu Ser Leu Ala Arg Arg
    1430            1435                1440

Ala Gln Val Thr Phe Gln Asp Pro Val Phe Gln Lys Met Lys Glu
    1445            1450                1455

Gln Phe Thr Asn Asp Phe Asp Phe Ser Lys Pro Gly Ala Met Lys
    1460            1465                1470

Leu His Asn Leu Ile Ser Lys Leu Lys Thr Trp Ile Lys Val Leu
    1475            1480                1485

Glu Thr Lys Val Lys Lys Leu Pro Thr Ser Phe Leu Ile Glu Asp
    1490            1495                1500

Lys Cys Arg Phe Leu Ser Asn Phe Ser Gln Lys Thr Ala Glu Val
    1505            1510                1515

Glu Leu Pro Gly Glu Leu Leu Ile Pro Leu Ser Ser His Tyr Tyr
    1520            1525                1530

Val Arg Ile Ala Arg Phe Met Pro Arg Val Glu Ile Val Gln Lys
    1535            1540                1545

Asn Asn Thr Ala Ala Arg Arg Leu Tyr Ile Arg Gly Thr Asn Gly
    1550            1555                1560

Lys Ile Tyr Pro Tyr Leu Val Val Leu Asp Ser Gly Leu Gly Asp
    1565            1570                1575

Ala Arg Arg Glu Glu Arg Val Leu Gln Leu Lys Arg Met Leu Asn
    1580            1585                1590

Tyr Tyr Leu Glu Lys Gln Lys Glu Thr Ser Arg Arg Phe Leu Asn
    1595            1600                1605

Ile Thr Val Pro Arg Val Val Pro Ile Ser Pro Gln Met Arg Leu
    1610            1615                1620

Ala Glu Asp Asn Pro Asn Ser Ile Ser Leu Leu Lys Ile Phe Lys
    1625            1630                1635

Lys Cys Cys Gln Ser Met Gln Val Asp Tyr Asp Met Pro Ile Val
    1640            1645                1650

Lys Tyr Tyr Asp Arg Leu Ser Glu Val Gln Ala Arg Gly Thr Pro
    1655            1660                1665

Thr Thr His Thr Leu Leu Arg Glu Ile Phe Ser Glu Ile Gln Trp
    1670            1675                1680

Thr Met Val Pro Lys Thr Leu Leu Lys His Trp Ala Leu Lys Thr
    1685            1690                1695

Phe Leu Ala Ala Thr Asp Phe Trp His Phe Arg Lys Met Leu Thr
    1700            1705                1710

Leu Gln Leu Ala Leu Ala Phe Leu Cys Glu His Ala Leu Asn Leu
    1715            1720                1725

Thr Arg Leu Asn Ala Asp Met Met Tyr Leu His Gln Asp Ser Gly
    1730            1735                1740

Leu Met Asn Ile Ser Tyr Phe Lys Phe Asp Val Asn Asp Asp Lys
    1745            1750                1755
```

-continued

```
Cys Gln Leu Asn Gln His Arg Pro Val Pro Phe Arg Leu Thr Pro
    1760                1765                1770
Asn Val Gly Glu Phe Ile Thr His Phe Gly Ile Thr Gly Pro Leu
    1775                1780                1785
Ser Ala Ala Ile Val Ala Thr Ala Arg Cys Phe Ile Gln Pro Asn
    1790                1795                1800
Tyr Lys Leu Ser Ser Ile Leu Gln Thr Ile Leu Arg Asp Glu Ile
    1805                1810                1815
Ile Ala Leu Gln Lys Lys Gly Phe Arg Glu Cys Lys Leu Ile Glu
    1820                1825                1830
Gly Ser Glu Asp Arg Tyr Ser Asp Gly Asn Cys Met Glu His Ser
    1835                1840                1845
Val Asn Ile Val Asn Ser Ala Val Asp Ile Ile Met Thr Arg Phe
    1850                1855                1860
Asn Lys Ile Ser Tyr Phe Asp Ser Ile Glu Asn Lys Lys Ile Ser
    1865                1870                1875
Val Leu Val Gln Ser Ala Thr Asn Ile Asp Asn Leu Cys Arg Met
    1880                1885                1890
Asp Pro Ala Trp His Pro Trp Leu
    1895                1900
```

<210> SEQ ID NO 13
<211> LENGTH: 1595
<212> TYPE: DNA
<213> ORGANISM: Drosophila melanogaster

<400> SEQUENCE: 13

```
ttcggcacga gcgactgcaa cgacgtgttg aacaattgga gatgcgaaac accatgctgg    60
cactgacgct agacgaatgc aaggagcaca ctgagcatct gtatctgcta tgcggaaagt   120
acgagtccaa tgcggttgct cttcagttgg cgcttaattg cagtgatcgc gccatcgagg   180
cctacgacgt aatgttggct ctgctcgaaa gcaagttggc actgctgggg gagaaatcag   240
tggcagcgga agagagtcga cgatcggtgg aggcggtggc caggcacctg ctagcccgtt   300
tggatagcga gaaaaacgtt tgtgagaaca gcctgggacc gtggcaacac aacatcaacc   360
tgggcccaga ggatgcccca aaaactggcc gcccgtggtg tgccgacgac gacaaccgcc   420
tgcgttacca cgtctccaag ctgaagggac gtcgttccaa tgtccagcat accattgtca   480
gtttggaatc accccttcagc gacatatacg aaagaaagcg cctggctttg gaaaaggagc   540
acgaacttcg gagcgcggac aagaagtcac ccattgactt ggagacagca gtgattatgc   600
aagaaatact cgagctgcgg gattcgaatt tgcagctgaa gacaaaaatg gaagaggccg   660
agcaggaacg gcagaacgcc aacgaacgag tgggcatact ccacgaagcc ctaaagcagc   720
tacaggcaaa caaccgggtc tcgtattcgg aggcggagca tgcggctctc acagagcagc   780
agttggtgga ggccttaact cgagaaacgg agctcaaggg tcgcatacag acgctattgg   840
caaatgtaac agcttcgcag aaggccttcg acgaaaaata cgagcaactg catcagaacg   900
tgcgtgaact gcagaaatcc aaccacaatc tgggccaaat gttagatcac accaagcgca   960
agtaccagct gcgggtgagg aagctagagc agaagattgt tgacctgcgg ctggactacg  1020
agcaaggcca taaccatgtt cctgagacta ctctgtagga aacgcatgac gaccttccag  1080
gaggactgag caactgggcg tggagcgggc gcgttgtca catatcccgc aaaagatctt  1140
tccctctcga tcatatcgct tattttacct ttaatgcaat gaccacccgc ccagcagtcg  1200
```

-continued

```
ccgtggatcc gccatgacca agacagtatc acgaatgtgc catgcgactt aattgcagtc    1260
ggctggggct tgggcggtgt ccctgcctcg cagataaggc tgcagtaact acatactcaa    1320
atacatacat attcagaggt gccatgagca aggctccacc aacctatcca tagatccgtg    1380
ggattggagc atccgtctat gggccacaag caattacata tacacacata cgaatagaca    1440
aactaaggag ttattcaaga cgcatacacg ggatcctata tttatacaat gtattcgcat    1500
tttgcttgtt atatgattca atatgtattt aaaactgtac aaaatataaa acgtctacta    1560
aaactcgaaa aaaaaaaaaa aaaaaaaaaa aaaaa                                1595
```

<210> SEQ ID NO 14
<211> LENGTH: 338
<212> TYPE: PRT
<213> ORGANISM: Drosophila melanogaster

<400> SEQUENCE: 14

```
Met Arg Asn Thr Met Leu Ala Leu Thr Leu Asp Glu Cys Lys Glu His
1               5                   10                  15

Thr Glu His Leu Tyr Leu Leu Cys Gly Lys Tyr Glu Ser Asn Ala Val
            20                  25                  30

Ala Leu Gln Leu Ala Leu Asn Cys Ser Asp Arg Ala Ile Glu Ala Tyr
        35                  40                  45

Asp Val Met Leu Ala Leu Leu Glu Ser Lys Leu Ala Leu Leu Gly Glu
    50                  55                  60

Lys Ser Val Ala Ala Glu Glu Ser Arg Arg Ser Val Glu Ala Val Ala
65                  70                  75                  80

Arg His Leu Leu Ala Arg Leu Asp Ser Glu Lys Asn Val Cys Glu Asn
                85                  90                  95

Ser Leu Gly Pro Trp Gln His Asn Ile Asn Leu Gly Pro Glu Asp Ala
            100                 105                 110

Pro Lys Thr Gly Arg Pro Trp Cys Ala Asp Asp Asn Arg Leu Arg
        115                 120                 125

Tyr His Val Ser Lys Leu Lys Gly Arg Arg Ser Asn Val Gln His Thr
    130                 135                 140

Ile Val Ser Leu Glu Ser Pro Phe Ser Asp Ile Tyr Glu Arg Lys Arg
145                 150                 155                 160

Leu Ala Leu Glu Lys Glu His Glu Leu Arg Ser Ala Asp Lys Lys Ser
                165                 170                 175

Pro Ile Asp Leu Glu Thr Ala Val Ile Met Gln Glu Ile Leu Glu Leu
            180                 185                 190

Arg Asp Ser Asn Leu Gln Leu Lys Thr Lys Met Glu Glu Ala Glu Gln
        195                 200                 205

Glu Arg Gln Asn Ala Asn Glu Arg Val Gly Ile Leu His Glu Ala Leu
    210                 215                 220

Lys Gln Leu Gln Ala Asn Asn Arg Val Ser Tyr Ser Glu Ala Glu His
225                 230                 235                 240

Ala Ala Leu Thr Glu Gln Gln Leu Val Glu Ala Leu Thr Arg Glu Thr
                245                 250                 255

Glu Leu Lys Gly Arg Ile Gln Thr Leu Leu Ala Asn Val Thr Ala Ser
            260                 265                 270

Gln Lys Ala Phe Asp Glu Lys Tyr Glu Gln Leu His Gln Asn Val Arg
        275                 280                 285

Glu Leu Gln Lys Ser Asn His Asn Leu Gly Gln Met Leu Asp His Thr
    290                 295                 300
```

-continued

```
Lys Arg Lys Tyr Gln Leu Arg Val Arg Lys Leu Glu Gln Lys Ile Val
305                 310                 315                 320

Asp Leu Arg Leu Asp Tyr Glu Gln Gly His Asn His Val Pro Glu Thr
            325                 330                 335

Thr Leu
```